(12) United States Patent
He et al.

(10) Patent No.: US 11,008,368 B2
(45) Date of Patent: May 18, 2021

(54) ENGINEERED HCV E2 IMMUNOGENS AND RELATED VACCINE COMPOSITIONS

(71) Applicant: THE SCRIPPS RESEARCH INSTITUTE, La Jolla, CA (US)

(72) Inventors: Linling He, San Diego, CA (US); Jiang Zhu, San Diego, CA (US); Erick Giang, San Diego, CA (US); Mansun Law, San Diego, CA (US); Ian Wilson, La Jolla, CA (US); Netanel Tzarum, Jerusalem (IL)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/938,105

(22) Filed: Jul. 24, 2020

(65) Prior Publication Data

US 2021/0024585 A1 Jan. 28, 2021

Related U.S. Application Data

(60) Provisional application No. 62/879,100, filed on Jul. 26, 2019.

(51) Int. Cl.
| | | |
|---|---|---|
| C07K 14/005 | (2006.01) | |
| C12N 7/00 | (2006.01) | |
| A61K 39/29 | (2006.01) | |
| A61K 47/69 | (2017.01) | |
| A61P 31/14 | (2006.01) | |

(52) U.S. Cl.
CPC ............ *C07K 14/005* (2013.01); *A61K 39/29* (2013.01); *A61K 47/6929* (2017.08); *A61P 31/14* (2018.01); *C12N 7/00* (2013.01); *C12N 2770/24222* (2013.01); *C12N 2770/24234* (2013.01)

(58) Field of Classification Search
None
See application file for complete search history.

(56) References Cited

U.S. PATENT DOCUMENTS

2018/0030429 A1* 2/2018 King .................... C12N 9/88

FOREIGN PATENT DOCUMENTS

WO WO 2010/047829 A1 * 4/2010

OTHER PUBLICATIONS

Hsia et al., Nature, 2016, vol. 535, pp. 136-147 and p. 150. (Year: 2016).*
Shan et al., J. Immunology, 1999, 162:6589-6595. (Year: 1999).*
Duncan et al., Vaccines, 2020, 8(1), 90, 23 pages. (Year: 2020).*
Kong et al., Hepatitis C Virus E2 Envelope Glycoprotein Core Structure, Science 342(6162):1090-1094 (2013).
Kong et al., Structural Flexibility at a Major Conserved Antibody Target on Hepatitis C Virus E2 Antigen, PNAS 113(45): 12768-12773 (2016).
Keck et al., Mapping 408 Determinants of Virus Neutralization and Viral Escape for Rational Design of a Hepatitis 409 C Virus Vaccine, Front. Immunol. 9, 1194 (2018).
Keck et al., Broadly Neutralizing Antibodies from an Individual that Naturally 383 Cleared Multiple Hepatitis C Virus Infections Uncover Molecular Determinants for E2 384 targeting and vaccine design. PLoS Pathog 15, e1007772 (2019).
Tzarum et al., The Neutralizing Face of Hepatitis C Virus E2 Envelope 371 Glycoprotein, Front. Immunol. 9, 1315 (2018).
Tzarum et al., Genetic and structural Insights into Broad Neutralization of Hepatitis 369 C Virus by Human VH1-69 Antibodies, Sci Adv 5, eaav1882 (2019).
Khan et al., Structure of the Core Ectodomain of the Hepatitis C Virus Envelope 322 Glycoprotein 2, Nature 509, 381-384 (2014).

* cited by examiner

*Primary Examiner* — Stacy B Chen
(74) *Attorney, Agent, or Firm* — Hugh Wang; Thomas Fitting

(57) ABSTRACT

The present invention provides novel engineered HCV E2 polypeptide immunogens and related vaccine compositions that display the engineered E2 polypeptides. The invention also provides methods of using such immunogens and vaccine compositions in various therapeutic applications, e.g., for preventing or treating HCV infections.

21 Claims, 60 Drawing Sheets

Specification includes a Sequence Listing.

Thermostability of E2 cores dervied from HCV genotypes 1 and 6 [a]
| | H77 (1a) | | | | HK6a (6a) | | |
|---|---|---|---|---|---|---|---|
| | E2c3 | E2mc3 | E2mc3-v1 | E2mc3-v6 | E2c3 | E2mc3 | E2mc3-v1 |
| $T_m$(°C) | 75.7 | 79.9 | 80.9 | 80.1 | 78.0 | 77.9 | 79.4 |
| $\Delta T_{1/2}$(°C) | 10.8 | 9.5 | 9.5 | 9.3 | 8.5 | 8.9 | 10.0 |
[a] $T_m$ and $\Delta T_{1/2}$ are derived from different scanning calorimetry (DSC) analysis.

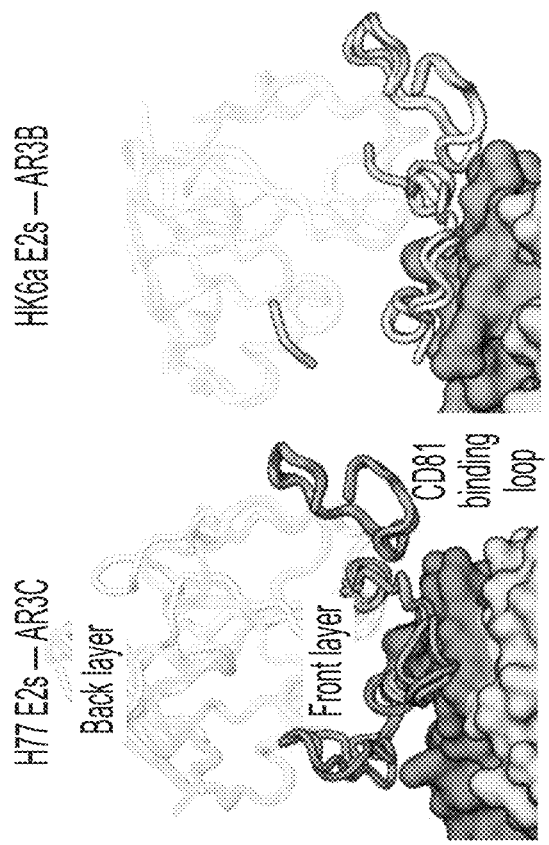
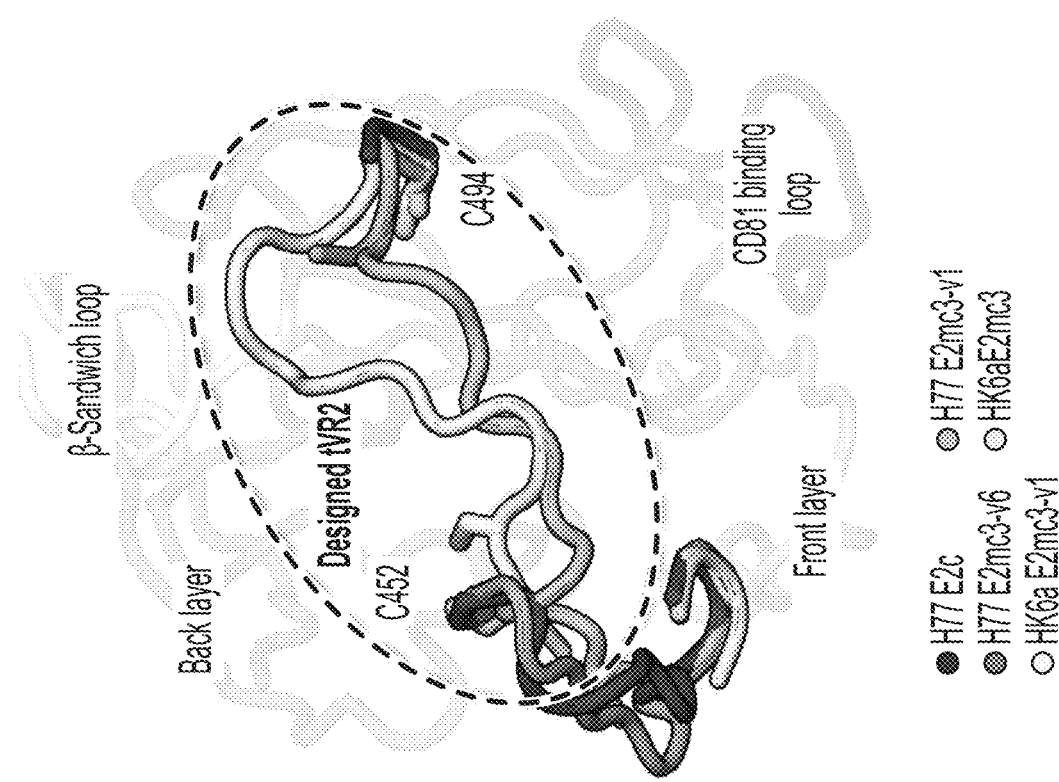
FIG. 2D
FIG. 2C

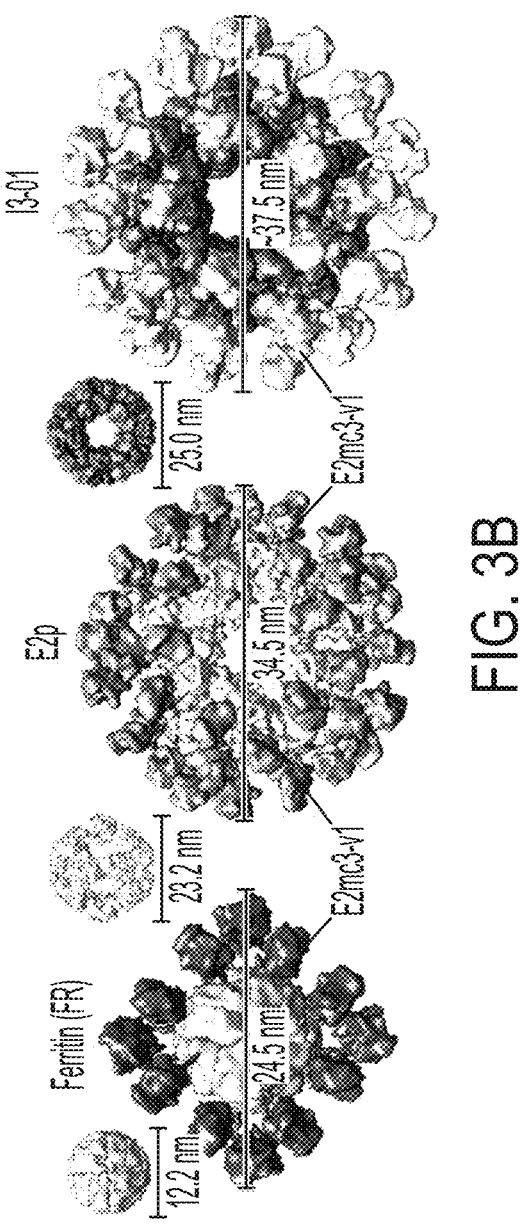
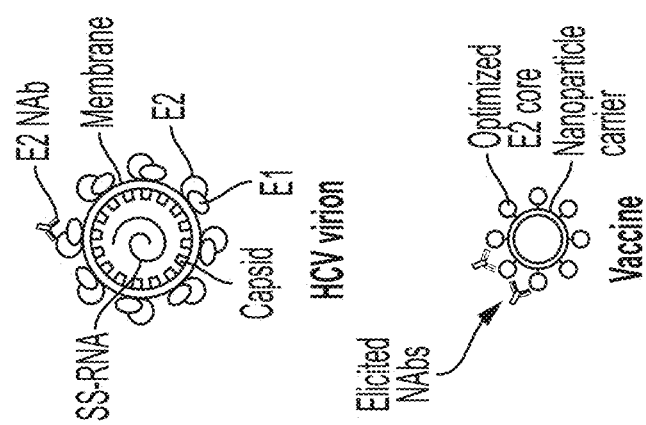
FIG. 3A
FIG. 3B

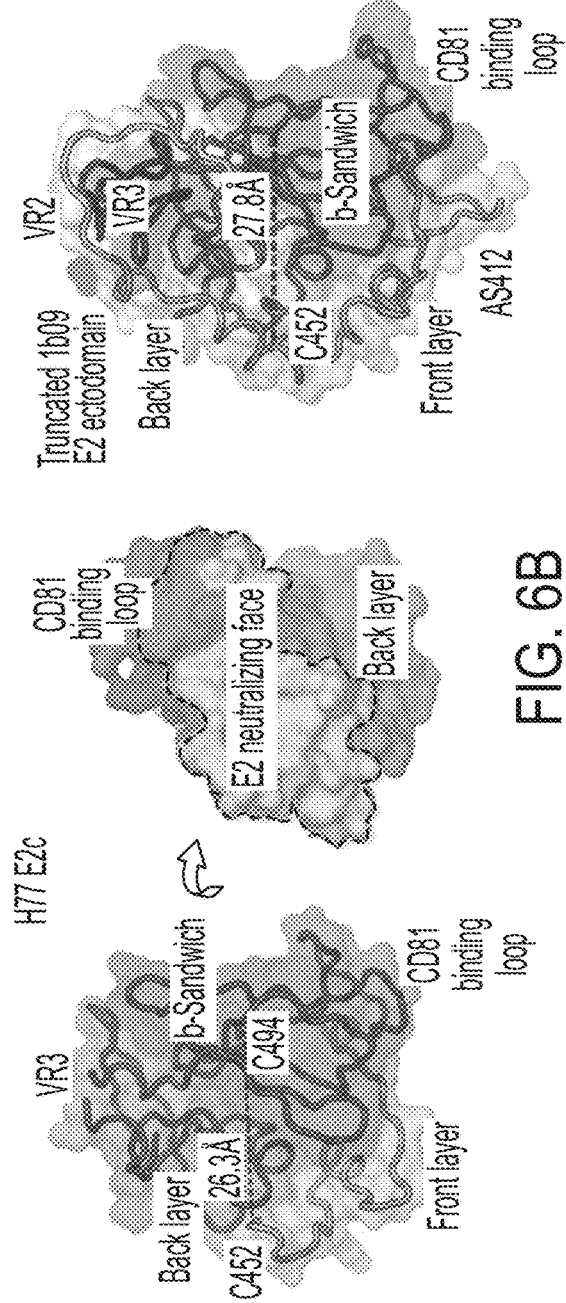
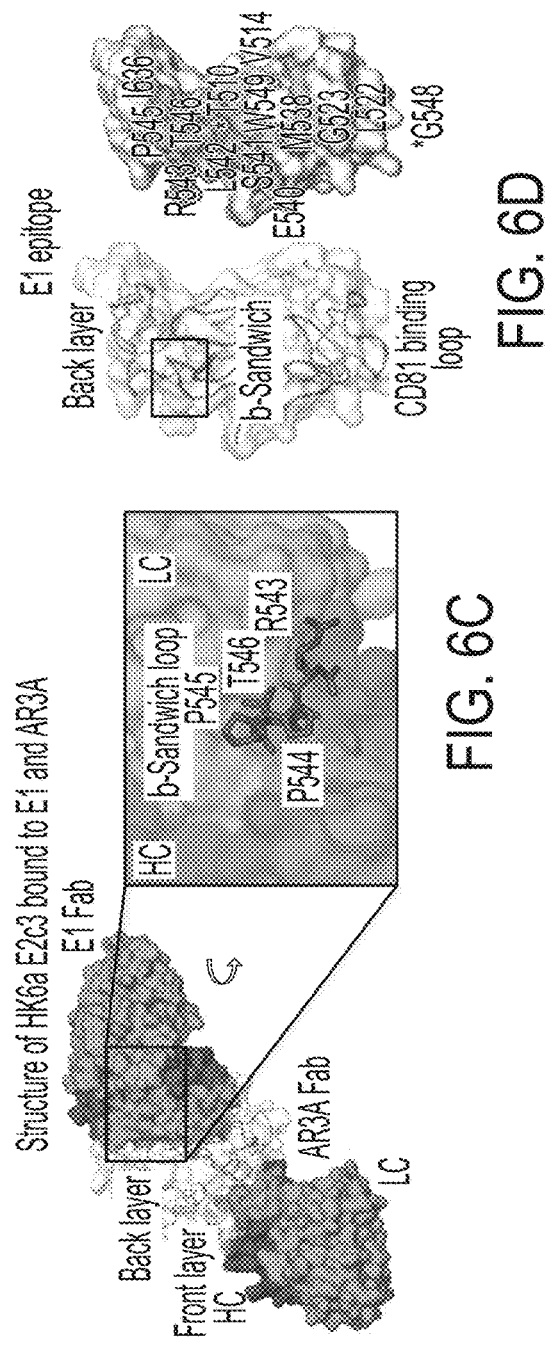
FIG. 6B
FIG. 6C
FIG. 6D

H77 E2c: known antibody epitopes

CD81 binding loop

Front layer

AR3:
AR3C (

$EC_{50}$ values of H77 E2 core constructs binding to 12 HCV-specific antibodies[a].

| | HCV1 | HC33.1 | HC84.1 | AR3C | HEPC3 | HEPC74 | 212.1.1 | HC1AM | AR1A | AR1B | E1 | AR2A |
|---|---|---|---|---|---|---|---|---|---|---|---|---|
| E2c3 | 2.022 | 1.153 | 0.6954 | 0.1458 | 0.3926 | 0.1335 | 2.479 | 0.1379 | 1.56 | 0.1084 | 0.1799 | 0.07568 |
| E2mc3 | 0.2485 | 0.1481 | 0.1269 | 0.17 | 1.286 | 2.198 | 1.215 | 0.07587 | 0.3604 | - | - | 0.02879 |
| E2mc3-v1 | 0.5451 | 0.1114 | 0.08747 | 0.04025 | 1.938 | 0.6034 | 1.065 | 0.07059 | 0.5547 | - | - | 0.02548 |
| E2mc3-v2 | 0.5896 | 0.1219 | 0.09616 | 0.09921 | 2.296 | 1.395 | 1.045 | 0.02245 | 0.2802 | - | - | 0.02889 |
| E2mc3-v3 | 0.3661 | 0.04867 | 0.08207 | 0.09939 | 4.551 | 1.427 | 0.8706 | 0.02003 | 0.2646 | - | - | 0.02851 |
| E2mc3-v4 | 0.3184 | 0.06764 | 0.07956 | 0.07655 | 2.637 | 0.4576 | 0.4189 | 0.01254 | 0.1926 | - | - | 0.02373 |
| E2mc3-v5 | 0.4349 | 0.09598 | 0.08494 | 0.05845 | 2.634 | 0.5341 | 0.2482 | 0.007939 | 0.3064 | - | - | 0.03428 |
| E2mc3-v6 | 0.3588 | 0.08911 | 0.04386 | 0.119 | 2.864 | 0.4247 | 0.2895 | 0.01092 | 0.2432 | - | - | 0.02549 |
| E2mc3-v7 | 0.2567 | 0.05072 | 0.04014 | 0.05046 | 2.719 | 0.4663 | 0.313 | 0.01209 | 0.2532 | - | - | 0.02785 |
| E2mc3-v8 | 0.2086 | 0.05031 | 0.04738 | 0.08043 | 3.186 | 1.098 | 0.2663 | 0.009017 | 0.2487 | - | - | 0.0201 |
| E2mc3-v9 | 0.3242 | 0.05871 | 0.05566 | 0.08429 | 2.568 | 0.3426 | 0.1992 | 0.01026 | 0.2615 | - | - | 0.02962 |
| E2mc3-v10 | 0.2225 | 0.09384 | 0.04887 | 0.08056 | 0.7269 | 0.1174 | 0.1355 | 0.007812 | 0.2874 | - | - | 0.0284 |

[a] $EC_{50}$ values were calculated from the besting fitting in GraphPad Prism 6.

EC50 values of HK6a E2 core constructs binding to 12 HCV-specific antibodies[a].

| | HCV1 | HC33.1 | HC84

K_D values of E2mc3 variants binding to six representative HCV-specific antibodies measured by Octet[a].

| | | HCV1 | | HC84.1 | | AR3C | | HEPC74 | | 212.1.1 | | AR2A | |
|---|---|---|---|---|---|---|---|---|---|---|---|---|---|
| | | Ave[6] | Ave[3] | Ave[6] | Ave[3] | Ave[6] | Ave[3] | Ave[6] | Ave[3] | Ave[6] | Ave[3] | Ave[6] | Ave[3] |
| H77 | E2mc3 | 5.96E-07 | 6.21E-07 | 1.00E-09 | 1.45E-09 | 1.20E-08 | 1.26E-08 | 1.26E-08 | 1.20E-08 | 2.27E-09 | 3.04E-09 | 9.74E-09 | 6.61E-09 |
| | E2mc3-v1 | 5.19E-08 | 5.16E-08 | 2.24E-09 | 2.37E-09 | 1.73E-08 | 1.93E-08 | 2.55E-08 | 2.72E-08 | 5.28E-09 | 6.06E-09 | 8.76E-09 | 6.17E-09 |
| | E2mc3-v6 | 4.60E-08 | 4.83E-08 | 4.97E-09 | 4.91E-09 | 1.95E-08 | 2.23E-08 | 1.84E-08 | 2.21E-08 | 4.27E-09 | 5.24E-09 | 9.47E-09 | 5.92E-09 |
| HK6a | E2mc3 | 6.99E-08 | 7.10E-08 | 2.85E-09 | 2.98E-09 | 1.67E-09 | 2.06E-09 | 1.19E-07 | 1.29E-07 | 1.16E-08 | 6.11E-09 | — | — |
| | E2mc3-v1 | 8.75E-08 | 8.38E-08 | 2.68E-09 | 2.61E-09 | 1.60E-09 | 1.98E-09 | 1.20E-07 | 1.26E-07 | 5.78E-08 | 8.28E-08 | 5.18E-08 | 2.62E-08 |

FIG. 7J

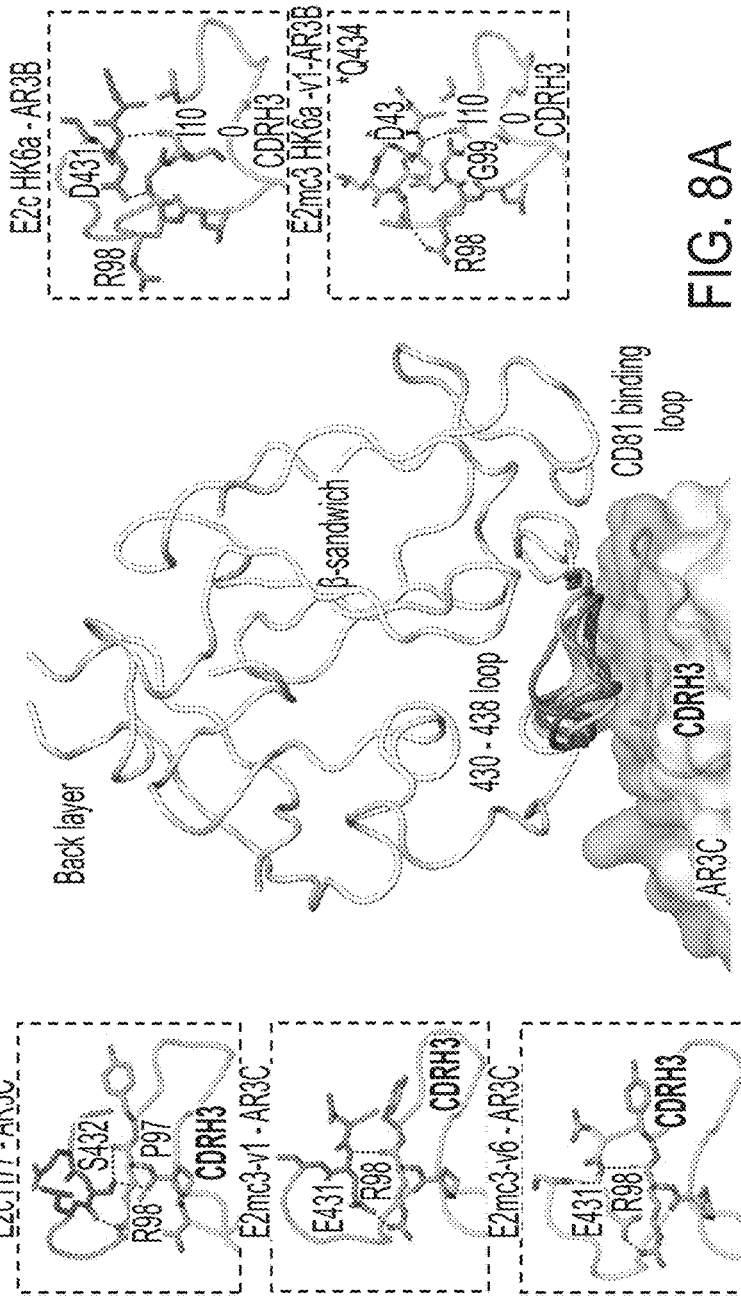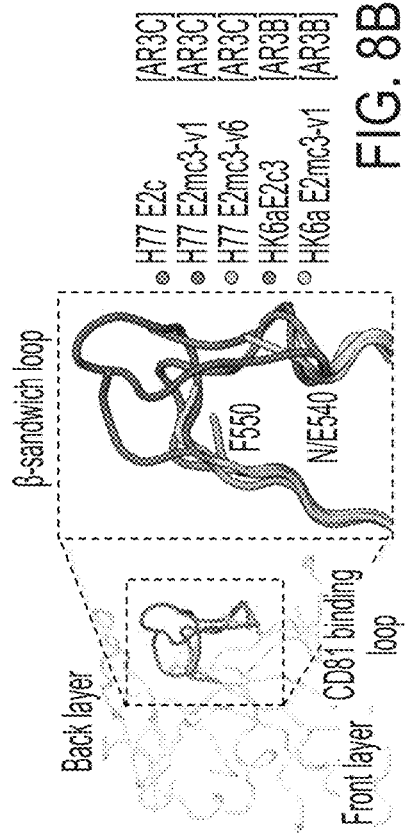
FIG. 8A
FIG. 8B

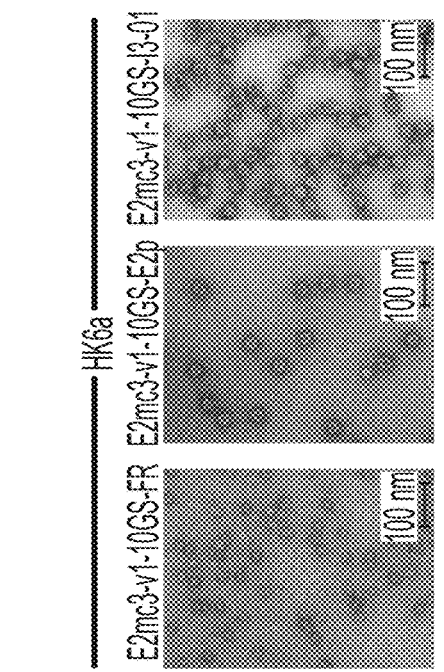
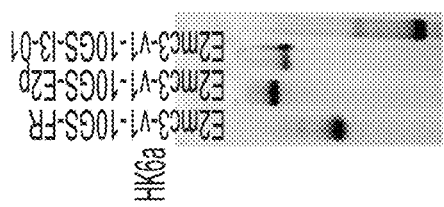
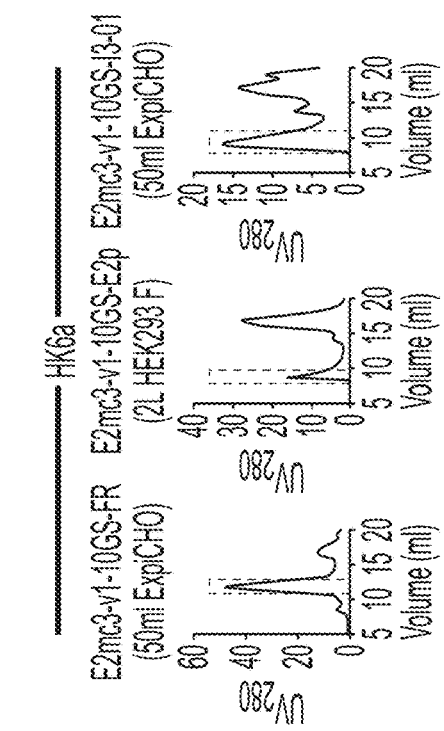
FIG. 10A
FIG. 10B
FIG. 10C

$EC_{50}$ values of various H77 E2 core nanoparticles binding to 12 HCV-specific anitbodies [a].

| | HCV1 | HC33 | HC84.1 | AR3C | HEPC3 | HEPC74 | 212.1.1 | HC1AM | AR1A | AR1B | E1 | AR2A |
|---|---|---|---|---|---|---|---|---|---|---|---|---|
| E2c3 | 2.022 | 1.153 | 0.6954 | 0.1458 | 0.3926 | 0.1335 | 2.479 | 0.1379 | 1.56 | 0.1084 | 0.1799 | 0.07568 |
| E2mc3 | 0.2485 | 0.1481 | 0.1269 | 0.17 | 1.286 | 2.198 | 1.215 | 0.07587 | 0.3604 | - | - | 0.02879 |
| E2mc3-v1 | 0.5451 | 0.1114 | 0.08747 | 0.04025 | 1.938 | 0.6034 | 1.065 | 0.07059 | 0.5547 | - | - | 0.02548 |
| v1-10GS-FR | 0.05775 | 0.01682 | 0.007175 | 0.007275 | 0.03598 | 0.01634 | 0.02125 | 0.007 | 0.0214 | - | - | 0.003544 |
| v1-10GS-E2p | 0.1301 | 0.0311 | 0.01563 | 0.01266 | 0.03929 | 0.01786 | 0.01591 | 0.006578 | 0.02986 | - | - | 0.01755 |
| v1-10GS-I3-01 | 0.07697 | 0.01976 | 0.01088 | 0.01108 | 0.02433 | 0.01551 | 0.01348 | 0.005776 | 0.02758 | - | - | 0.01209 |

[a] $EC_{50}$ values were calculated from the besting fitting in Prism.

$EC_{50}$ values of various HK6a E2 core nanoparticles binding to 12 HCV-specific anitbodies [a].

| | HCV1 | HC33 | HC84.1 | AR3C | HEPC3 | HEPC74 | 212.1.1 | HC1AM | AR1A | AR1B | E1 | AR2A |
|---|---|---|---|---|---|---|---|---|---|---|---|---|
| E2c3 | 0.8293 | 0.4099 | 0.08365 | 0.02219 | 2.637 | 15.88 | - | 0.0418 | - | - | - | - |
| E2mc3 | 0.3883 | 0.1034 | 0.03069 | 0.01498 | 4.767 | 12.29 | - | 0.02714 | - | - | - | - |
| E2mc3-v1 | 0.7244 | 0.1054 | 0.02383 | 0.01109 | 2.938 | 0.771 | - | 0.02011 | - | - | - | - |
| v1-10GS-FR | 0.0923 | 0.02377 | 0.007617 | 0.007139 | 0.1703 | 0.2297 | 6.501 | 0.003927 | - | - | - | - |
| v1-10GS-E2p | 0.1586 | 0.03368 | 0.006394 | 0.005718 | 0.02632 | 0.0206 | 0.4494 | 0.003214 | 1.405 | - | - | 0.07849 |
| v1-10GS-I3-01 | 0.04669 | 0.01564 | 0.008569 | 0.005155 | 0.1617 | 0.1534 | 0.7927 | 0.002361 | 6.271 | - | - | 0.1968 |

[a] $EC_{50}$ values were calculated from the besting fitting in Prism.

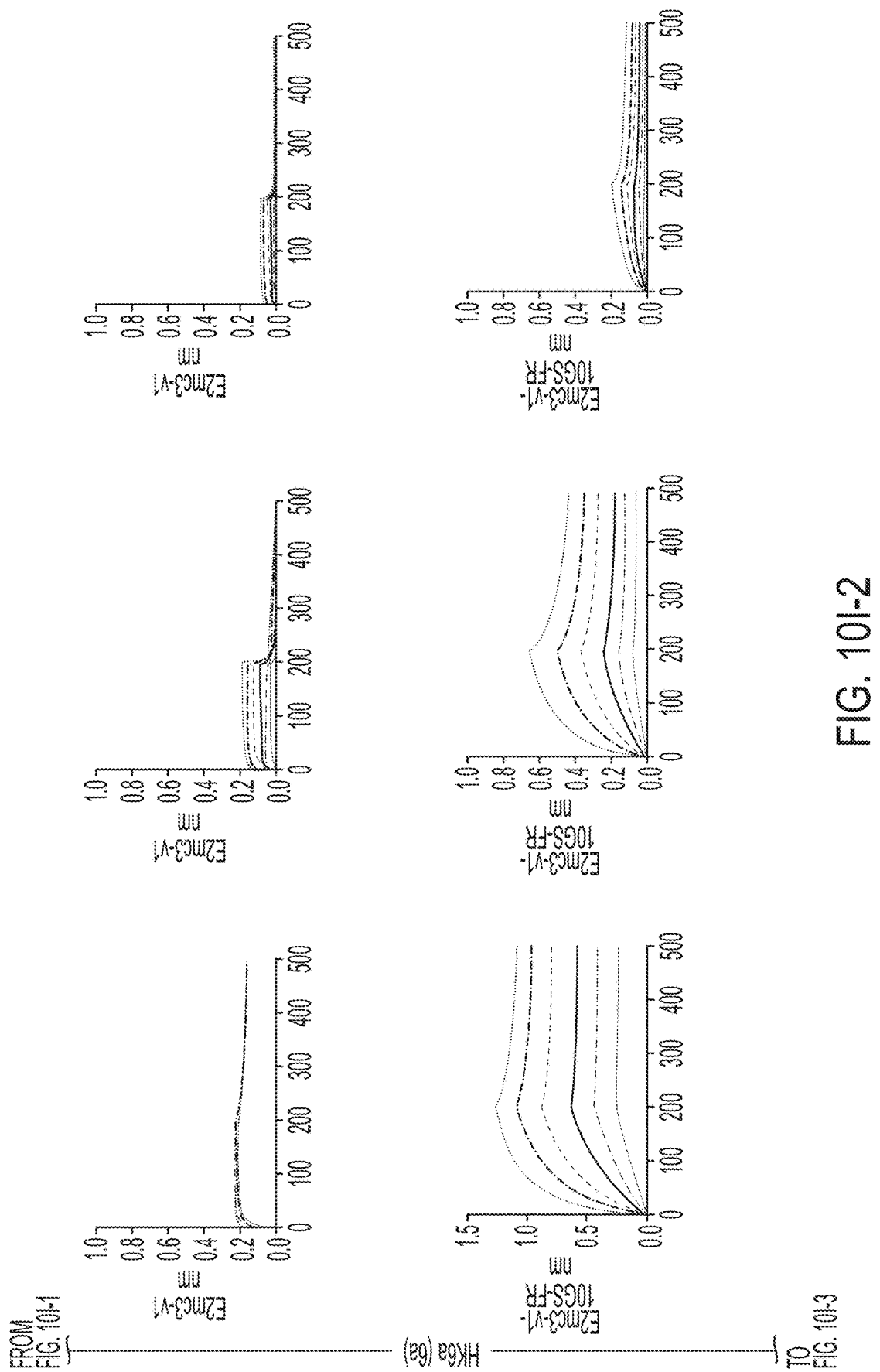

$EC_{50}$ values of mouse sera from study #1 binding o H77 E2mc3-v1[a]

| | W2 | | | W5 | | | W8 | | | W11 | | |
|---|---|---|---|---|---|---|---|---|---|---|---|---|
| | E2mc3-v1 | E2mc3-v1-FR | E2mc3-v1-E2p | E2mc3-v1 | E2mc3-v1-FR | E2mc3-v1-E2p | E2mc3-v1 | E2mc3-v1-FR | E2mc3-v1-E2p | E2mc3-v1 | E2mc3-v1-FR | E2mc3-v1-E2p |
| M1 | 45.65 | 187.5 | 111.4 | 16664 | 26151 | 7611 | 16656 | 20693 | 15734 | 26922 | 17649 | 17777 |
| M2 | 35.33 | 120.5 | 253.5 | 11702 | 13274 | 10329 | 24286 | 19668 | 25039 | 41201 | 14666 | 17494 |
| M3 | 27.42 | 228.7 | 421.2 | 7427 | 22099 | 14695 | 12729 | 33686 | 24650 | 25993 | 19679 | 17012 |
| M4[b] | -- | 133.5 | 379.6 | -- | 25538 | 11473 | -- | 17101 | 21928 | -- | 27042 | 16985 |
| M5 | 13.41 | 124.7 | 298.8 | 5242 | 20640 | 18250 | 6957 | 35842 | 26595 | 20309 | 16396 | 23639 |
| M6 | 38.96 | 196.4 | 199 | 12123 | 29183 | 12959 | 19740 | 22697 | 27719 | 54269 | 18537 | 23137 |
| M7 | 32.78 | 121.4 | 438.6 | 10134 | 20558 | 14652 | 13000 | 14444 | 23248 | 13421 | 10252 | 22005 |
| M8 | 48.96 | 74.5 | 403.9 | 10186 | 9582 | 12977 | 31134 | 9176 | 26215 | 28858 | 10330 | 20674 |
| M9 | 8.99 | 258.1 | 477.4 | 6559 | 10058 | 22251 | 9314 | 18901 | 19345 | 24221 | 15651 | 16983 |
| M10 | 8.097 | 315.6 | 515.7 | 4895 | 16103 | 12300 | 10764 | 21685 | 18924 | 9493 | 17209 | 20705 |

[a] In study #1, mice were injected with H77 E2mc3-v1 and three nanoparticles. The $EC_{50}$ values were calculated from the besting fitting in GraphPad Prism 6.
[b] M4 in the E2mc3-v1 group died shortly after the first injection, as indicated by "—".

$EC_{50}$ values of mouse sera from study #2 binding o H77 or HK6a E2mc3-v1[a]

| | | W2 | | | | W5 | | | | W8 | | | | W11 | | |
|---|---|---|---|---|---|---|---|---|---|---|---|---|---|---|---|---|
| | E2mc3-v1/HK6a | E2p-/HK6a | E2p-mix/H77 | E2p-mix/HK6a | E2mc3-v1/HK6a | E2p-/HK6a | E2p-mix/H77 | E2p-mix/HK6a | E2mc3-v1/HK6a | E2p-/HK6a | E2p-mix/H77 | E2p-mix/HK6a | E2mc3-v1/HK6a | E2p-/HK6a | E2p-mix/H77 | E2p-mix/HK6a |
| M1 | 36.44 | 57.23 | 306.2 | 87.92 | 2536 | 4152 | 3007 | 1177 | 23668 | 5399 | 4670 | 2171 | 27580 | 13634 | 3734 | 1375 |
| M2 | 91.76 | 85.23 | 332.7 | 78.19 | 3859 | 7285 | 3007 | 1483 | 26324 | 6025 | 4616 | 2034 | 77268 | 44791 | 4154 | 1108 |
| M3 | 51.32 | 51.48 | 399.2 | 62.26 | 2864 | 6936 | 2352 | 1128 | 5734 | 6315 | 3498 | 1668 | 18754 | 5244 | 2068 | 719.9 |
| M4[b] | 53.05 | 65.53 | 359.2 | 81.48 | 1675 | 2658 | 3169 | 1508 | 4243 | 6359 | 6933 | 4249 | 19549 | 3916 | 6201 | 3204 |
| M5 | 60.35 | 116.9 | 419.5 | 53.01 | 6542 | 10938 | 4165 | 2108 | 15942 | 14805 | 6033 | 3367 | 40012 | 9942 | 3898 | 2609 |
| M6 | 67.18 | 52.19 | 340.6 | 38.93 | 3359 | 2649 | 924 | 514.4 | 4006 | 7421 | 2276 | 886 | 73413 | 6369 | 2238 | 743 |
| M7 | 96.09 | 52.14 | 358.9 | 145.9 | 3193 | 4062 | 2111 | 767.9 | 2660 | 6536 | 4169 | 2153 | 11387 | 5148 | 2616 | 1280 |
| M8 | 31.99 | 99.93 | 482.1 | 150.3 | 4293 | 6946 | 3802 | 1447 | 6461 | 6138 | 4654 | 2050 | 74357 | 5673 | 3055 | 881.3 |
| M9 | 35.05 | 156.6 | 318.9 | 160.7 | 1430 | 5808 | 5347 | 2225 | 8582 | 3526 | 6081 | 2866 | 39734 | 3810 | 5125 | 2255 |
| M10 | 31.36 | 137.7 | 304.2 | 120.1 | 7300 | 5819 | 5406 | 2204 | 7968 | 4166 | 5594 | 2682 | 27205 | 3709 | 5003 | 2141 |

[a] In study #2, three groups of mice were injected with HK6a E2mc3-v1, HK6a E2mc3-v1-10GS-E2p, and HK6a/H77 E2mc3-v1-10GS-E2p mix. In serum analysis, the coating antigen was HK6a E2mc3-v1 for group 1 and group 2, while both H77 E2mc3-v1 and HK6a E2mc3-v1 were used as coating antigen for group 3 and analyzed in two separate experiments. In this table, the coating antigen is shown after "/". The $EC_{50}$ values were calculated from the besting fitting in GraphPad Prism 6.

| Mouse sample | Sorted cells | Frequency of E2mc3-v1-specific B cells | E2mc3-v1-specific B cells per 10 million splenic cells |
|---|---|---|---|
| G1-1 | 269 | 0.02% | 1771 |
| G1-3 | 294 | 0.01% | 769 |
| G1-5 | 70 | 0.02% | 2107 |
| G1-6 | 383 | 0.02% | 1655 |
| G1-10 | 42 | 0.01% | 1151 |
| G3-5 | 639 | 0.02% | 2065 |
| G3-7 | 519 | 0.04% | 3851 |
| G3-8 | 296 | 0.03% | 2968 |
| G3-9 | 145 | 0.02% | 1618 |
| G3-10 | 565 | 0.03% | 2962 |

H77 E2mc3-v1-specific bulk sorting of mouse splenic B cells from study #1

Antibodyomics analysis of next-generation sequencing (NGS) data obtained for E2mc3-v1-sorted mouse splenic B cells[a]

| Mouse sample | NRaw | NAlign | Chain | NChain | <Length> | NUsable | PercUsable |
|---|---|---|---|---|---|---|---|
| G1-1 | 754,261 | 448,586 | H | 292,627 | 574.1 | 286,978 | 98.1% |
|  |  |  | K | 155,959 | 515.9 | 154,780 | 99.2% |
| G1-3 | 786,781 | 509,031 | H | 351,785 | 543.4 | 350,416 | 99.6% |
|  |  |  | K | 157,246 | 518.2 | 156,928 | 99.8% |
| G1-5 | 995,967 | 250,854 | H | 13,791 | 552.7 | 13,629 | 98.8% |
|  |  |  | K | 237,163 | 508.5 | 235,538 | 99.3% |
| G1-6 | 830,128 | 96,295 | H | 57,820 | 571.1 | 55,754 | 96.4% |
|  |  |  | K | 38,475 | 555.8 | 37,189 | 96.7% |
| G1-10 | 826,370 | 358,931 | H | 180,016 | 657.9 | 170,128 | 94.5% |
|  |  |  | K | 178,915 | 505.7 | 177,145 | 99.0% |
| G3-5 | 2,370,390 | 757,676 | H | 471,407 | 636.6 | 469,623 | 99.6% |
|  |  |  | K | 286,269 | 509.2 | 285,645 | 99.8% |
| G3-7 | 2,310,407 | 378,836 | H | 194,360 | 571.7 | 193,698 | 99.7% |
|  |  |  | K | 184,476 | 498.1 | 180,878 | 98.0% |
| G3-8 | 1,215,653 | 414,054 | H | 180,968 | 625.0 | 180,367 | 99.7% |
|  |  |  | K | 233,086 | 509.9 | 232,190 | 99.6% |
| G3-9 | 1,788,762 | 348,596 | H | 191,028 | 631.3 | 188,161 | 98.5% |
|  |  |  | K | 157,568 | 506.9 | 157,069 | 99.7% |
| G3-10 | 971,175 | 471,436 | H | 262,416 | 646.6 | 260,219 | 99.2% |
|  |  |  | K | 209,020 | 524.2 | 207,506 | 99.3% |

[a] Listed items include the mouse sample ID, number of raw reads ($N_{Raw}$), number of sequences after $V_H/V_K$ gene assignment and removing fragments with a V-gene alignment of 250bp or shorter ($N_{Align}$), Chain type (H or K), number of $V_H/V_K$ chains, average read length of specific chain type, number of usable full-length antibody chains after the Antibodyomics pipeline processing ($N_{Usable}$), and percentage of usable chains (Perc$_{Usable}$=$N_{Usable}/N_{Chain} \times 100\%$). NGS was performed on Ion S5 using an Ion 530 chip.

FIG. 12C

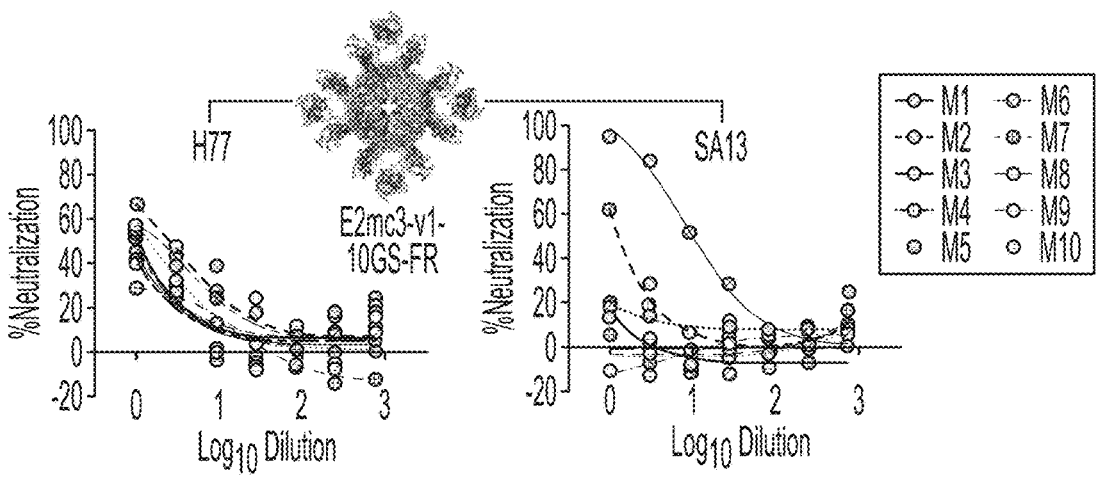

FIG. 13A

Front layer epitope-scaffold design

```
Front layer        HINSTALNCNESLNTGWLAGLFYQHKFDSSG
2WPZ_A_FL          HINSTALNCNESLNTGWLAGLFYQHKFDSSGRMKQLEDKVETNLSKVYHNENQVARL
2WPZ_A_(PDB)       ------------------------------RMKQLEDKVEENLSKVYHNENEVARL
                                                 ********* ********** ****

2WPZ_A_FL          KKLVGER
2WPZ_A_(PDB)       KKLVGER
                   *******
```

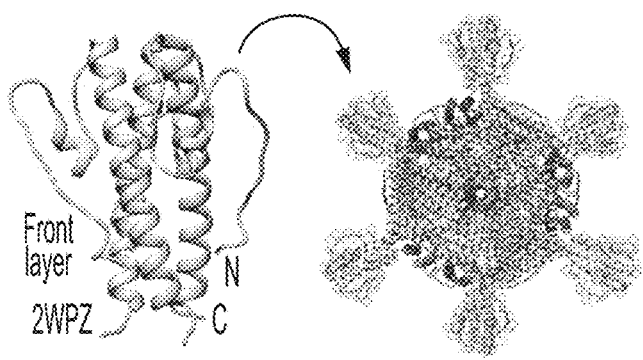

AS412 epitope-scaffold design

```
AS412              ----QLINTNG--SWHIN
1T07_A_AS412       ----RLVNCNG--SWLIGLDRPPYPGAKGEDIYNNVSRKAWDEWQKHQTMLINERRL
1T07_A_(PDB)       GHMSRTVMCRKYHEELPGLDRPPYPGAKGEDIYNNVSRKAWDEWQKHQTMLINERRL
                    * *  .   .  * ******************************************

1T07_A_AS412       NMMNAEDRKFLQQEMDKFLSGEDY
1T07_A_            NMMNAEDRKFLQQEMDKFLSGEDY
                   ************************
```

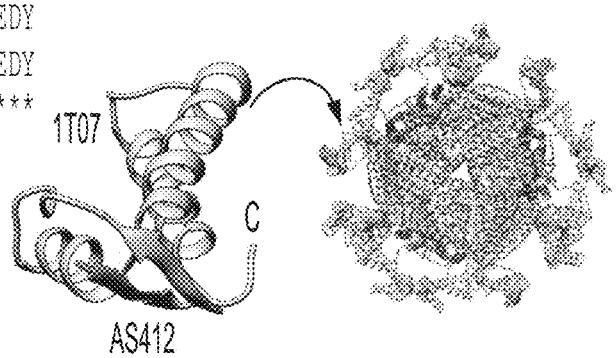

FIG. 13B

ENGINEERED HCV E2 IMMUNOGENS AND RELATED VACCINE COMPOSITIONS

CROSS-REFERENCE TO RELATED APPLICATIONS

The subject patent application claims the benefit of priority to U.S. Provisional Patent Application No. 62/879,100 (filed Jul. 26, 2019). The full disclosure of the priority application is incorporated herein by reference in its entirety and for all purposes.

STATEMENT OF GOVERNMENT SUPPORT

This invention was made with government support under contracts AI129698, AI125078, AI123861, AI079031 and AI106005 awarded by the National Institutes of Health. The government has certain rights in the invention.

BACKGROUND OF THE INVENTION

Hepatitis C virus (HCV) infects 1-2% of the world population and poses a major health burden that leads to 500,000 deaths annually and an estimated 1.5-2 million new infections each year. The opioid epidemic, causing over 70,000 overdose-related deaths in 2017 alone, is directly contributing to the rapid rise of HCV infection in North America. Most HCV patients (75-85%) will develop a chronic infection resulting in hepatocellular carcinoma, cirrhosis, and other severe liver diseases. Although direct-acting antiviral (DAA) therapies are expected to increase the HCV cure rate, challenges remain because diagnosis is usually at a late stage after liver damage. DAA treatment cannot prevent HCV reinfection nor reduce the risk of liver cancer in advanced liver disease and resistance may emerge. Indeed, increased HCV-associated mortality and new infections in injection drug users (IDU) highlights the urgency in developing an effective prophylactic vaccine to combat HCV.

A major challenge in HCV vaccine development is how to elicit a broadly protective immune response to overcome the high genetic diversity of seven major HCV genotypes and more than 86 subtypes. Moreover, rapid mutation leads to viral quasispecies in infected individuals that result in immune escape. Notwithstanding, spontaneous viral clearance in 20-30% of acutely infected patients suggests that chronic HCV infection is preventable if an effective immune response can be induced by vaccination.

Despite substantial progresses in vaccine design, there are still needs in the medical field for more effective and potent vaccine immunogens, e.g., for preventing infections from non-viral or viral pathogens (e.g., HCV infection). The present invention addresses unmet needs in the art.

SUMMARY OF THE INVENTION

In one aspect, the invention provides modified HCV E2 ectodomain polypeptides. These polypeptides contain an engineered E2 ectodomain sequence that is redesigned (i.e., additionally modified) by at least one of the following: (a) a truncation in the VR2 disordered region and (b) a deletion in the β-sandwich loop connecting 13 sheets 6 and 7 of the β-sandwich domain. In some embodiments, the engineered E2 ectodomain sequence prior to the additional modification comprises SEQ ID NO:4, a conservatively modified variant or a substantially identical sequence thereof. In some of these modified HCV E2 ectodomain polypeptides, truncation of the VR2 disordered region comprises replacing residues 41-61 of SEQ ID NO:4, CPERLASCGSSGCW-HYPPRPC (SEQ ID NO:6), with CPERASGHYPRPC (SEQ ID NO:10). In some modified HCV E2 ectodomain polypeptides, truncation of the VR2 disordered region comprises replacing residues 41-61 of SEQ ID NO:4, CPER-LASCGSSGCWHYPPRPC (SEQ ID NO:6), with a sequence set forth in CXXXXXXHYPRPC (SEQ ID NO:8) or CXXXXXHYPRPC (SEQ ID NO:9), wherein X is any amino acid residue. In some of these embodiments, XXXXXX(SEQ ID NO:75) in SEQ ID NO:8 is QNWDEP (SEQ ID NO:11), KVNIDP (SEQ ID NO:12), EKVEEL (SEQ ID NO:13), PDENMK (SEQ ID NO:14), or KREEKM (SEQ ID NO:15). In some other embodiments, XXXXX (SEQ ID NO:76) in SEQ ID NO:9 is PKTEV (SEQ ID NO:16), KRVDI (SEQ ID NO:17), PSDMV (SEQ ID NO:18), PNEEE (SEQ ID NO:19), or KKEIR (SEQ ID NO:20).

In some modified HCV E2 ectodomain polypeptides of the invention, deletion of the β-sandwich loop sequence (SEW ID NO:21) from the engineered E2 ectodomain sequence SEQ ID NO:4 comprises deletion of one or more residues that form the tip of the β-sandwich loop. In some of these embodiments, residues that form the tip of the β-sandwich loop are residues 543-546 from SEQ ID NO:4. In some of these embodiments, residues 543-546 from SEQ ID NO:4, RPPL (SEQ ID NO:22), are deleted.

Some modified HCV E2 ectodomain polypeptides of the invention contain both truncation in the VR2 disordered region and deletion in the β-sandwich loop. In some of these embodiments, the modified HCV E2 ectodomain polypeptide comprises an amino acid sequence as set forth in any one of SEQ ID NOs:26-38, a conservatively modified variant or a substantially identical sequence thereof.

In some related aspects, the invention provides polynucleotides that encode the modified HCV E2 ectodomain polypeptides described herein (polypeptides set forth in SEQ ID NOs:26-38), vectors or expression constructs that harbor such a polynucleotide sequence, as well as pharmaceutical compositions that contain a modified HCV E2 ectodomain polypeptide of the invention.

In another aspect, the invention provides vaccine compositions that contain a modified HCV E2 ectodomain polypeptide described herein that is displayed on the surface of a self-assembling nanoparticle. In some embodiments, the C-terminus of the modified HCV E2 ectodomain polypeptide is fused to the N-terminus of subunit of the self-assembling nanoparticle via a linker sequence. In some of these nanoparticle vaccines, the linker sequence connecting the modified HCV E2 ectodomain polypeptide to the nanoparticle subunit comprises $(GGGGS)_2$ (SEQ ID NO:42). In various embodiments, the modified HCV E2 ectodomain polypeptide displayed on the nanoparticle comprises an amino acid sequence as set forth in any one of SEQ ID NOs:26-38, a conservatively modified variant or a substantially identical sequence thereof. In any of these embodiments, the employed self-assembling nanoparticle can have a subunit sequence as shown in SEQ ID NO:39 (E2p), SEQ ID NO:40 (I3-01), SEQ ID NO:41 (ferritin), a conservatively modified variant or a substantially identical sequence thereof.

In another related aspect, the invention provides polynucleotide sequences that encode a fusion protein containing a modified HCV E2 ectodomain polypeptide described herein and a self-assembling nanoparticle subunit. In the encoded fusion protein, typically the modified HCV E2 ectodomain polypeptide is fused at its C-terminus to the N-terminus of the self-assembling nanoparticle subunit. Another related aspect of the invention is directed to vectors or expression constructs harboring such a polynucleotide sequence. In another aspect, the invention provides pharmaceutical compositions that contain a nanoparticle particle displayed modified HCV E2 ectodomain polypeptide described herein, and optionally a pharmaceutically acceptable carrier.

In still another aspect, the invention provides methods for treating or preventing HCV infection in a subject afflicted with or at risk of developing HCV infection. These methods of the invention entail administering to the subject a pharmaceutical composition that contains a modified HCV E2 ectodomain polypeptide described herein or a nanoparticle vaccine containing the polypeptide.

A further understanding of the nature and advantages of the present invention may be realized by reference to the remaining portions of the specification and claims.

DESCRIPTION OF THE DRAWINGS

FIGS. 1A-1G show rational design of HCV E2 cores. (1A) Schematic representation of HCV E2 (amino acids 384-746) showing structural components: variable regions (VRs), antigenic site 412 (AS412), front layer, β-sandwich, CD81 binding loop, back layer, stalk trans-membrane (TM) region, and N-linked glycans and conserved disulfide bonds. Sequence alignment of the design regions between E2 and E2mc3 (see below) is shown. Sequences of VR2 disordered region (residues 452-494) (SEQ ID NO:5) and β-sandwich loop (residues 540-550) (SEQ ID NO:21) of HCV H77 isolate are shown. (1B) Structure-based design of minimal E2 cores. Left: Structure of H77 E2c (PDB ID: 4MWF) with shortened VR2 loop modeled by LOOPY loop prediction program. The redesigned β-sandwich loop and the shortened VR2 disordered region are colored in magenta. Disulfide bonds, C494-0564 and C452-C620, which anchor VR2 to the back layer, are shown. Front layer, CD81 binding loop, and back layer are also labeled. Middle 1: Structure of H77 E2mc3 with tip-truncated β-sandwich loop and further truncated VR2 disordered region (tVR2). Middle 2: root-mean-square fluctuation (RMSF) plot for redesigned tVR2 ensemble is shown with the major steps involved in the ensemble-based de novo protein design below. Right: Structure of H77 E2mc3 with five top-ranking tVR2 design variants (E2mc3 v1-v5) highlighted in a transparent molecular surface. (1C) SEC profiles of E2mc3 and variants. Left: H77 E2mc3, v1-v5, and v6-v10. Right: HK6a E2mc3 and v1. (1D) SDS-PAGE E2mc3 and variants (Left: H77; Right: HK6a). (1E) $EC_{50}$ values of H77 (upper panel) and HK6a (lower panel) E2 cores binding to 12 HCV antibodies, including eight bNAbs (HCV1, HC33, HC84.1, AR3C, HEPC3, HEPC74, 212.1.1, and HC1AM), one NAb (AR2A), and three non-NAbs (AR1A, AR1B, and E1). E2 cores tested here include E2c3, E2mc3, and E2c3 variants (10 for H77 and 1 for HK6a). (1F) Binding affinities (Kds) of H77 and HK6a E2mc3 variants for six selected HCV antibodies. (1G) Thermal stability of H77 and HK6a E2c3 and E2mc3 variants measured by DSC. Two thermal parameters, $T_m$ and $\Delta T_{1/2}$, are listed for four H77 E2 cores and three HK6a E2 cores.

FIGS. 2A-2D show structures of rationally designed HCV E2 cores. (2A) Crystal structures of H77/HK6a E2mc3 indicate an overall similar fold to H77 E2c and HK6a E2c3 (PDB: 4MWF and 6BKB). (2B) Superposition of the β-sandwich loop from the H77 E2mc3-v1 structure on the HK6a E2c3-Fab E1 complex confirming that loss of binding of E2mc3s to Fab E1 results from truncation of the β-sandwich loop. (2C) Superposition of E2 of HK6a E2c3 (PDB 6BKB), H77 E2mc3-v1, H77 E2mc3-v6, and HK6a E2mc3-v1 on the structure of H77 E2c (PDB 4MWF) illustrating the conformation of the redesigned tVR2 (a.a. 452-494). The redesigned tVR2 regions of H77 E2mc3-v1 and HK6a E2mc3-v1 structures are fully modeled but only partly in the H77 E2mc3-v6 structure. (2D) Superposition of the H77/HK6a E2mc3 structures to H77 E2c and HK6a E2c3 indicating similar conformation of the neutralization face with only local conformational changes for the redesigned VR2 E2s.

FIGS. 3A-3G show rational design of self-assembling E2 core nanoparticles. (3A) Schematic representation of HCV virion (top) and E2 core-based nanoparticle vaccine (bottom). For the HCV virion, single-stranded (SS)-RNA, capsid, membrane, and envelope glycoproteins E1 and E2 are labeled, while for the vaccine, optimized E2 core and nanoparticle carrier are labeled. (3B) Colored surface models of nanoparticle carriers (top) and E2 core-based nanoparticle vaccines (bottom). Three nanoparticle carriers shown here are 24-meric ferritin (FR) and 60-meric E2p and I3-01. Nanoparticle size is indicated by diameter (in nanometers). (3C) SEC profiles of H77 E2mc3-v1 nanoparticles obtained from a Superose 6 10/300 GL column. The particle fraction is indicated by a dotted-line box. While both FR and I3-01 nanoparticles were produced in ExpiCHO cells, E2p nanoparticles were expressed in HEK293 F cells. (3D) BN-PAGE of SEC-purified H77 E2mc3-v1 nanoparticles. (3E) Negative stain EM images of SEC-purified H77 E2mc3-v1 nanoparticles. (3F) $EC_{50}$ values of H77 (upper panel) and HK6a (lower panel) E2mc3-v1 nanoparticles binding to 12 HCV antibodies listed in FIG. 7C. (3G) Antigenic profiles of H77 (left) and HK6a (right) E2mc3-v1 and three nanoparticles against six HCV antibodies. Sensorgrams were obtained from an Octet RED96 using an antigen titration series of six concentrations (3.57-0.11 µM by twofold dilution for E2mc3-v1 and 52.08-1.63 nM by twofold dilution for nanoparticles) and quantitation biosensors, as shown in FIGS. 10H and I. The peak values at the highest concentration are listed in the matrix. Higher color intensity indicates greater binding signal measured by Octet.

FIGS. 6A-6I show sequence, structural, and computational analyses of HCV envelope glycoprotein E2 and E2 core design variants. (6A) Sequence alignment of H77 E2ΔTM, E2c, E2c3, and E2mc3 constructs (SEQ ID NOs: 1-4, respectively). Regions of HVR1, VR2, VR3, and the β-sandwich loop are marked with lines. The E2c and E2c3 mutations are labeled, and the E2mc3 mutations noted with arrows. (6B) Structures of H77 E2c (PDB: 4MWF) and 1b09 truncated E2 ectodomain (PDB: 6MEI). The protein chain is represented as a tube with the molecular surface color-coded as in FIG. 1A. (6C) Structure of HK6a E2c3 bound to E1 and AR3A. The molecular surfaces of HK6a E2c3, E1, and AR3A are shown. A close-up view of four E1-interacting amino acids at the tip of the β-sandwich loop is shown as an insert. (6D) Projection of the E1 epitope onto the E2c3 structure. Left: back layer, n-sandwich loop, and CD81 binding loop are shown as tubes within the transparent molecular surface. The tip of the β-sandwich loop is labeled with a rectangle; Right: E1-interacting amino acids are labeled on the solid molecular surface of E2. (6E) Schematic overview of the interactions between E1 mAb HC and LC CDRs (SEQ ID NOs:44-49, respectively) and E2. E2 interacting residues are highlighted for (hydrogen bonds and hydrophobic interactions. (6F) Conformational ensembles of redesigned E2mc3 tVR2 loop. E2mc3 structure is shown in ribbons and 1000 modeled loops are shown. Left: loop length #1 (13 a.a.) (SEQ ID NO:50); right: loop length #2 (12 a.a.) (SEQ ID NO:51). (6G) Distribution of Ca root-mean-square (RMS) fluctuation plotted for the two redesigned tVR2 loop ensembles. (6H) Five top-ranking designs and their energy scores for the two loop ensembles. Sequences shown are tVR2 sequence of E2mc3 (SEQ ID NO:10), and 10 fragment sequences (SEQ ID NOs:11-20, respectively) that replace the PERASG (SEQ ID NO:52) motif in the tVR2 sequence. (6I) Sequence alignment of H77 E2, H77 E2c, and HK6a E2c3 (SEQ ID NOs:53-55, respectively). Amino acids that are disordered in the crystal structures of H77 E2c-AR3C (PDB: 4MWF) and HK6a E2c3-AR3A (PDB: 6BKB) complexes are noted.

FIGS. 7A-7K show biochemical, biophysical, and antigenic characterization of E2 cores derived from H77(1a) and HK6a(6a). (7A) SEC profiles of E2c3 proteins obtained from a Superdex 200 10/300 column after immunoaffinity (AR3A) purification. (7B) SDS-page of E2c3 and E2mc3 proteins after immunoaffinity (AR3A) and SEC purification. (7C) Antigenic sites and epitopes mapped onto the H77 E2c surface (publications are listed). (7D-1 to 7D-3) ELISA binding of H77 E2c3 and E2mc3 variants to 12 HCV-specific antibodies. (7E) $EC_{50}$ values of H77 E2 core constructs binding to 12 HCV-specific antibodies. (7F-1 to 7F-2) ELISA binding of HK6a E2 E2c3 and E2mc3 variants to 12 HCV-specific antibodies. (7G) $EC_{50}$ values of HK6a E2 core constructs to 12 HCV-specific antibodies. In FIGS. 7E and 7G, $EC_{50}$ values were calculated for all ELISA plots in Prism except where the highest $OD_{450}$ value was below 0.1 or data fitting was ambiguous. (7H-1 to 7H-2) Octet binding of H77 E2mc3 variants to six HCV-specific antibodies. (7I-1 to 7I-2) Octet binding of HK6a E2mc3 variants to six HCV-specific antibodies. In FIGS. 7H-1, 7H-2, 7I-1 and 7I-2, sensorgrams were obtained from an Octet RED96 instrument using a titration series of six concentrations (3.57-0.11 µM by twofold dilution for all E2mc3 variants) and kinetics biosensors (see Methods). (7J) $K_D$ values of H77 and HK6a E2mc3 variants measured by Octet. (7K) Differential scanning calorimetry (DSC) curves of selected E2 core constructs. Two thermal parameters, $T_m$ and $T_{1/2}$, are labeled on the DSC profiles.

FIGS. 8A-8B show crystal structures of H77 E2mc3 and HK6a E2mc3. (8A) Conformational flexibility of the front layer 430-438 loop. The 430-438 loop in the H77 and HK6a E2c structures acquire different conformations yet maintain similar interactions with the Fab CDRH3 loop, indicating high flexibility of this region. (8B) The conformation of the β-sandwich loop region (a.a. 540-550) in H77 E2c, HK6a E2c3, and H77/HK6a E2mc3.

FIGS. 10A to 10I-4 show biochemical, biophysical, and antigenic characterization of E2 core nanoparticles derived from H77(1a) and HK6a(6a). (10A) SEC profiles of HK6a E2mc3-v1 nanoparticles based on FR, E2p and I3-01 obtained from a Superose 6 200 Increase 10/300 column after immunoaffinity (AR3A) purification. (10B) BN-PAGE of HK6a E2mc3-v1 nanoparticles based on FR, E2p and I3-01. (10C) Negative-stain EM images of HK6a E2mc3-v1 nanoparticles based on FR, E2p and I3-01. (10D-1 to 10D-2) ELISA binding of H77 E2c3-v1 nanoparticles to 12 HCV-specific antibodies. (10E) $EC_{50}$ values of H77 E2 E2c3-v1 nanoparticles binding to 12 HCV-specific antibodies. (10F-1 to 10F-2) ELISA binding of HK6a E2mc3-v1 nanoparticles to 12 HCV-specific antibodies. (10G) $EC_{50}$ values of HK6a E2mc3-v1 nanoparticles with 12 HCV-specific antibodies. In FIGS. 10E and 10G, $EC_{50}$ values were calculated for all ELISA plots in Prism except where the highest $OD_{450}$ value was below 0.1 or data fitting was ambiguous. (10H-1 to 10H-2) Octet binding of H77 E2mc3-v1 nanoparticles to six HCV-specific antibodies. (10I-1 to 10I-4) Octet binding of HK7a E2mc3-v1 nanoparticles to six HCV-specific antibodies. In FIGS. 10H-1, 10H-2, and 10I-1 to 10I-4, sensorgrams were obtained from an Octet RED96 instrument using a titration series of six concentrations (3.57-0.11 µM by two-fold dilution for E2mc3-v1 and 52.08-1.63 nM by twofold dilution for E2mc3-v1 nanoparticles) and quantitation biosensors.

FIGS. 11A-11D show murine antibody response during immunization at w2, w5, w8 and w11. (11A) ELISA binding of H77 E2mc3-v1 to mouse sera from groups 1, 2, and 3 in study #1, which were immunized with H77 E2mc3-v1, E2mc3-v1-10GS-FR, and E2mc3-v1-10GS-E2p, respectively, at four time points. (11B) $EC_{50}$ values of study #1 mouse sera binding to H77 E2mc3-v1 at four time points. (11C-1 to 11C-2) ELISA binding of HK6a E2mc3-v1 or H77 E2mc3-v1 to mouse sera from groups 1, 2, and 3 in study #2, which were immunized with HK6a E2mc3-v1, HK6a E2mc3-v1-10GS-E2p, and H77/HK6a E2mc3-v1-10GS-E2p mix, respectively, at four time points. Panels 1 and 2: sera from mice immunized with HK6a E2mc3-v1 (group 1) and HK6a E2mc3-v1-10GS-E2p (group 2) were tested against HK6a E2mc3-v1. Panels 3 and 4: sera from mice immunized with H77/HK6a E2mc3-v1-10GS-E2p mix (group 3) were tested against H77 E2mc3-v1 (panel 3) and HK6a E2mc3-v1 (panel 4). (11D) $EC_{50}$ values of study #2 mouse sera binding to HK6a or H77 E2mc3-v1 at four time points.

FIGS. 12A-12C show next-generation sequencing (NGS) analysis of bulk-sorted E2mc3-specific mouse splenic B cells. (12A) SEC profile of biotinylated Avi-tagged H77 E2mc3-v1, termed E2mc3-v1-Avi-Biot, obtained from a Superdex 200 10/300 column, with the peak corresponding to biotin ligase labeled on the profile. (12B) Summary of H77 E2mc3-v1-specific bulk sorting of mouse splenic B cells from study #1, groups 1 and 3. (12C) Antibodyomics analysis of NGS data obtained for E2mc3-v1-sorted mouse splenic B cells. NGS data from groups 1 and 3, a total of 10 mice, were analyzed.

FIGS. 13A-13C show analysis of mouse polyclonal serum antibody response. (13A) Neutralization of HCV H77 and SA13 isolates by mouse IgG purified from the H77 E2mc3-v1-10GS-FR group in study #1. The HCVpp neutralization assays were performed with a starting IgG concentration of 100 µg/ml and a series of 3-fold dilutions. The full neutralization curves were created to facilitate the comparison between different groups. (13B) Design of epitope-specific probes for front layer (FL) (SEQ ID NOs:56-58) and AS412 (SEQ ID NOs:59-61). Left: epitope-scaffold design showing sequence alignment of the epitope, the designed epitope-scaffold, and the original scaffold obtained from the database search (*—match and •—similar with engineered disulfide bonds); Middle: structural model of designed epitope-scaffold, with the scaffold backbone shown in tan and the FL and AS412 epitopes. Right: molecular model of nanoparticle probe, with FL and AS412 epitopes. (13C) ELISA binding of mouse sera from groups 1 and 3 in study #1, which were immunized with H77 E2mc3-v1 and E2mc3-v1-10GS-E2p, respectively, to the two epitope probes. Left: ELISA curves; Right: summary of $EC_{50}$ titers.

DETAILED DESCRIPTION

I Overview

Figure 1A:
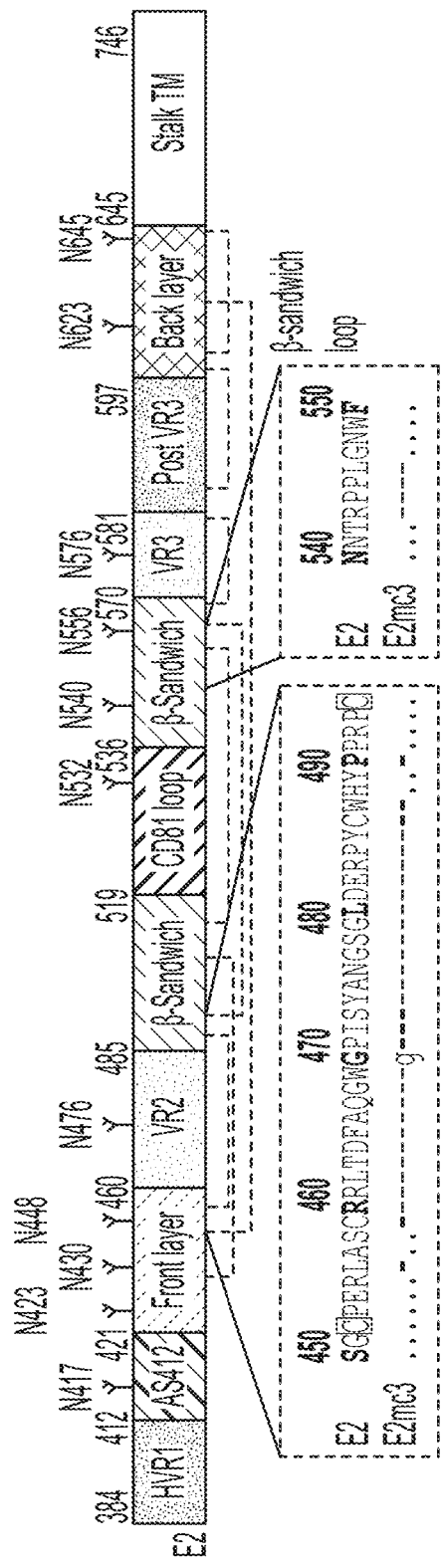

Glycoproteins E1 and E2 form a heterodimer on the HCV envelope that mediates viral entry into host hepatocytes. E2 interacts with host cellular receptors CD81 and SR-B1 and is a major target for neutralizing antibodies (NAb). Crystal structures of an E2 core (E2c) from isolate H77 (genotype 1a) with a broadly neutralizing antibody (bNAb), AR3C, and a truncated E2 from isolate J6 (genotype 2a) bound to a non-NAb, 2A12, provided the first insight into immune recognition of HCV envelope glycoproteins and paved the way for structure-based design of antiviral drugs and vaccines. Diverse vaccine strategies such as viral vectors, DNA vaccines, virus-like particles (VLP), and recombinant E2 and E1E2 proteins have been explored, but no licensed vaccine is available to prevent HCV infection. Although recombinant E1, E2 and E1E2 glycoproteins have elicited NAbs in animals and humans, neutralization breadth was limited and directed mainly to the immunodominant variable loops. Therefore, HCV vaccine efforts should be focused on design and optimization of envelope glycoprotein-based antigens capable of eliciting a bNAb response.

Over the last decade, several rational vaccine design strategies for human immunodeficiency virus type-1 (HIV) have included epitope-focused and native Env trimer-based approaches, that aim to direct the immune response to bNAb epitopes either by grafting the epitope onto heterologous scaffolds, removing or suppressing immunodominant regions, or stabilizing Env structures. Another major advance was the development of self-assembling nanoparticles (NP) to present stabilized Env trimers and epitope-scaffolds as multivalent VLP vaccines. These general design elements can, in principle, be applied to a wide range of vaccine targets including HCV. Indeed, epitope-scaffolds have been designed for conserved E1 and E2 NAb epitopes, but with no reported in vivo data or little improvement in neutralization breadth. See, e.g., He et al., Sci. Rep. 5, 12501, 2015; Pierce et al., J. Virol. 91, e01032-01017, 2017; and Sandomenico et al., J. Virol. 90, 3745-3759, 2016.

The present invention is predicated in part from the inventors' studies to redesign HCV E2 based vaccine polypeptides. Specifically, the inventors first redesigned E2 core constructs by truncating the VR2 disordered region and the β-sandwich loop, followed by computationally optimizing the truncated VR2 loop (tVR2). The redesigned HCV E2 polypeptides were found to have improved yield, higher purity and increased thermostability. They also have stronger binding to broadly neutralizing antibodies and reduced binding to non-neutralizing antibodies. The inventors further displayed the redesigned HCV E2 polypeptides on nanoparticles of various sizes. The resulting nanoparticle vaccine compositions also demonstrated substantial yield, high purity, and enhanced antigenicity. In addition, mice were immunized with the nanoparticle vaccine constructs, and longitudinal serum analysis confirmed the superior immunogenicity of the nanoparticle vaccines. Moreover, statistical analysis was performed to validate the in vivo data, providing a rigorous foundation for future comparison of different types of HCV vaccine candidates.

In accordance with these studies, the invention provides novel HCV immunogen polypeptides that are derived from the engineered or redesigned HCV E2 core polypeptides described herein. Also provided in the invention are HCV vaccine compositions containing a displaying platform, including a self-assembling nanoparticle, that displays one or more of the redesigned HCV E2 polypeptides. Therapeutic applications of the redesigned HCV E2 polypeptides and the related nanoparticle vaccine compositions, e.g., treating or preventing HCV infections, are also provided in the invention.

Unless otherwise specified herein, the vaccine immunogens of the invention, the encoding polynucleotides, expression vectors and host cells, as well as the related therapeutic applications, can all be generated or performed in accordance with the procedures exemplified herein or routinely practiced methods well known in the art. See, e.g., Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Sambrook et al., Molecular Cloning: A Laboratory Manual, Cold Spring Harbor Press, N.Y. (3rd ed., 2000); Brent et al., Current Protocols in Molecular Biology, John Wiley & Sons, Inc. (ringbou ed., 2003); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998). The following sections provide additional guidance for practicing the compositions and methods of the present invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1$^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press (4$^{th}$ ed., 2000). Further clarifications of some of these terms as they apply specifically to this invention are provided herein.

As used herein, the singular forms "a," "an," and "the," refer to both the singular as well as plural, unless the context clearly indicates otherwise. For example, "an Env-derived trimer" can refer to both single or plural Env-derived trimer molecules, and can be considered equivalent to the phrase "at least one Env-derived trimer."

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein. Unless otherwise noted, the term "vaccine immunogen" is used interchangeably with "protein antigen" or "immunogen polypeptide".

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Epitope refers to an antigenic determinant. These are particular chemical groups or peptide sequences on a molecule that are antigenic, such that they elicit a specific immune response, for example, an epitope is the region of an antigen to which B and/or T cells respond. Epitopes can be formed both from contiguous amino acids or noncontiguous amino acids juxtaposed by tertiary folding of a protein.

Effective amount of a vaccine or other agent that is sufficient to generate a desired response, such as reduce or eliminate a sign or symptom of a condition or disease, such as a viral infection. For instance, this can be the amount necessary to inhibit viral replication or to measurably alter outward symptoms of the viral infection. In general, this amount will be sufficient to measurably inhibit virus (for example, HCV) replication or infectivity. When administered to a subject, a dosage will generally be used that will achieve a target concentration that has been shown to be sufficient for in vitro inhibition of viral replication. In some embodiments, an "effective amount" is one that treats (including prophylaxis) one or more symptoms and/or underlying causes of any of a disorder or disease, for example to treat HCV infection. In some embodiments, an effective amount is a therapeutically effective amount. In some embodiments, an effective amount is an amount that prevents one or more signs or symptoms of a particular disease or condition from developing, such as one or more signs or symptoms associated with HCV infection.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of bacterial enzymes such as *B. stearothermophilus* dihydrolipoyl acyltransferase (E2p) and the amino acid sequences of HCV E2 glycoproteins are not normally found joined together via a peptide bond.

As used herein, "E1" refers to an envelope glycoprotein on hepatitis C virus. The E1 polypeptide is located in the HCV polyprotein immediately after the core protein at amino acid residues corresponding to residues 192-383 of the HCV genotype 1a, H77 isolate polyprotein.

As used herein, HCV envelope glycoprotein 2 (E2) refers to an envelope glycoprotein on hepatitis C virus. E2 is a type I transmembrane protein with an amino-terminal ectodomain connected to a carboxy-terminal transmembrane helix through an amphipathic, a-helical stem. The E2 polypeptide is located in the HCV polyprotein immediately after the E1 polypeptide at amino acid residues corresponding to residues 384-746 (SEQ ID NO:1) of the HCV genotype 1a, H77 isolate. See, e.g., Goffard et al., Biochimie 85, 295-301, 2003. Unless otherwise noted, reference to an E2 polypeptide herein also includes truncated forms thereof, such as soluble forms that are truncated at their C-terminus to remove the transmembrane domain, that retain a property, such as a binding property, and variants, such as those from different HCV isolates and quasispecies, including polypeptides that have at least 40%, 45%, 50%, 55%, 65%, 70%, 75%, 80%, 85%, 90%, 95%, 96%, 97%, 98%, 99% or more sequence identity to the E2 polypeptide from HCV genotype 1a, isolate H77, set forth in SEQ ID NO:1.

Unless otherwise noted, E2 polypeptides include synthetic molecules prepared by translation of nucleic acids, proteins generated by chemical synthesis, such as syntheses that include ligation of shorter polypeptides, through recombinant methods, proteins isolated from HCV-infected human and non-human tissue and cells, chimeric E2 polypeptides and modified forms thereof. E2 polypeptides also include fragments or portions of E2 that are of sufficient length or include appropriate regions to retain at least one property of a full-length E2 polypeptide, such as the ability to bind to anti-E2 antibodies. E2 polypeptides also include those that contain chemical or posttranslational modifications and those that do not contain chemical or posttranslational modifications. Such modifications include, but are not limited to, pegylation, albumination, glycosylation, farnysylation, carboxylation, hydroxylation, phosphorylation, and other polypeptide modifications known in the art.

As used herein, the HCV E2 ectodomain ($E2_{ECTO}$ or E2 ΔTM) refers to the soluble portion of the E2 polypeptide that is outside the viral membrane, i.e., the N-terminal portion of E2 protein that does not include the transmembrane helix. In the prototype H77 isolate, E2 ΔTM or $E2_{ECTO}$ consists of amino acids 384-717 (SEQ ID NO:2) and is stabilized by nine conserved disulfide bonds. It contains three variable regions including hypervariable region 1 (HVR1, a.a. 384-411), VR2 (a.a. 460-484), and VR3 (a.a. 570-580) and is covered with ~11 N-linked glycans. As used herein, the VR2 disordered region refers to a specific E2 fragment which spans VR2, and is bordered by two cysteine residues that form two disulfide bonds for anchoring to the back layer and the β-sandwich domain, respectively. In the H77 isolate, the VR2 disordered region corresponds to residues 452-494, and the two anchoring disulfide bonds are C452-C620 and C494-0564.

As used herein, reference to an amino acid position in any of the mature, processed HCV proteins, such as E2, is made with numbering relative to the full length HCV polypeptide, and not with reference to the mature polypeptide. Thus, for example, reference to amino acid position 425 in the E2 polypeptide from HCV genotype 1a, isolate H77 corresponds to position 42 of the mature E2 polypeptide set forth in SEQ ID NO:1.

As used herein, corresponding residues refers to residues that occur at aligned loci. Related or variant polypeptides are aligned by any method known to those of skill in the art. Such methods typically maximize matches, and include methods such as using manual alignments and by using the numerous alignment programs available (for example, BLASTP) and others known to those of skill in the art. By aligning the sequences of polypeptides, one skilled in the art can identify corresponding residues, using conserved and identical amino acid residues as guides. For example, by aligning the sequences of E2 polypeptides from different HCV isolates, one of skill in the art can identify corresponding residues, using conserved and identical amino acid residues as guides. Corresponding positions also can be based on structural alignments, for example by using computer simulated alignments of protein structure.

As used herein, the term "hepatitis C virus," "HCV," or "HCVs" includes different viral genotypes, subtypes, quasispecies and isolates. It includes any noncytopathic RNA virus that has a single and positive-stranded RNA genome belonging to the *Hepacivirus* genus of the Flaviviridae family. The term includes different isolates of HCV such as, without limitation, those having polyprotein sequences and accession numbers shown above, as well as any others in the NCBI database. Examples of different genotypes encompassed by this term include, without limitation, genotype 1, 2, 3, 4, 5 and 6, as described in Simmonds et al. (Hepatology 42:962-973, 2005). Reference to HCV also includes those of any additional genotypes that are established. Examples of different subtypes include, without limitation, 1a, 1b, 1c, 2a, 2b, 2c, 2i, 2k, 3a, 3b, 3k, 4a, 4d, 4f, 5a, 6a, 6b, 6c, 6d, 6e, 6f, 6g, 6h, 6i, 6j, 6k, 6l, 6m, 6n, 6o, 6q, 6p and 6t. The term also includes cell culture HCVs (HCVcc) and pseudotype HCVs (HCVpp), as well as HCV quasispecies. Various HCVs are described by Simmonds P. in *Genetic diversity and evolution of hepatitis C virus—15 years on, J Gen Virol* 85:3173-3188 (2004) and Simmonds et al. in *Consensus proposals for a unified system of nomenclature of hepatitis C virus genotypes, Hepatology* 42:962-973 (2005). HCV nucleotide sequences are known in the art. For example, see Viral Bioinfomatics Research Center (hcvdb.org) and the Hepatitis C Virus database (hcv.lanl.gov).

Immunogen as used herein refers to a protein or a portion thereof that is capable of inducing an immune response in a mammal, such as a mammal infected or at risk of infection with a pathogen. Administration of an immunogen can lead to protective immunity and/or proactive immunity against a pathogen of interest.

Immune response refers to a response of a cell of the immune system, such as a B cell, T cell, or monocyte, to a stimulus. In some embodiment, the response is specific for a particular antigen (an "antigen-specific response"). In some embodiments, an immune response is a T cell response, such as a CD4+ response or a CD8+ response. In some other embodiments, the response is a B cell response, and results in the production of specific antibodies.

Immunogenic composition refers to a composition comprising an immunogenic polypeptide that induces a measurable CTL response against virus expressing the immunogenic polypeptide, or induces a measurable B cell response (such as production of antibodies) against the immunogenic polypeptide.

Sequence identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The term "subject" refers to any animal classified as a mammal, e.g., human and non-human mammals. Examples of non-human animals include dogs, cats, cattle, horses, sheep, pigs, goats, rabbits, and etc. Unless otherwise noted, the terms "patient" or "subject" are used herein interchangeably. Preferably, the subject is human.

The term "treating" or "alleviating" includes the administration of compounds or agents to a subject to prevent or delay the onset of the symptoms, complications, or biochemical indicia of a disease (e.g., an HCV infection), alleviating the symptoms or arresting or inhibiting further development of the disease, condition, or disorder. Subjects in need of treatment include those already suffering from the disease or disorder as well as those being at risk of developing the disorder. Treatment may be prophylactic (to prevent or delay the onset of the disease, or to prevent the manifestation of clinical or subclinical symptoms thereof) or therapeutic suppression or alleviation of symptoms after the manifestation of the disease.

Vaccine refers to a pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In some embodiments of the invention, vaccines or vaccine immunogens or vaccine compositions are expressed from fusion constructs and self-assemble into nanoparticles displaying an immunogen polypeptide or protein on the surface.

Virus-like particle (VLP) refers to a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) Biophys. J. 60:1445-1456; and Hagensee et al. (1994) J. Virol. 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

A self-assembling nanoparticle refers to a ball-shape protein shell with a diameter of tens of nanometers and well-defined surface gemoetry that is formed by identical copies of a non-viral protein capable of automatically assembling into a nanoparticle with a similar appearance to VLPs. Known examples include ferritin (FR), which is conserved across species and forms a 24-mer, as well as *B. stearothermophilus* dihydrolipoyl acyltransferase (E2p), *Aquifex aeolicus* lumazine synthase (LS), and *Thermotoga maritima* encapsulin, which all form 60-mers. Self-assembling nanoparticles can form spontaneously upon recombinant expression of the protein in an appropriate expression system. Methods for nanoparticle production, detection, and characterization can be conducted using the same techniques developed for VLPs.

III. Redesigned HCV E2 Core Immunogenic Polypeptides

The invention provides engineered or redesigned HCV E2 core polypeptides or proteins for producing HCV vaccines. E2 is a type I transmembrane protein with an amino-terminal ectodomain connected to a carboxy-terminal transmembrane helix through an amphipathic, α-helical stem. The E2 polypeptide is located in the HCV polyprotein immediately after the E1 polypeptide at amino acid residues corresponding to residues 384-746 of the HCV genotype 1a, H77 isolate. See, e.g., Goffard et al., Biochimie 85, 295-301, 2003. E2 is highly modified post-translationally with several (9-11) N-linked glycosylation sites and 20 cysteine residues that are conserved across all genotypes. Unless otherwise noted, amino acid residue numbering of HCV genotype 1a, H77 isolate is used herein as the reference.

E2 core refers to a portion of E2 that forms a 3-dimensional structure that is recognized by a broadly neutralizing antibody, AR3C Fab. See, e.g., Law et al., Nat. Med. 2008; 14:25, 2008. The E2 core has a compact, globular domain structure, consisting mostly of β-strands and random coil with two small a-helices. The strands are arranged in two, perpendicular sheets (A and B), which are held together by an extensive hydrophobic core and disulfide bonds. The E2 core contains a central immunoglobulin (Ig)-like β-sandwich with front and back layers. As used herein, an E2 core polypeptide refers to an engineered polypeptide sequence that includes E2 residues or fragments that correspond to the key structural elements of E2 core in its 3-dimensional structure of E2. A prototype E2 core polypeptide, E2c (SEQ ID NO:3), is derived from E2 ΔTM of the H77 isolate. It consists of E2 amino acids 412-459, a GSSG linker replacing residues 460-485 of E2, and amino acids 486-645, with both the stalk region and the transmembrane (TM) region deleted. Relative to E2 sequence, E2c additionally contains mutations N448D and N576D. A further modified E2 core polypeptide, E2c3 (SEQ ID NO:4), is derived from E2c. Relative to E2c, the E2c3 polypeptide additionally contains a "GGPTDG" (SEQ ID NO:43) linker replacing E2 residues 569-597. Thus, it consists of amino acids 412-459, the "GSSG" linker, amino acids 486-568, the "GGPTDG" (SEQ ID NO:43) linker, and amino acids 598-645. Also, E2c3 only harbors the N448D substitution, with the N576D substitution being removed as a result of residues 569-597 being replaced by the GGPTDG (SEQ ID NO:43) linker. See, e.g., Kong et al., Science. 342:1090-1094, 2013; and Kong et al., Proc. Natl. Acad. Sci. U.S.A. 113, 12768-12773, 2016.

Unless otherwise noted, the amino acid residue numbering of E2 or derivative thereof (e.g., E2 ΔTM and E2 core), as well as the various redesigned HCV core polypeptides of the invention, is based on HCV genotype 1a, H77 isolate. Due to substantial sequence conservation among the E2 proteins from different HCV genotypes, corresponding amino acid residues bordering the various domains, regions and loops of an E2 protein from any other HCV genotype and isolate can be readily determined (e.g., by sequence alignment) or otherwise known in the art. For example, while E2 core of the H77 isolate spans residues 412-645, the E2 core of HCV genotype 2a, isolate J6 is comprised of residues spanning 412-645 based on the H77 numbering system (or 412-649 in the actual J6 polypeptide sequence). See, e.g., Kong et al., Science. 342:1090-1094, 2013; and Khan et al., Nature 509:381-384, 2014.

In general, the redesigned HCV E2 polypeptides of the invention contain one or more modifications in the VR2 disordered region and the β-sandwich loop. The original VR2 disordered region contains 43 residues, corresponding to residues 452-494 in the H77 isolate, CPERLASCRRLTDFAQGWGPISYANGSGLDERPYCWHYPPRPC (SEQ ID NO:5). The corresponding region in the engineered E2c proteins known in the art, E2c and E2c3, contain a sequence of 21 residues, CPERLASCGSSGCWHYPPRPC (SEQ ID NO:6). Typically, the redesigned HCV E2 polypeptides of the invention contain a further shortened VR2 disordered region (tVR2) relative to that of the engineered E2c proteins known in the art, E2c and E2c3. In various embodiments, the further shortened VR2 disordered region ("tVR2") in the redesigned HCV E2 polypeptides contains less than about 20, 19, 18, 17, 16 or less residues. In some preferred embodiments, the tVR2 contains less than about 15, 14, 13, 12 or less residues. As shown in the exemplified tVR2 sequence of redesigned HCV E2 polypeptide E2mc3, CPERASGHYPRPC (SEQ ID NO:10), the further shortening of the VR2 disordered region of E2c and E2c3 involves deletions of various residues in SEQ ID NO:6. In some embodiments, the tVR2 of the redesigned HCV E2 polypeptides of the invention can have an amino acid sequence set forth in C(X)nHYPRPC (SEQ ID NO:7), wherein X is any amino acid residue, and n is between about 3 to about 10. In some of these embodiments, the tVR2 contains 13 or 12 residues as set forth in CXXXXXXHYPRPC (SEQ ID NO:8) or CXXXXXHYPRPC (SEQ ID NO:9), wherein X is any amino acid residue. Importantly, it was observed that the prior art E2 polypeptide such as E2c3 could not be displayed on nanoparticles with meaningful expression. In contrast, further modification of the VR2 disordered region in the redesigned HCV E2 polypeptides of the invention enables satisfactory nanoparticle display of the polypeptides, as exemplified herein.

In addition to the shortened length, modification of the VR2 disordered region can additionally involve optimization of the sequence to further stabilize the HCV E2 polypeptides. Optimization of the tVR2 sequence can be performed using ensemble-based de novo protein design as described in, e.g., Kong et al., Nat. Commun. 7:12040, 2016. Specific guidance for optimizing tVR2 sequence by selecting random sequences, performing simulated annealing and identifying lowest-energy sequences, is also provided in the Examples herein. In some of the redesigned HCV E2 polypeptides of the invention, the tVR2 sequence is derived from optimization of the sequence as set forth in any one of SEQ ID NOs:7-9. As exemplification with redesigned HCV E2 polypeptides set forth in SEQ ID NOs:27-38, the optimized tVR2 sequence can be any of SEQ ID NOs:65-74, a substantially identical sequence or a conservatively substituted variant thereof.

Additionally or alternatively to the modified VR2 disordered region, the redesigned HCV E2 polypeptides of the invention also contain a modification in the β-sandwich domain. As shown in FIG. 1A, the β-sandwich domain is composed of two parts, residues 485-518 and 536-569, in the linear sequence HCV E2. These two parts interact with each other and form the β-sandwich domain in the 3-dimensional structure. This β sandwich domain is composed of 7 β strands, where the CD81 binding loop (residues 519-535) is connecting the two parts of the domain between β strand 5 and 6. Modification of the β-sandwich domain in the redesigned HCV E2 polypeptides of the invention relates to a β-sandwich loop, H77 isolate E2 residues 540-550 (NNTRPPLGNWF; SEQ ID NO:21), that connects β strand 6 to 7 in the β-sandwich domain. This modification is intended to disrupt the binding site on E2 that is recognized by non-neutralizing antibodies, thereby focusing immune response to broadly neutralizing antibodies. The modification involves deletion of one or more residues in the β-sandwich loop sequence that form the tip in the 3-D structure. In the H77 isolate, these are residues 543-546 (RPPL; SEQ ID NO:22). Optionally, one or more of the adjacent residues may also be deleted. Thus, in various embodiments, the modification of the β-sandwich loop can entail deletion of any combination of 1, 2, 3, 4, 5, or 6 residues from residues 542-547 (TRPPLG; SEQ ID NO:23). In some embodiments, the β-sandwich loop modification includes deletion of residues PP, RPP, PPL, RPPL (SEQ ID NO:22), TRPPL (SEQ ID NO:24), RPPLG (SEQ ID NO:25) or TRPPLG (SEQ ID NO:23). In some preferred embodiments, the modification involves deletion of residues RPPL (SEQ ID NO:22) from the β-sandwich loop.

Preferably, the redesigned HCV E2 core polypeptides contain both modifications of the VR2 disordered region and the β-sandwich loop as described above. Some specific examples of redesigned HCV E2 core polypeptides containing such modifications are set forth in SEQ ID NOs:26-38. As exemplified herein, while being derived from different HCV isolates and genotypes, these redesigned HCV E2 core polypeptides all demonstrated substantially improved yield and purity, as well as satisfactory immunogenic activities. In addition to these specific polypeptides, redesigned HCV E2 polypeptides of the invention also encompass polypeptides having an amino acid sequence that is substantially identical to one of these sequences, including conservatively modified variant sequences. In various embodiments, the redesigned HCV E2 core polypeptides of the invention can have an amino acid sequence that is identical to any of SEQ ID NOs:26-38, except for one or more amino acid residue substitutions of non-conserved residues among different HCV isolates or genotypes, or substitutions in the non-conserved region or motif of the E2 sequence of different HCV isolates or genotypes.

As exemplified herein with isolate H77 (genotype 1a) and isolate HK6a (genotype 6a), E2 sequences from various HCV strains can all be readily employed to generate HCV immunogen polypeptides in accordance with the redesign strategy described herein. HCV isolates have been grouped into seven genotypes and a number of subtypes, which have different geographical distributions. E2 sequences of many of these isolates are already known. For example, HCV related sequence information can be obtained from the Hepatitis C Virus Databases maintained by the National Institute of Allergy and Infectious Diseases (NIAID). While there is a considerable degree of variability among E2 sequences of different HCV isolates, a certain number of conserved motifs or neutralizing epitopes have been identified in the E2 sequences. In redesigning E2 core polypeptides with a given HCV E2 sequence in accordance with the strategy described herein, one can readily determine the appropriate residues for modifications via sequence alignment and also considering the conserved motifs known in the art. See, e.g., Simmonds et al., Hepatology 42:962-973, 2005; Wang et al., Viruses 3:2127-2145, 2011; and Krey et al., PLoS Pathog. 6:e1000762, 2010; Bhattarai et al., PLoS Pathog. 11: e1005183, 2015; and Kachko et al., Vaccine 30:69-77, 2011. As exemplified herein with the HK6a isolate, redesigned HCV E2 polypeptides from other isolates can be obtained by directly adopting the H77 sequence designs without further modification. This includes replacing the VR2 disordered region with the same optimized tVR2 sequence identified for the H77 isolate and deleting the corresponding residues in the tip of the β-sandwich loop as in the redesigned H77 sequences exemplified herein.

As detailed below, the resigned HCV E2 polypeptides may be conjugated to a presenting platform (e.g., nanoparticles or VLPs) via various means. Preferably, the conjugation is achieved via covalent linkage, e.g., protein fusions or insertions. In some preferred embodiments, the protein sequence is fused with the presenting platform sequence via a linker sequence. In various embodiments, other modifications can also be made to the redesigned E2 polypeptides or the conjugating partner in order to improve stability or antigenicity.

The various redesigned HCV E2 polypeptides of the invention can be obtained or generated in accordance with the protocols exemplified herein or methods well known in the art. See, e.g., Sambrook et al., Molecular Cloning: A Laboratory Manual, Cold Spring Harbor Press, N.Y., (3$^{rd}$ ed., 2000); and Brent et al., Current Protocols in Molecular Biology, John Wiley & Sons, Inc. (ringbou ed., 2003). Upon recombinant expression (e.g., in HEK293 F cells as detailed herein), the proteins can be purified by any of the routinely practiced procedures. See, e.g., *Guide to Protein Purification*, Ed. Deutscher, Meth. Enzymol. 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Once purified, antigenicity and other properties of the redesigned HCV E2 polypeptides can also be readily examined with standard methods, e.g., antigenic profiling using known bNAbs and non-Nabs, differential scanning calorimetry (DSC), electron microscopy, binding analysis via ELISA, Biolayer Interferometry (BLI), Surface Plasmon Resonance (SPR), and co-crystallography analysis as exemplified herein.

IV. Scaffolded HCV E2 Vaccine Compositions

Other than the engineered or redesigned HCV E2 polypeptides described above, the invention also provides HCV E2 polypeptide based vaccine compositions that contain a heterologous scaffold that presents or incorporates a redesigned HCV E2 protein. Any heterologous scaffold can be used to present the redesigned HCV E2 polypeptide in the construction of the vaccines of the invention. These include nanoparticles, virus-like particles, protein carriers (e.g., immunoglobulin chains or domains such as Fc, KLH, BSA, tetanus toxoid, and diphtheria toxoid), as well as various chemical scaffolds. In some embodiments, a virus-like particle (VLP) such as bacteriophage $Q_\beta$ VLP and nanoparticles can be used. In some preferred embodiments, the heterologous scaffold for presenting or displaying the redesigned HCV E2 polypeptide is a self-assembling nanoparticle. Various nanoparticle platforms can be employed in generating the vaccine compositions of the invention. In general, the nanoparticles employed in the invention need to be formed by multiple copies of a single subunit. The nanoparticles are typically ball-like shaped, and/or have rotational symmetry (e.g., with 3-fold and 5-fold axes), e.g., with an icosahedral structure exemplified herein. Additionally or alternatively, the amino-terminus of the particle subunit has to be exposed and in close proximity to the 3-fold axis, and the spacing of three amino-termini has to closely match the spacing of the carboxyl-termini of the HCV E2 polypeptides. In some preferred embodiments, the immunogens comprise self-assembling nanoparticles with a diameter of about 20 nm or less (usually assembled from 12, 24, or 60 subunits) and 3-fold axes on the particle surface.

In some preferred embodiments, the immunogen protein or polypeptide (e.g., an HCV E2 protein) is presented on self-assembling nanoparticles such as self-assembling nanoparticles derived from E2p, I3-01 and ferritin (FR) as exemplified herein. E2p is a redesigned variant of dihydrolipoyl acyltransferase from *Bacillus stearothermophilus* that has been shown to self-assemble into thermostable 60-meric nanoparticle. See, e.g., He et al., *Nat. Commun.* 7:12041, 2016 Similarly, I3-01 is an engineered protein that can self-assemble into hyperstable nanoparticles. See, e.g., Hsia et al., Nature 535, 136-139, 2016. Sequences of the subunits of these proteins are known in the art. See, e.g., WO2017/

192434. Ferritin is a globular protein found in all animals, bacteria, and plants. The globular form of ferritin is made up of monomeric subunit proteins (also referred to as monomeric ferritin subunits), which are polypeptides having a molecule weight of approximately 17-20 kDa. Amino acid sequences of E2p, I3-01 and ferritin nanoparticle subunits as exemplified herein are shown in SEQ ID NOs:39-41, respectively. Relative to the original sequence, E2p sequence shown in SEQ ID NO:39 contains an Ala substitution at residue 92 as underscored in the sequence below. In various embodiments, the HCV E2 nanoparticle vaccines of the invention can employ any of these known nanoparticles, as well as their conservatively modified variants or variants with substantially identical (e.g., at least 90%, 95% or 99% identical) sequences.

E2p subunit sequence
(SEQ ID NO: 39)
AAAKPATTEGEFPETREKMSGIRRAIAKAMVHSKHTAPHVTLMDEADVTK

LVAHRKKFKAIAAEKGIKLTFLPYVVKALVSALREYPVLNTAIDDETEEI

IQKHYYNIGIAADTDRGLLVPVIKHADRKPIFALAQEINELAEKARDGKL

TPGEMKGASCTITNIGSAGGQWFTPVINHPEVAILGIGRIAEKPIVRDGE

IVAAPMLALSLSFDHRMIDGATAQKALNHIKRLLSDPELLLM

I3-01 subunit sequence
(SEQ ID NO: 40)
MKMEELFKKHKIVAVLRANSVEEAKKKALAVFLGGVHLIEITFTVPDADT

VIKELSFLKEMGAIIGAGTVTSVEQCRKAVESGAEFIVSPHLDEEISQFC

KEKGVFYMPGVMTPTELVKAMKLGHTILKLFPGEVVGPQFVKAMKGPFPN

VKFVPTGGVNLDNVCEWFKAGVLAVGVGSALVKGTPVEVAEKAKAFVEKI

RGCTE

Ferritin sequence
(SEQ ID NO: 41)
MLSKDIIKLLNEQVNKEMNSSNLYMSMSSWCYTHSLDGAGLFLFDHAAEE

YEHAKKLIIFLNENNVPVQLTSISAPEHKFEGLTQIFQKAYEHEQHISES

INNIVDHAIKSKDHATFNFLQWYVAEQHEEEVLFKDILDKIELIGNENHG

LYLADQYVKGIAKSRKS

In addition to these exemplified nanoparticle sequences, many other nanoparticles or VLPs known in the art may also be used in the practice of the invention. These include, e.g., *Aquifex aeolicus* lumazine synthase, *Thermotoga Maritima* encapsulin, *Myxococcus xanthus* encapsulin, bacteriophage Qbeta virus particle, Flock House Virus (FHV) particle, ORSAY virus particle, and infectious bursal disease virus (IBDV) particle. Other molecules that may be used as the presenting platform of the nanoparticle vaccines of the invention include, e.g., molecules with the following PDB IDs: 1JIG (12-mer Dlp-2 from *Bacillus anthraces*), 1UVH (12-mer DPS from *Mycobacterium smegmatis*), 2YGD (24-mer eye lens chaperone αB-crystallin), 3CS0 (24-mer DegP24), 3MH6 and 3MH7 (24-mer HtrA proteases), 3PV2 (12-mer HtrA homolog DegQ WT), 4A8C (12-mer DegQ from *E. coli.*), 4A9G (24-mer DegQ from *E. Coli.*), 4EVE (12-mer HP-NAP from *Helicobacter pylori* strain YS29), and 4GQU (24-mer HisB from *Mycobacterium tuberculosis*).

Some HCV E2 nanoparticle vaccine compositions can additionally contain other structural components that function to further enhance stability and antigenicity of the displayed immunogen. In some embodiments, a locking protein domain can be inserted into the nanoparticle construct, e.g., by covalently fused to the C-terminus of the nanoparticle subunit. The locking domain can be any dimeric protein that is capable of forming an interface through specific interactions such as hydrophobic (van der Waals) contacts, hydrogen bonds, and/or salt bridges. General guidance on selecting locking domains and specific examples are described in the art, e.g., PCT2019/036917. In some embodiments, HCV E2 nanoparticle vaccines of the invention can also contain a T-cell epitope to promote robust T-cell responses and to steer B cell development towards bNAbs. The T-cell epitope can be located at any position in relation to the other structural components as long as it does not impact presentation of the immunogen polypeptides on the nanoparticle surface. Any T-cell epitope sequences or peptides known in the art may be employed in the practice of the present invention. They include any polypeptide sequence that contain MHC class-II epitopes and can effectively activate CD4+ and CD8+ T cells upon immunization, e.g., T-helper epitope that activates CD4+T helper cells. See, e.g., Alexander et al., Immunity 1, 751-761, 1994; Ahlers et al., J. Clin. Invest. 108:1677-1685, 2001; Fraser et al., Vaccine 32, 2896-2903, 2014; De Groot et al., Immunol. Cell Biol. 8:255-269, 2002; and Gene Ther. 21: 225-232, 2014. In some embodiments, the HCV E2 nanoparticle vaccines of the invention also contain a neck region or domain to facilitate display of the immunogen on the surface of nanoparticles. The neck region can be a three-helix bundle derived from a viral protein, e.g., Hendra virus domain (PDB ID: 4HEO) or Measles virus domain (PDB ID: 1OKS). It is typically inserted between the immunogen and the nanoparticle subunit, thereby elevating the immunogen polypeptide from the nanoparticle surface. In still some embodiments, the nanoparticle vaccines of the invention can contain a protein domain that serves to stabilize the immunogen polypeptide. For example, the protein domain can be the C-terminal trimerization motif of T4 fibritin (foldon) that is well known in the art. This foldon domain constitutes the C-terminal 30 amino acid residues of the trimeric protein fibritin from bacteriophage T4, and functions in promoting folding and trimerization of fibritin. See, e.g., Papanikolopoulou et al., J. Biol. Chem. 279: 8991-8998, 2004; and Guthe et al., J. Mol. Biol. 337: 905-915, 2004.

The scaffolded HCV E2 vaccine compositions of the invention can be constructed in accordance with standard recombinant techniques and the methods described herein (e.g., Examples 4 and 8) and/or other methods that have been described in the art, e.g., He et al., Nat. Comm. 7, 12041, 2016; Kong et al., Nat. Comm. 7, 12040, 2016; and He et al., Sci Adv. 4(11):eaau6769, 2018. In various embodiments, nanoparticle displaying any of the redesigned HCV E2 polypeptides can be constructed by fusing the E2 polypeptide to the subunit of the nanoparticle (e.g., E2p subunit). Preferably, C-terminus of the HCV E2 polypeptide is fused to the N-terminus of the nanoparticle subunit. In some embodiments, a short peptide linked can be used to connect the E2 polypeptide and the nanoparticle, e.g., the 10GS linker (GGGGSGGGGS) (SEQ ID NO:42) exemplified herein. Once constructed, the antigeniciy and structural integrity of the nanoparticle displayed HCV E2 polypeptides can be readily analyzed via standard assays, e.g., antibody binding assays, biolayer interferometry, and negative-stain electron microscopy (EM). As exemplified herein, the various fusion molecules can all self-assemble into nanoparticles that display immunogenic epitopes of the HCV E2 polypeptides. By eliciting a robust neutralizing antibody response, these nanoparticles are useful for vaccinating individuals against a broad range of HCV viruses.

V. Polynucleotides and Expression Constructs

The redesigned HCV E2 polypeptides and the nanoparticle vaccine compositions of the invention are typically produced by first generating expression constructs (i.e., expression vectors) that contain operably linked coding sequences of the various structural components described herein. Accordingly, in some related aspects, the invention provides substantially purified polynucleotides (DNA or RNA) that encode the redesigned HCV E2 polypeptides and nanoparticle displayed HCV E2 immunogens as described herein, as well as expression vectors that harbor such polynucleotides and host cells for producing the HCV E2 immunogen polypeptides and the vaccine compositions (e.g., HEK293 F cells and ExpiCHO cells exemplified herein). The fusion polypeptides encoded by the polynucleotides or expressed from the vectors are also included in the invention.

The polynucleotides and related vectors can be readily generated with standard molecular biology techniques or the protocols exemplified herein. For example, general protocols for cloning, transfecting, transient gene expression and obtaining stable transfected cell lines are described in the art, e.g., Sambrook et al., Molecular Cloning: A Laboratory Manual, Cold Spring Harbor Press, N.Y., ($3^{rd}$ ed., 2000); and Brent et al., Current Protocols in Molecular Biology, John Wiley & Sons, Inc. (ringbou edition, 2003). Introducing mutations to a polynucleotide sequence by PCR can be performed as described in, e.g., *PCR Technology: Principles and Applications for DNA Amplification*, H. A. Erlich (Ed.), Freeman Press, NY, NY, 1992; *PCR Protocols: A Guide to Methods and Applications*, Innis et al. (Ed.), Academic Press, San Diego, Calif., 1990; Manila et al., Nucleic Acids Res. 19:967, 1991; and Eckert et al., PCR Methods and Applications 1:17, 1991.

The selection of a particular vector depends upon the intended use of the fusion polypeptides. For example, the selected vector must be capable of driving expression of the fusion polypeptide in the desired cell type, whether that cell type be prokaryotic or eukaryotic. Many vectors contain sequences allowing both prokaryotic vector replication and eukaryotic expression of operably linked gene sequences. Vectors useful for the invention may be autonomously replicating, that is, the vector exists extrachromosomally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors and in stably transfected cell lines. Both viral-based and nonviral expression vectors can be used to produce the immunogens in a mammalian host cell. Non-viral vectors and systems include plasmids, episomal vectors, typically with an expression cassette for expressing a protein or RNA, and human artificial chromosomes (see, e.g., Harrington et al., Nat. Genet. 15:345, 1997). Useful viral vectors include vectors based on lentiviruses or other retroviruses, adenoviruses, adeno associated viruses, cytomegalovirus, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

Depending on the specific vector used for expressing the fusion polypeptide, various known cells or cell lines can be employed in the practice of the invention. The host cell can be any cell into which recombinant vectors carrying a fusion of the invention may be introduced and wherein the vectors are permitted to drive the expression of the fusion polypeptide is useful for the invention. It may be prokaryotic, such as any of a number of bacterial strains, or may be eukaryotic, such as yeast or other fungal cells, insect or amphibian cells, or mammalian cells including, for example, rodent, simian or human cells. Cells expressing the fusion polypeptides of the invention may be primary cultured cells or may be an established cell line. Thus, in addition to the cell lines exemplified herein (e.g., CHO cells), a number of other host cell lines capable well known in the art may also be used in the practice of the invention. These include, e.g., various Cos cell lines, HeLa cells, HEK293, AtT20, BV2, and N18 cells, myeloma cell lines, transformed B-cells and hybridomas.

The use of mammalian tissue cell culture to express polypeptides is discussed generally in, e.g., Winnacker, *From Genes to Clones*, VCH Publishers, N.Y., N.Y., 1987. The fusion polypeptide-expressing vectors may be introduced to the selected host cells by any of a number of suitable methods known to those skilled in the art. For the introduction of fusion polypeptide-encoding vectors to mammalian cells, the method used will depend upon the form of the vector. For plasmid vectors, DNA encoding the fusion polypeptide sequences may be introduced by any of a number of transfection methods, including, for example, lipid-mediated transfection ("lipofection"), DEAE-dextran-mediated transfection, electroporation or calcium phosphate precipitation. These methods are detailed, for example, in Brent et al., supra. Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, Clontech, Glen Research, Life Technologies, JBL Scientific, MBI Fermentas, PanVera, Promega, Quantum Biotechnologies, Sigma-Aldrich, and Wako Chemicals USA.

For long-term, high-yield production of recombinant fusion polypeptides, stable expression is preferred. Rather than using expression vectors which contain viral origins of replication, host cells can be transformed with the fusion polypeptide-encoding sequences controlled by appropriate expression control elements (e.g., promoter, enhancer, sequences, transcription terminators, polyadenylation sites, etc.), and selectable markers. The selectable marker in the recombinant vector confers resistance to the selection and allows cells to stably integrate the vector into their chromosomes. Commonly used selectable markers include neo, which confers resistance to the aminoglycoside G-418 (Colberre-Garapin, et al., J. Mol. Biol., 150:1, 1981); and hygro, which confers resistance to hygromycin (Santerre et al., Gene, 30: 147, 1984). Through appropriate selections, the transfected cells can contain integrated copies of the fusion polypeptide encoding sequence.

VI. Pharmaceutical Compositions and Therapeutic Applications

The invention provides pharmaceutical or immunogenic compositions and related methods of using the redesigned HCV E2 polypeptides and nanoparticles displaying the polypeptides as described herein for preventing and treating HCV infections. In some embodiments, a redesigned HCV E2 polypeptide or a nanoparticle displaying the polypeptide is included in a pharmaceutical composition. The pharmaceutical composition can be either a therapeutic formulation or a prophylactic formulation. Typically, the composition additionally includes one or more pharmaceutically acceptable vehicles and, optionally, other therapeutic ingredients (for example, antibiotics or antiviral drugs). Various pharmaceutically acceptable additives can also be used in the compositions.

Some of the pharmaceutical compositions of the invention are vaccines. For vaccine compositions, appropriate adjuvants can be additionally included. Examples of suitable adjuvants include, e.g., aluminum hydroxide, lecithin, Freund's adjuvant, MPL™ and IL-12. In some embodiments, the resigned HCV E2 polypeptides disclosed herein can be formulated as a controlled-release or time-release formulation. This can be achieved in a composition that contains a slow release polymer or via a microencapsulated delivery system or bioadhesive gel. The various pharmaceutical compositions can be prepared in accordance with standard procedures well known in the art. See, e.g., Remington's Pharmaceutical Sciences, 19.sup.th Ed., Mack Publishing Company, Easton, Pa., 1995; Sustained and Controlled Release Drug Delivery Systems, J. R. Robinson, ed., Marcel Dekker, Inc., New York, 1978); U.S. Pat. Nos. 4,652,441 and 4,917,893; 4,677,191 and 4,728,721; and 4,675,189.

Therapeutic methods of the invention involve administering a redesigned HCV E2 polypeptide of the invention or a pharmaceutical composition containing the polypeptide to a subject having or at risk of developing HCV infection. In some embodiments, a pharmaceutical compositions of the invention is employed in therapeutic or prophylactic applications for treating HCV infection or eliciting an protective immune response against HCV in a subject. For example, the composition can be administered to a subject to induce an immune response to HCV, e.g., to induce production of broadly neutralizing antibodies to HCV. For subjects at risk of developing an HCV infection, a vaccine composition of the invention can be administered to provide prophylactic protection against viral infection. Depending on the specific subject and conditions, the pharmaceutical compositions of the invention can be administered to subjects by a variety of administration modes known to the person of ordinary skill in the art, for example, intramuscular, subcutaneous, intravenous, intra-arterial, intra-articular, intraperitoneal, or parenteral routes. In general, the pharmaceutical composition is administered to a subject in need of such treatment for a time and under conditions sufficient to prevent, inhibit, and/or ameliorate a selected disease or condition or one or more symptom(s) thereof. Symptoms of HCV exposure or infection include, e.g., inflammation of the liver, decreased appetite, fatigue, abdominal pain, jaundice, flu-like symptoms, itching, muscle pain, joint pain, intermittent low-grade fevers, sleep disturbances, nausea, dyspepsia, cognitive changes, depression headaches and mood changes.

Typically, the immunogenic composition of the invention is administered in an amount sufficient to induce an immune response against HCV. For therapeutic applications, the compositions should contain a therapeutically effective amount of a redesigned HCV E2 polypeptide or nanoparticle vaccine composition described herein. For prophylactic applications, the compositions should contain a prophylactically effective amount of the HCV E2 polypeptide or a nanoparticle displaying the polypeptide. The appropriate amount of the polypeptide immunogen or the nanoparticle composition can be determined based on the specific disease or condition to be treated or prevented, severity, age of the subject, and other personal attributes of the specific subject (e.g., the general state of the subject's health and the robustness of the subject's immune system). Determination of effective dosages is additionally guided with animal model studies followed up by human clinical trials and is guided by administration protocols that significantly reduce the occurrence or severity of targeted disease symptoms or conditions in the subject.

For prophylactic applications, the immunogenic composition is provided in advance of any symptom, for example in advance of infection. The prophylactic administration of the immunogenic compositions serves to prevent or ameliorate any subsequent infection. Thus, in some embodiments, a subject to be treated is one who has, or is at risk for developing, an HCV infection, for example because of exposure or the possibility of exposure to HCV. Following administration of a therapeutically effective amount of the disclosed therapeutic compositions, the subject can be monitored for HCV infection, symptoms associated with HCV infection, or both.

For therapeutic applications, the immunogenic composition is provided at or after the onset of a symptom of disease or infection, for example after development of a symptom of HCV infection, or after diagnosis of HCV infection. The immunogenic composition can thus be provided prior to the anticipated exposure to HCV virus so as to attenuate the anticipated severity, duration or extent of an infection and/or associated disease symptoms, after exposure or suspected exposure to the virus, or after the actual initiation of an infection.

The pharmaceutical composition of the invention can be combined with other agents known in the art for treating or preventing HCV infections. These include, e.g., (1) Daclatasvir, (2) Elbasvir and grazoprevir, (3) Glecaprevir and pibrentasvir, (4) Ledipasvir and sofosbuvir, (5) Ombitasvir, paritaprevir, and ritonavir, (6) Simeprevir (Olysio) and sofosbuvir (Sovaldi), (7) Sofosbuvir and velpatasvir (Epclusa), and (8) Sofosbuvir, velpatasvir, and voxilaprevir (Vosevi). See, e.g., Kish et al., P T. 42:316-329, 2017; and Dahiya et al., BCMJ 61:72-77, 2019. Administration of the pharmaceutical compositions and the known anti-HCV agents can be either concurrently or sequentially.

Pharmaceutical compositions containing a redesigned HCV E2 polypeptide or nanoparticle vaccine of the invention can be provided as components of a kit. Optionally, such a kit includes additional components including packaging, instructions and various other reagents, such as buffers, substrates, antibodies or ligands, such as control antibodies or ligands, and detection reagents. An optional instruction sheet can be additionally provided in the kits.

EXAMPLES

The following examples are offered to illustrate, but not to limit the present invention.

Example 1 Structure-Based Optimization of HCV Envelope Glycoprotein E2 Core

Figure 6A:
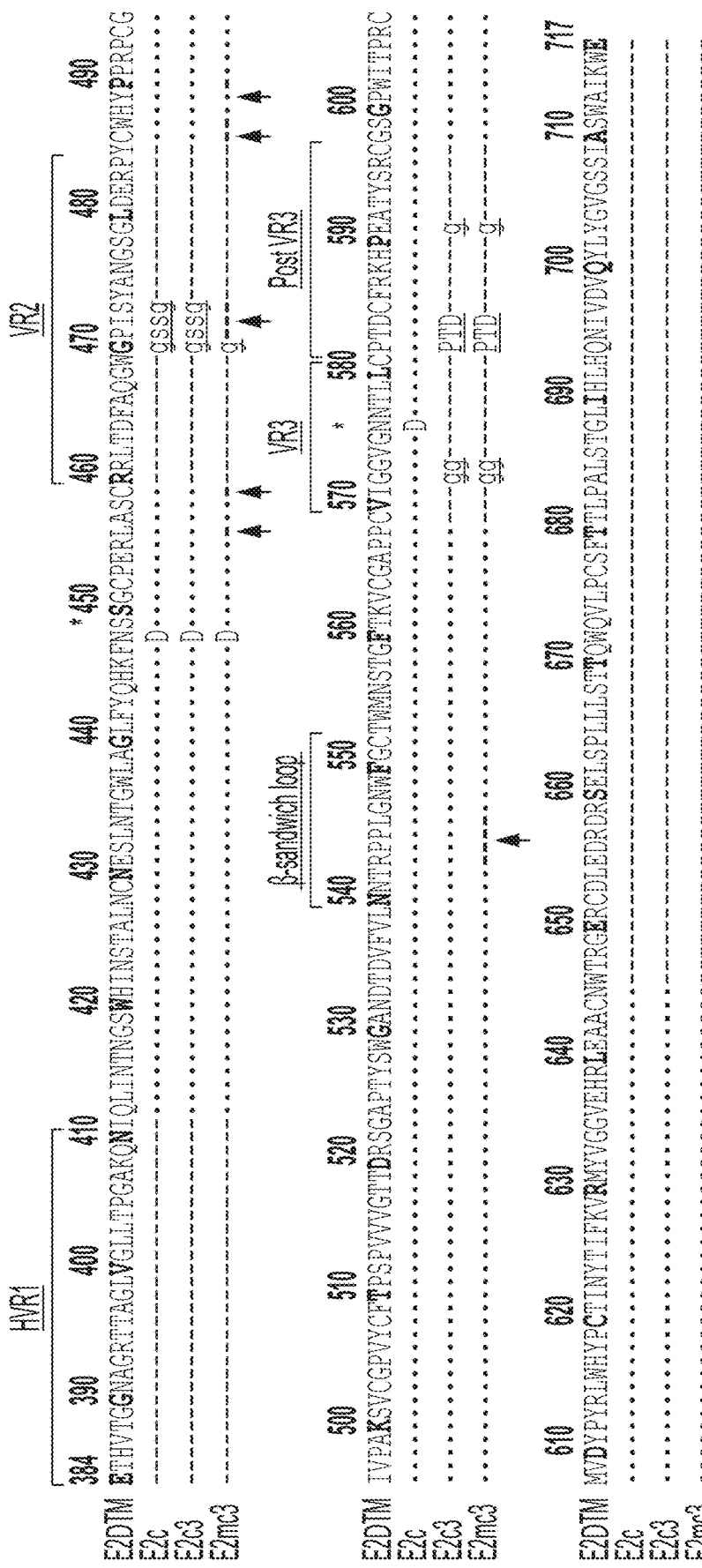

The HCV E2 ectodomain (E2ΔTM or $E2_{ECTO}$) is stabilized by nine conserved disulfide bonds, contains three variable regions including hypervariable region 1 (HVR1, a.a. 384-410), VR2 (a.a. 460-485), and VR3 (a.a. 570-580) and is covered with ~11 N-linked glycans (see Goffard et al., Biochimie 85, 295-301, 2003) (FIG. 1A). HVR1 modulates SR-BI interaction and facilitate host immune evasion by generating escape mutations and shielding neutralizing epitopes. Empirical engineering (FIG. 6A) enabled E2 structure determination by shortening N-/C-termini and VR2, removing glycans at N448 and N576 (see Kong et al., Science 342, 1090-1094, 2013), and additional V3 truncation (see, Tzarum et al., Sci Adv 5, eaav1882, 2019). The E2 core contains a central immunoglobulin (Ig)-like β-sandwich with front and back layers (FIG. 6B). The CD81 receptor binding site is a hydrophobic patch formed by the front layer and CD81 binding loop and overlaps the E2 neutralizing face (FIG. 6B, middle). However, current E2c constructs still exhibit high flexibility involving the front layer C-terminus, shortened VR2, and β-sandwich N-terminus.

Figure 1B:
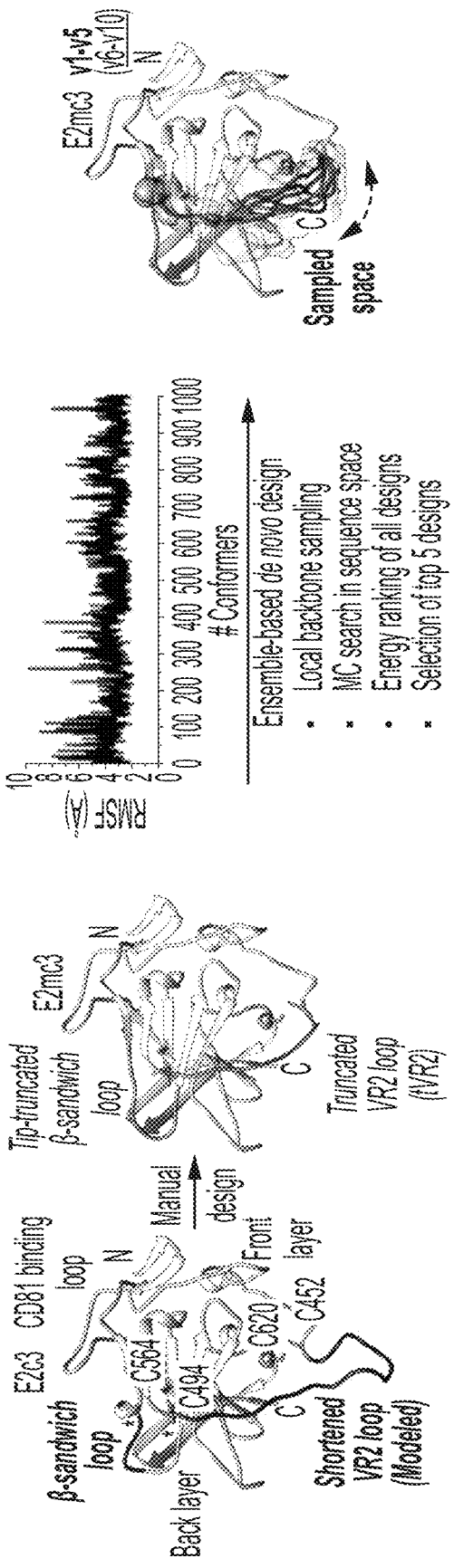
Figure 6E:
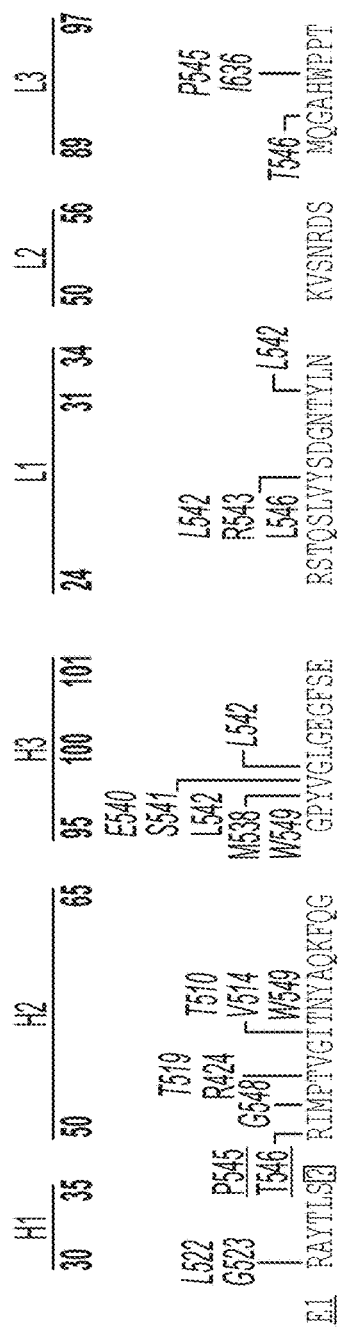
Figure 6F:
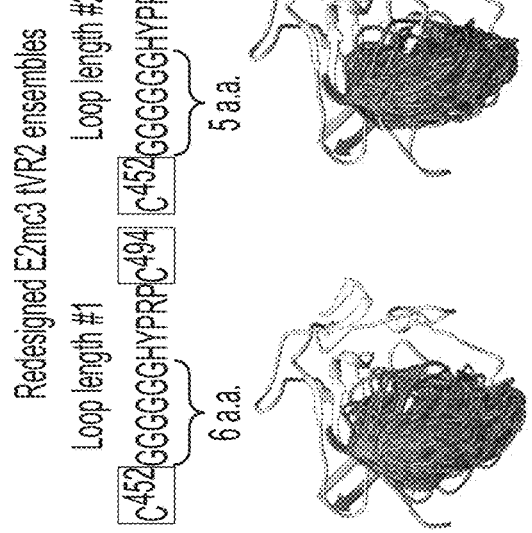
Figure 6G:
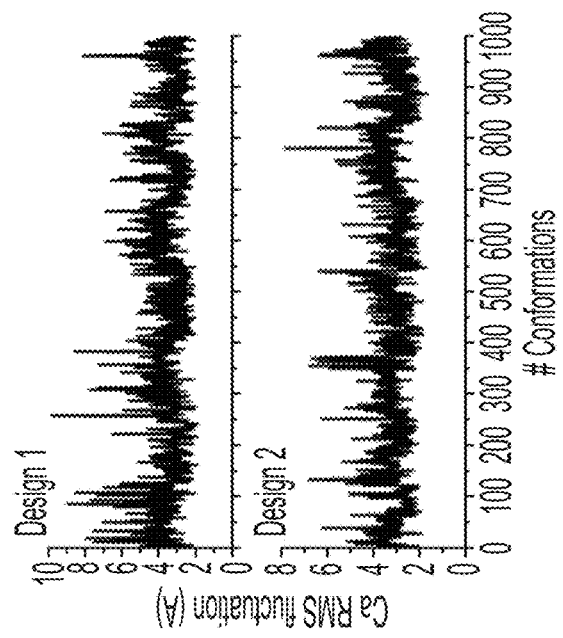
Figure 6H:
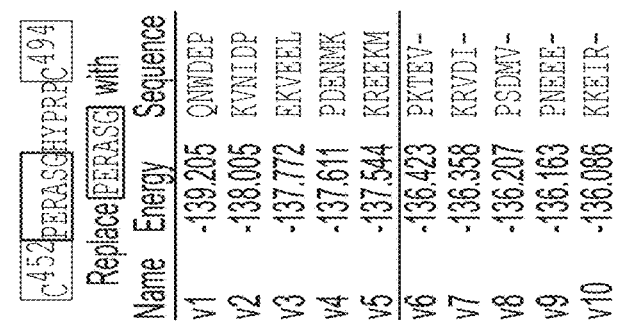
Figure 6I:
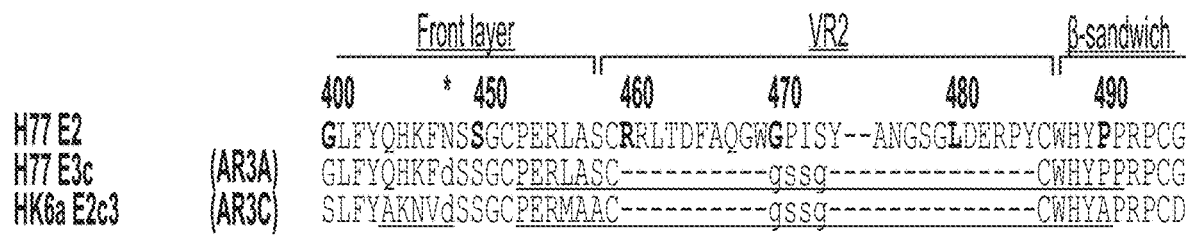

Here, we redesigned the VR2 disordered region that is anchored to the back layer and β-sandwich by two disulfide bonds, C452-C620 and C494-0564 (FIGS. 1A and 1B). Although this region consists of 43 residues in wild-type E2 and 21 residues in E2c/E2c3, the Cα distance between C452 and C494 is 26.3 Å for H77 E2c (FIG. 6B), which could be spanned by only 7 residues. We first manually truncated the VR2 loop to 13 residues (tVR2) (FIGS. 1A, and 1B; FIG. 6A) and deleted the tip (aa 543-546) of the β-sandwich loop (a.a. 540-550) to focus the immune response to bNAb epitopes, as non-NAbs, such as AR1B, E1 and HEPC46, bind to this region (FIGS. 6C-6E). The new E2 core is termed E2 mini-core 3 (E2mc3). Next, we redesigned tVR2 in H77 E2mc3 for two loop lengths, 13 aa (as in E2mc3) and 12 aa, using ensemble-based de novo protein design (see Kong et al., Nat. Commun. 7, 12040, 2016) to identify optimal tVR2 sequences that stabilize E2mc3 (FIG. 1B). For each tVR2 length (13 and 12aa), an ensemble (1,000) of loop conformations was generated to connect C452 and C494 (FIG. 6F) with Cα root-mean-square fluctuation (RMSF) ranging from 1.9 to 9.8 Å (average 3.6 Å) and 1.6 to 7.8 Å (average 3.2 Å), respectively (FIG. 6G). After extensive Monte Carlo sampling, the five top-ranking sequences for each loop length, E2mc3-v1-v5 and v6-v10 (FIG. 1B, right; FIG. 6H), were selected for further characterization. As HK6a E2c3 and H77 E2c share high structural similarity and disordered regions when bound to AR3 bNAbs, we designed HK6a E2mc3 and E2mc3-v1 constructs (FIG. 6I) without further modification. In total, eleven H77 E2 cores and two HK6a E2 cores were advanced to experimental evaluation.

Figure 1C:
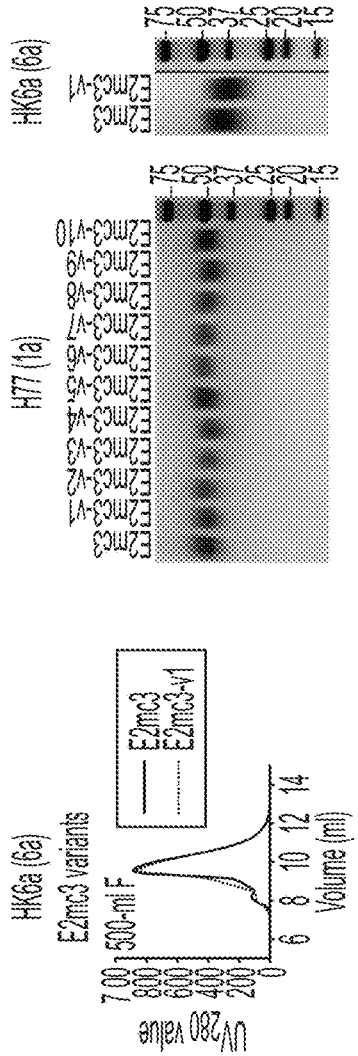
Figure 1D:
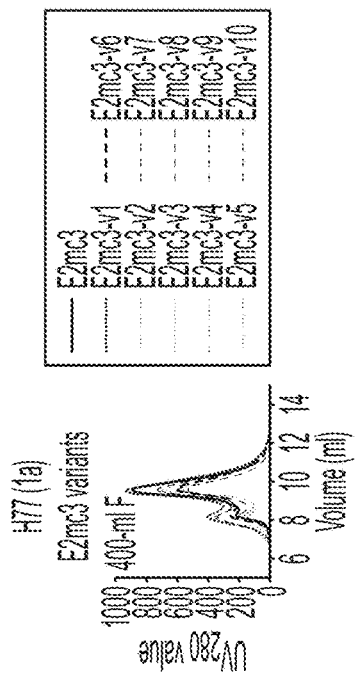
Figure 7A:
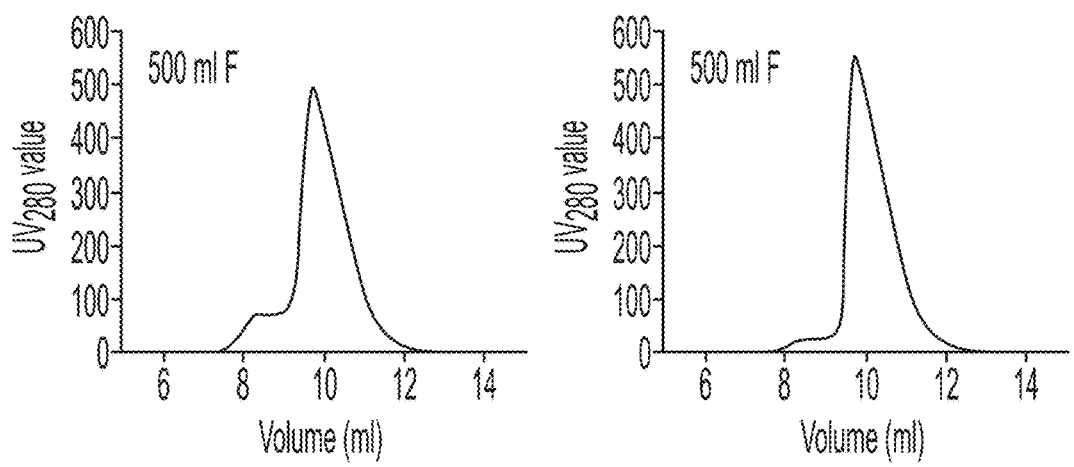
Figure 7B:
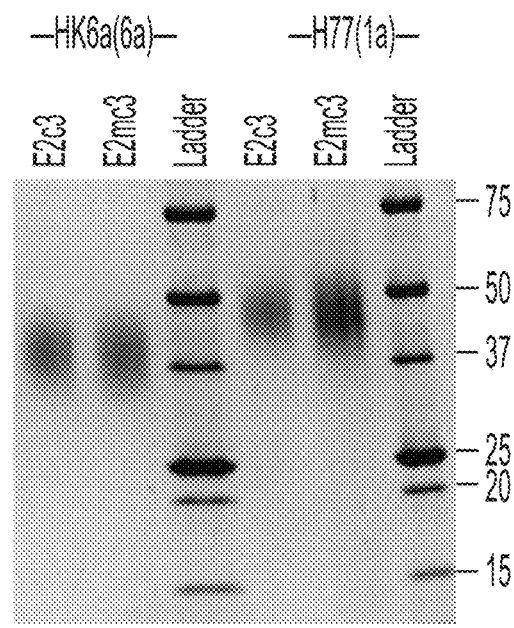
Figures 1, 7D:
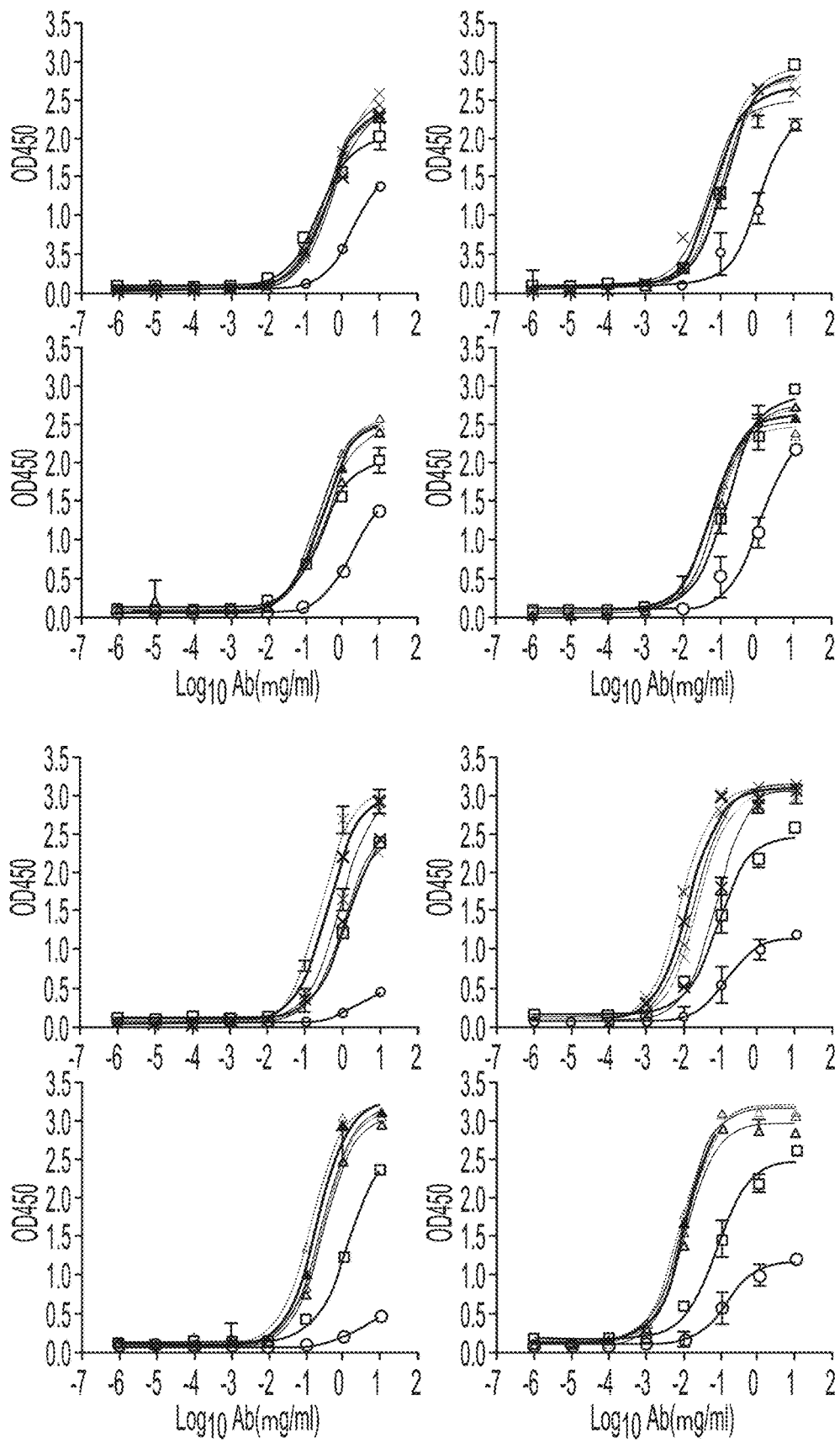
Figures 2, 7D:
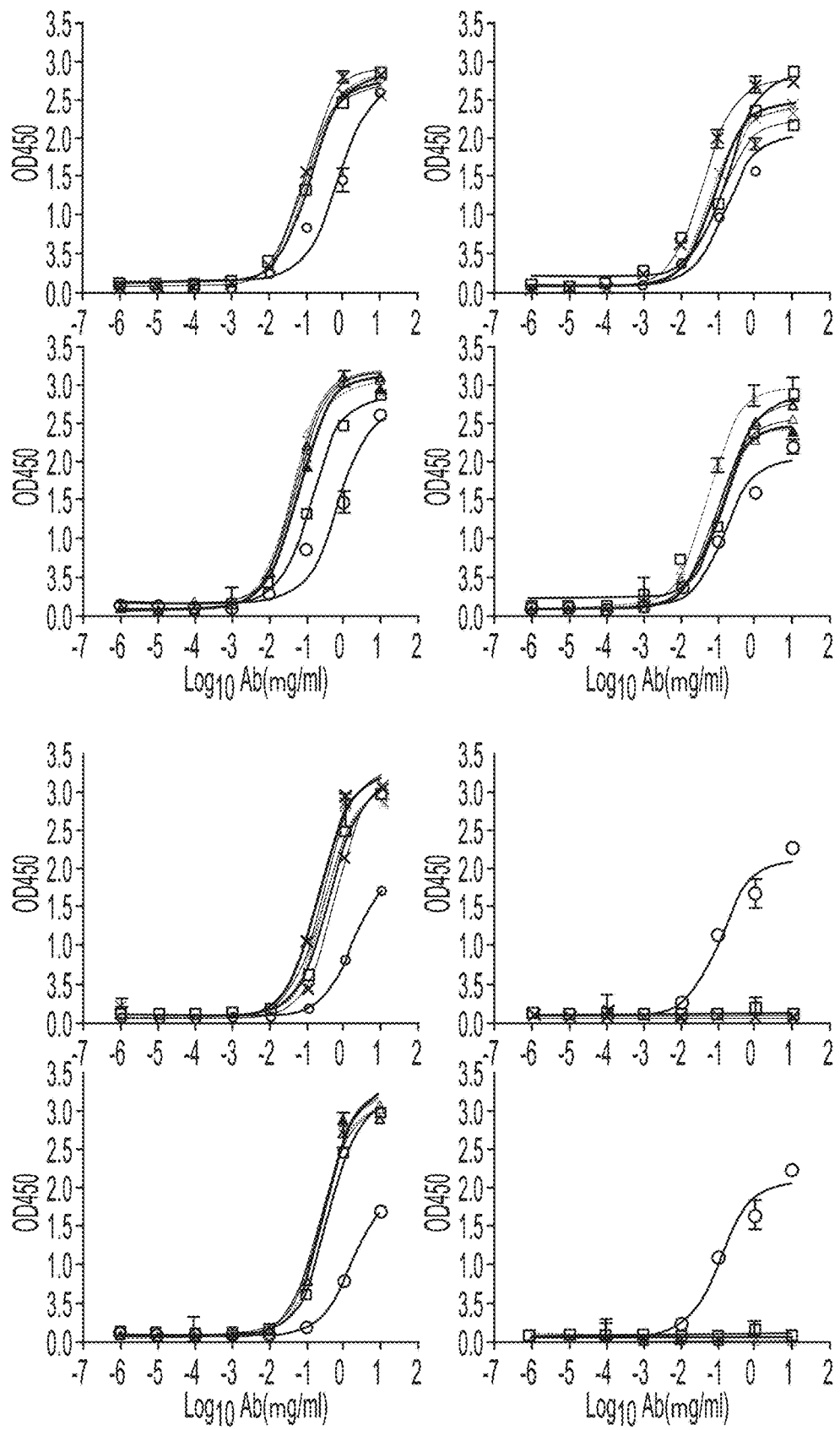
Figures 3, 7D:
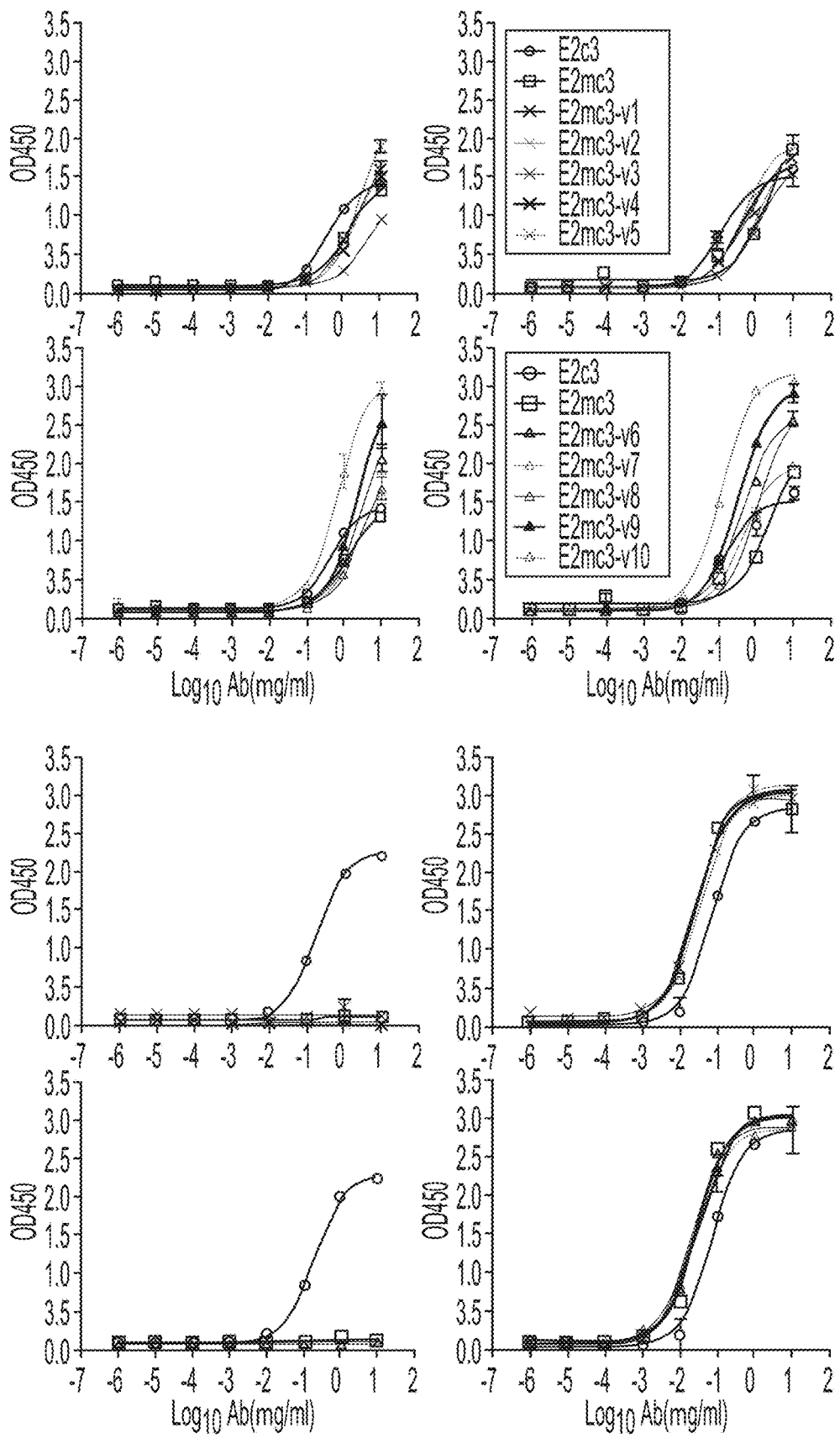
Figures 1, 7F:
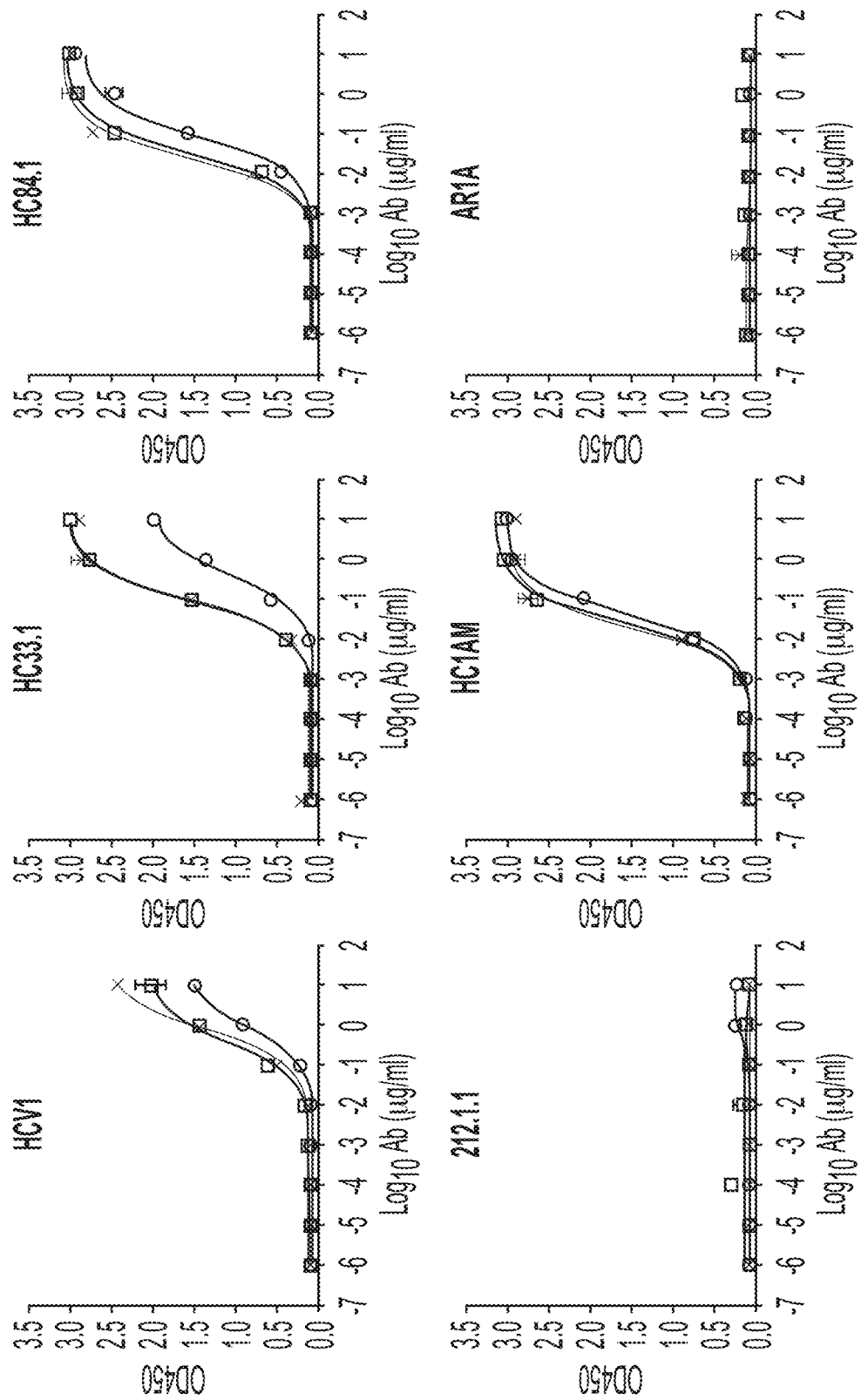
Figures 2, 7F:
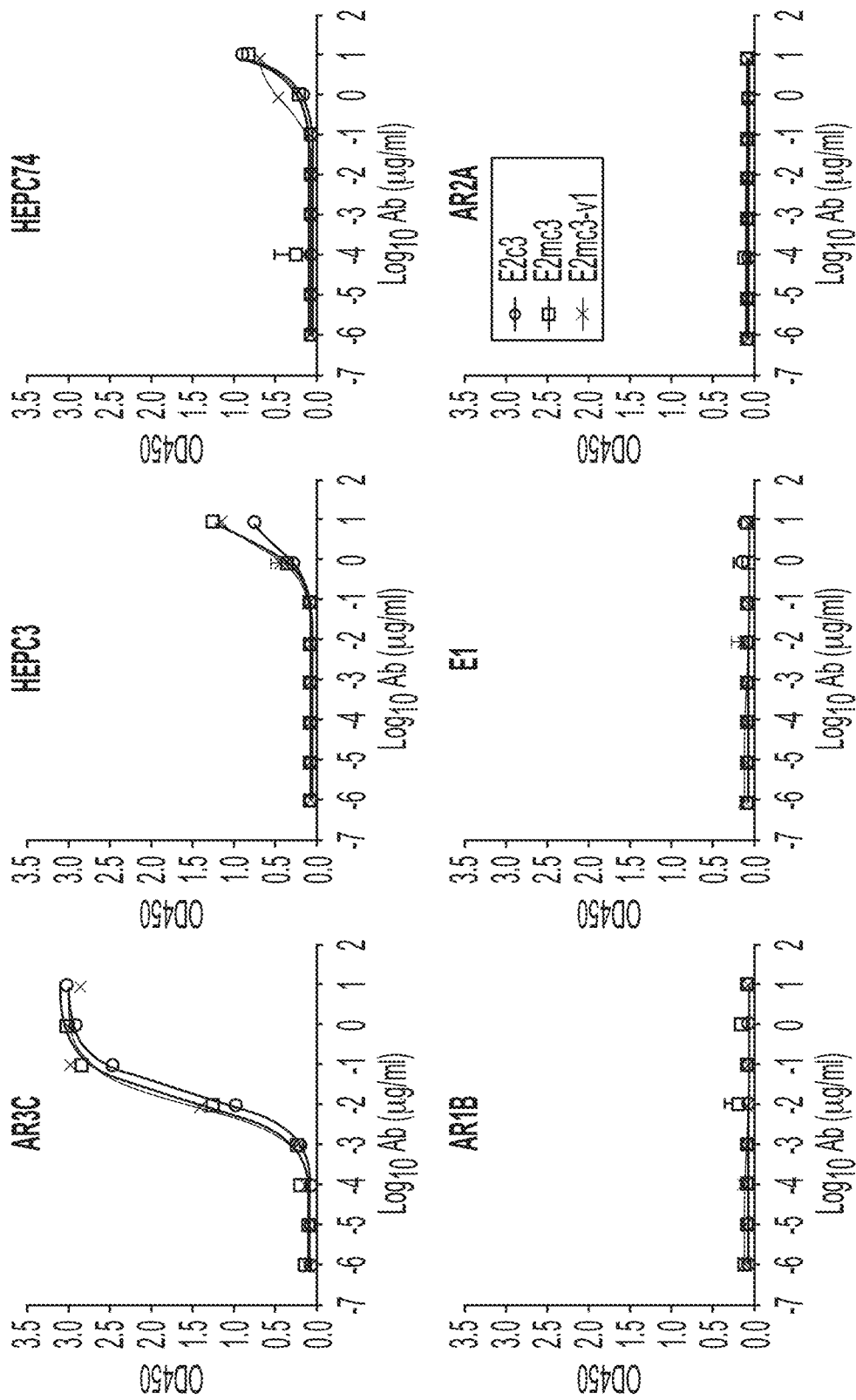
Figures 1, 7H:
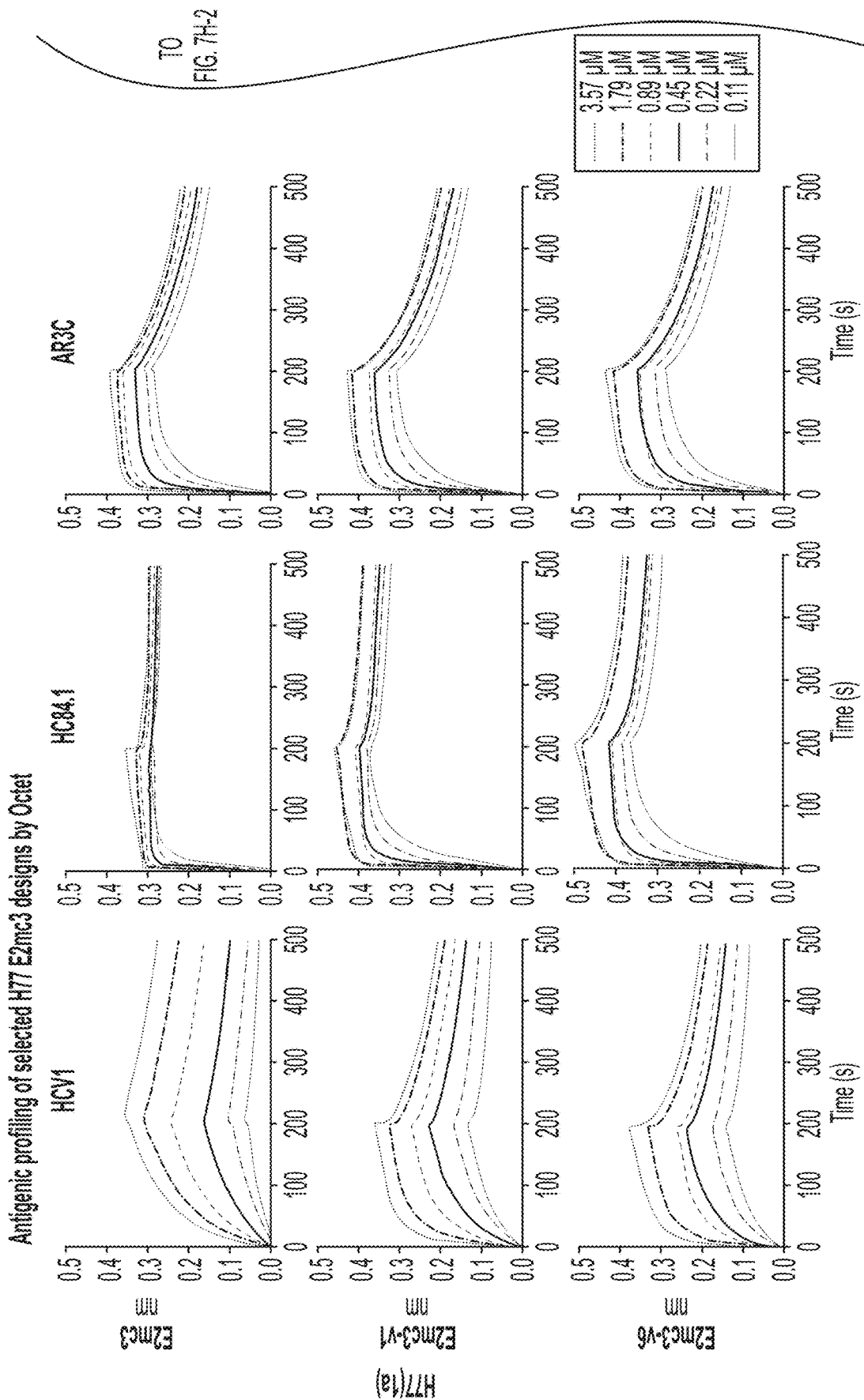
Figures 2, 7H:
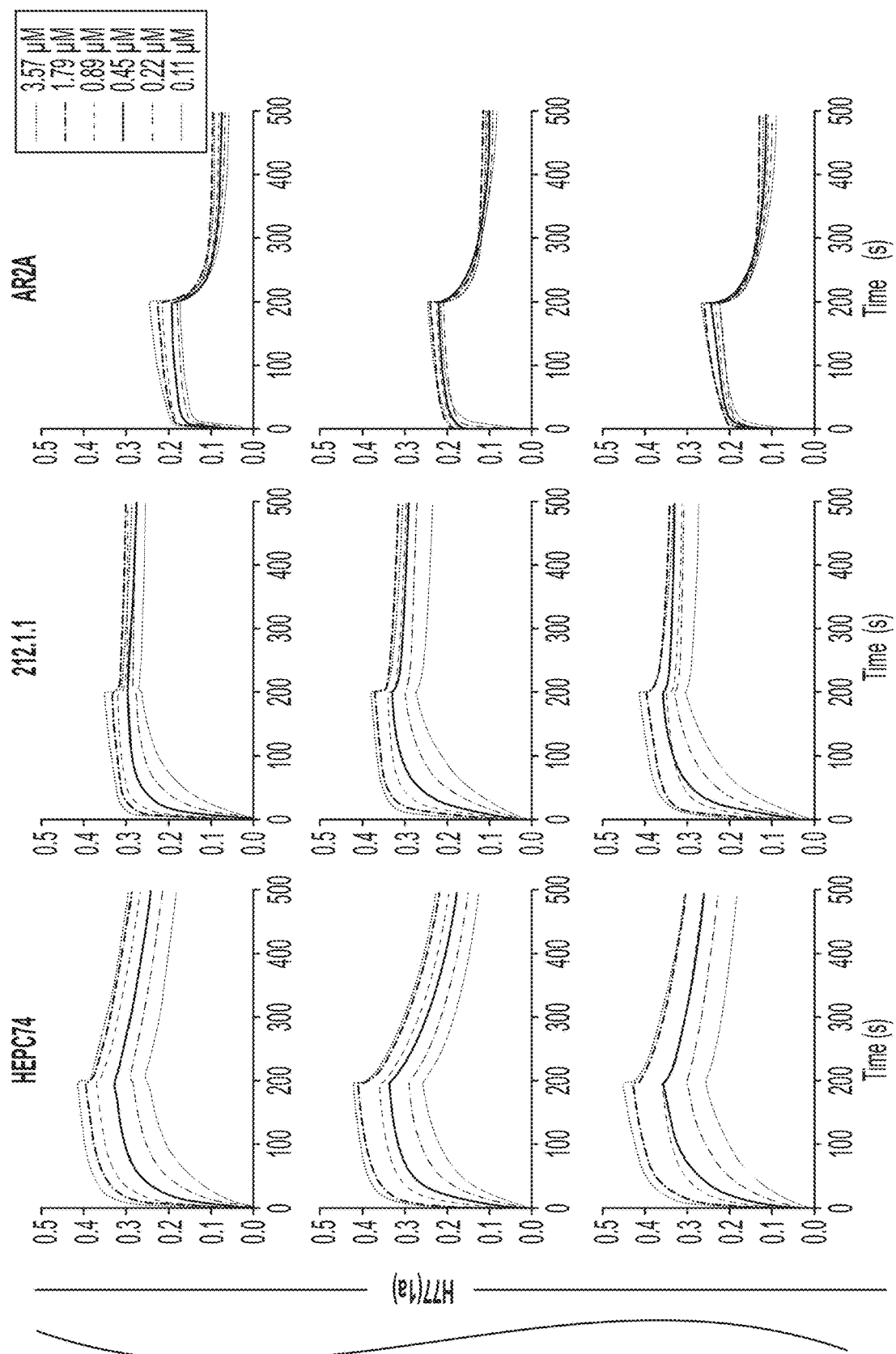
Figures 1, 7I:
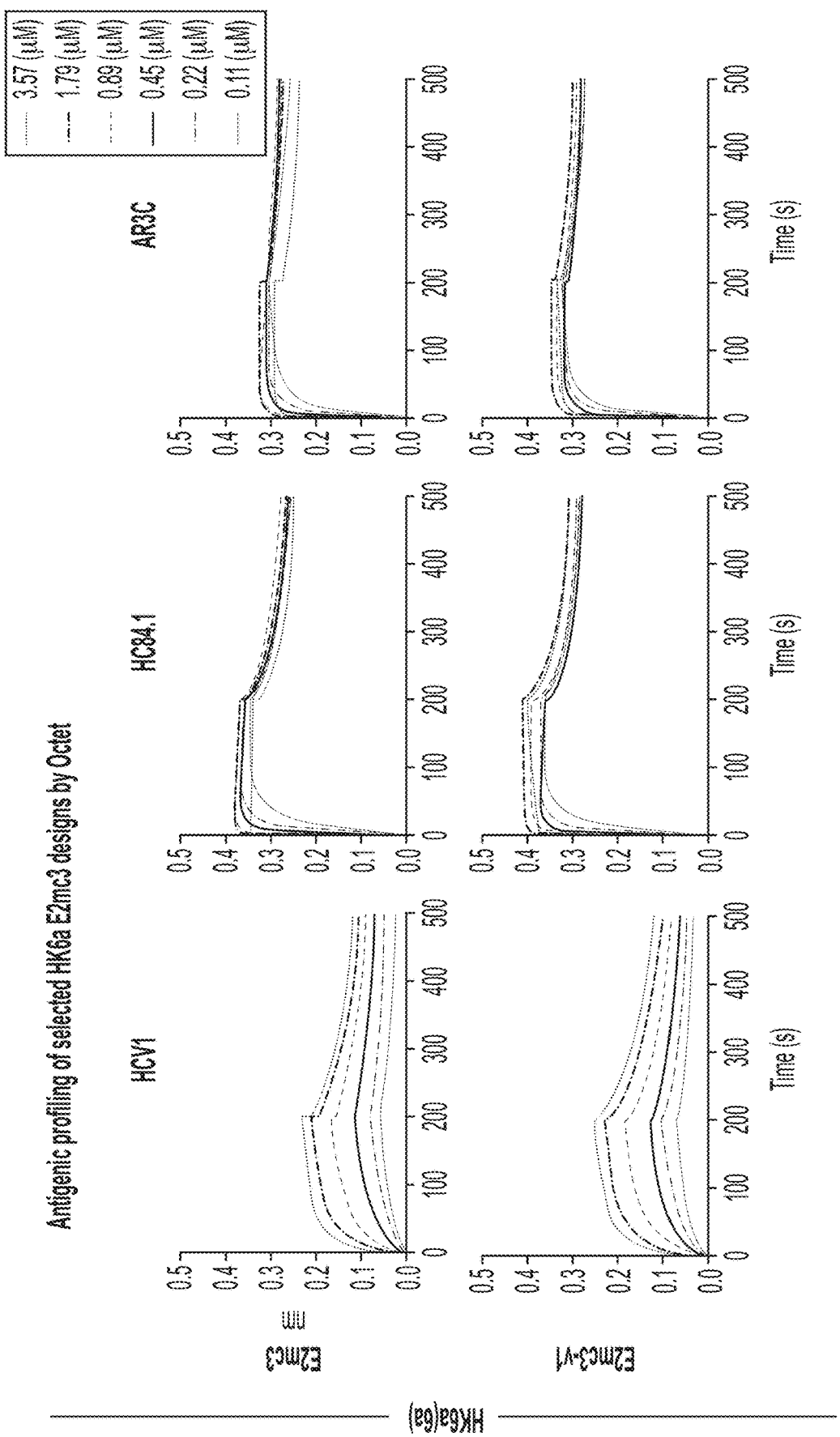
Figures 2, 7I:
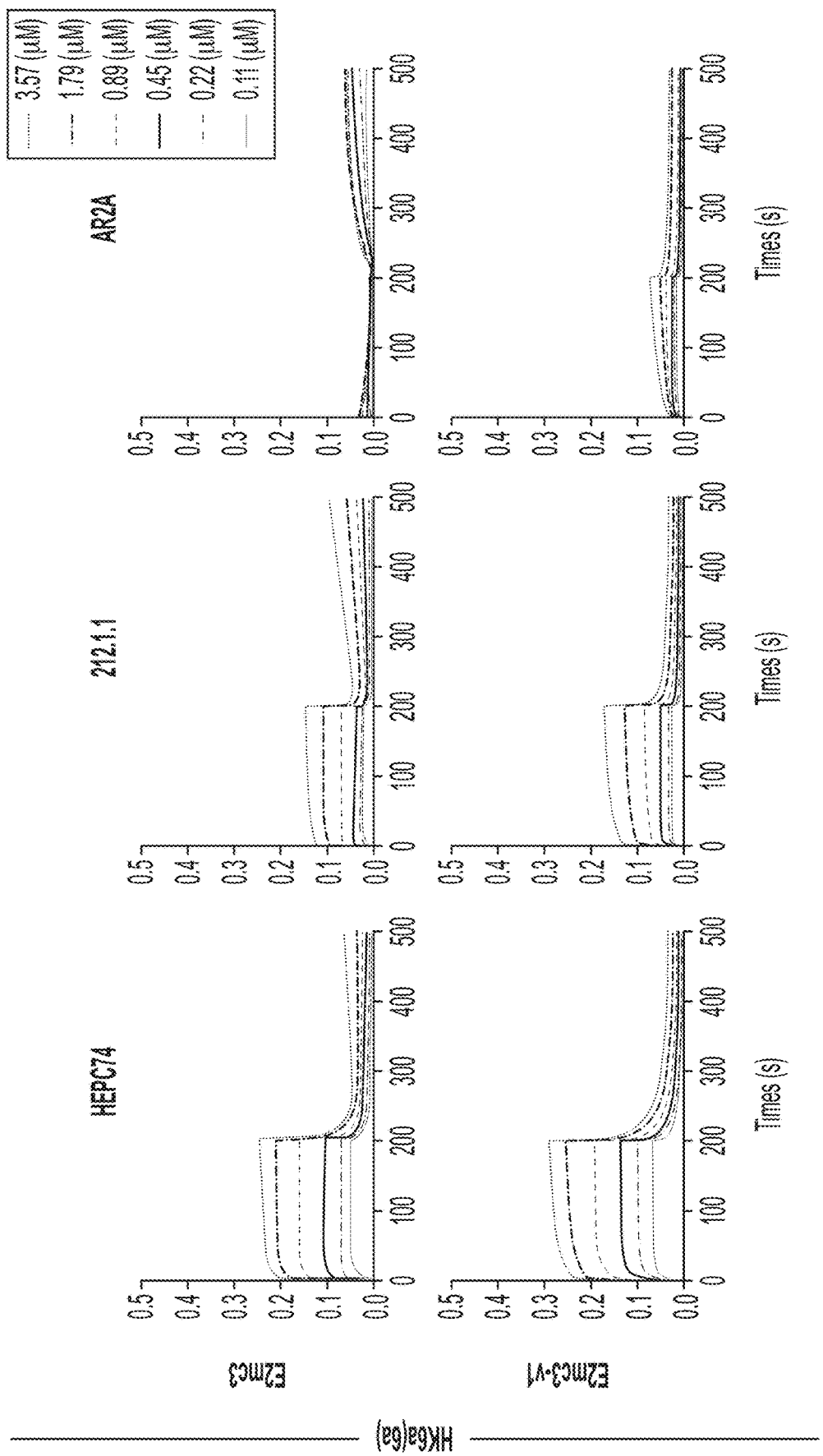
Figure 7K:
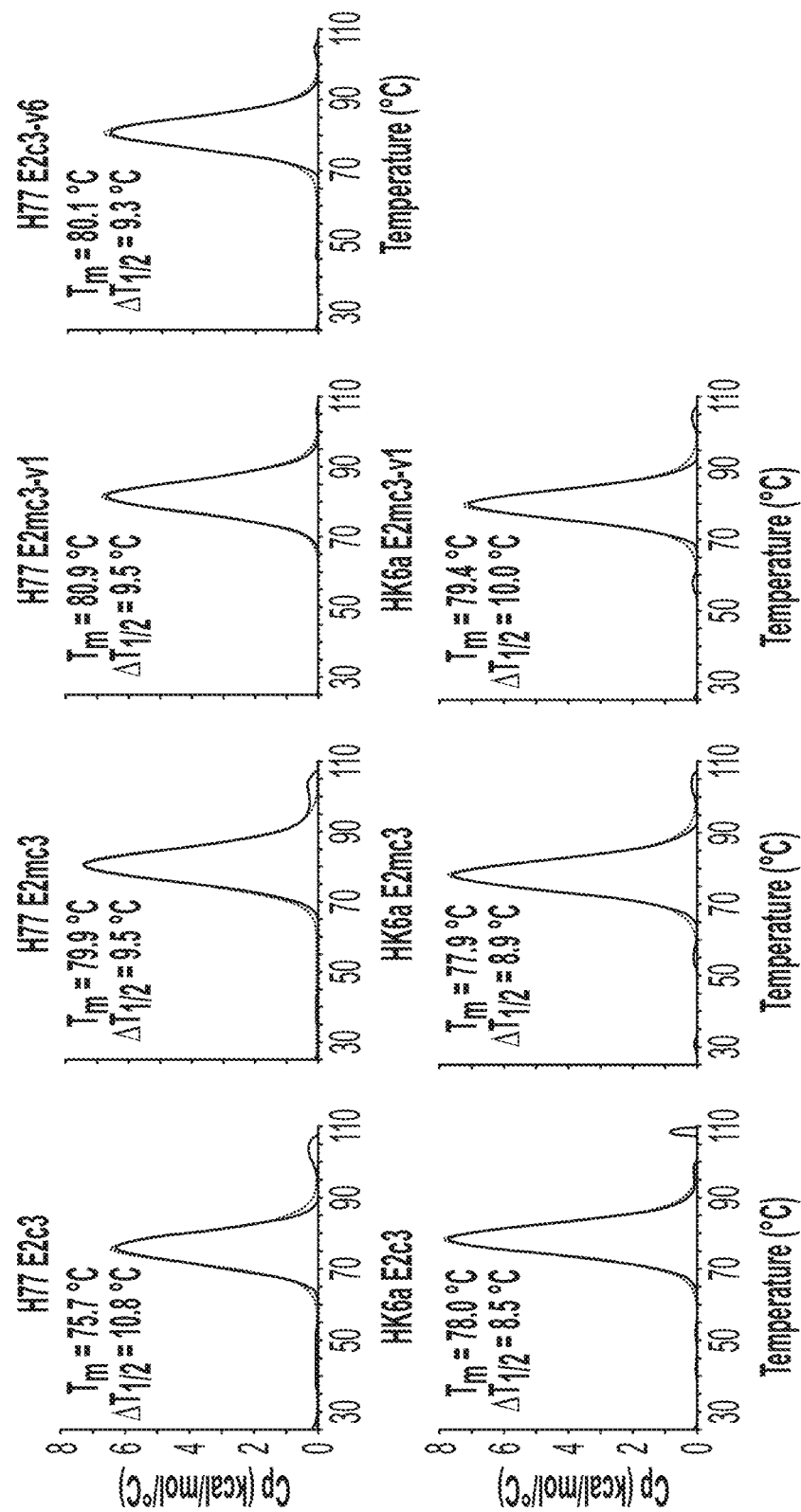

Example 2 Biochemical, Biophysical, and Antigenic Assessment of HCV E2mc3 Designs 13 E2mc3 constructs from H77 and HK6a and two parental E2c3 constructs (see, Tzarum et al., Sci Adv 5, eaav1882, 2019; and Kong et al., Proc. Natl. Acad. Sci. U.S.A. 113, 12768-12773, 2016) were transiently expressed in HEK293 F cells and purified using immunoaffinity (see Kong et al., Science 342, 1090-1094, 2013) followed by size exclusion chromatography (SEC). Overall, the purified E2mc3 variants showed greater yield than their respective E2c3 constructs ranging from 5.0 to 11.5 mg from 1 L 293F transfection. AR3A-purified E2mc3 was mostly in monomeric form with a small aggregate peak (FIG. 1C and FIG. 7A) and SEC-purified proteins ran as a single band (~50 kDa) on SDS-PAGE (FIG. 1D and FIG. 7B). We then tested H77 and HK6a E2mc3 variants by ELISA on a panel of HCV antibodies that includes (b)NAbs targeting antigenic site 412 (AS412), AS434, antigenic region 3 (AR3), AR2, and non-NAbs targeting AR1 (FIG. 7C). H77 E2mc3 showed greater binding than E2c3 for most bNAbs (excluding HEPC3/74) and NAb AR2A, with further improvements for some E2mc3 variants (FIG. 1E, upper panel; FIGS. 7D-1 to 7D-3, and 7E). As expected, truncation of the β-sandwich loop reduced binding to non-NAbs AR1B and E1 with negligible effect on ARIA, which recognizes AR1 but not the β-sandwich loop. Similar patterns were observed for HK6a E2mc3 and E2mc3-v1 except for 212.1.1 (FIG. 1E, lower panel; FIGS. 7F-1 to 7F-2, and 7G) with no detectable binding by genotype-specific AR2A and AR1A/B. By biolayer interferometry (BLI), HK6a E2mc3 variants exhibited similar antigenic profiles (FIG. 1F; FIGS. 7H-1 to 7J). Differential scanning calorimetry (DSC) showed a 4.2° C. increase in $T_m$ for E2mc3 (H77) relative to E2c3 that was further increased by 1° C. and 0.2° C. for E2mc3-v1 and v6, respectively (FIG. 1G and FIG. 7K).

Example 3 Characterization of Minimized Cores Derived from H77 and HK6a

Figure 1E:
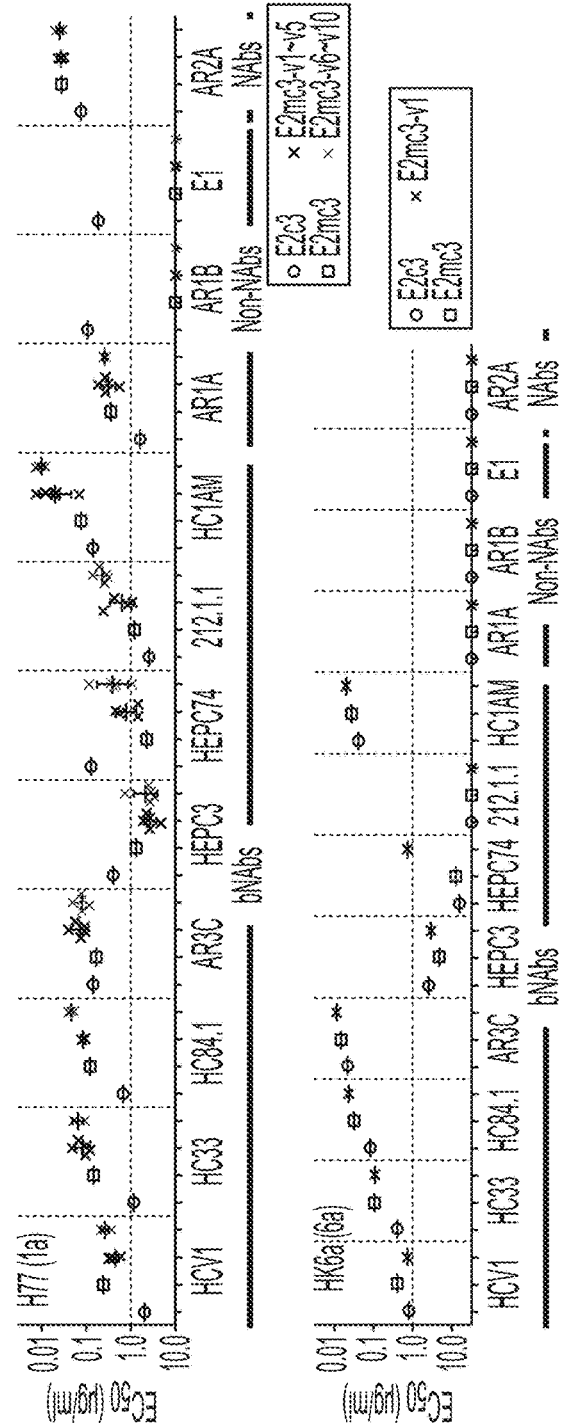
Figure 1F:
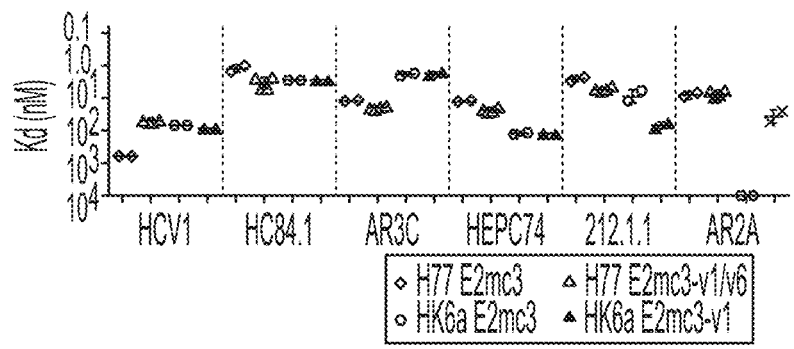
Figure 2A:
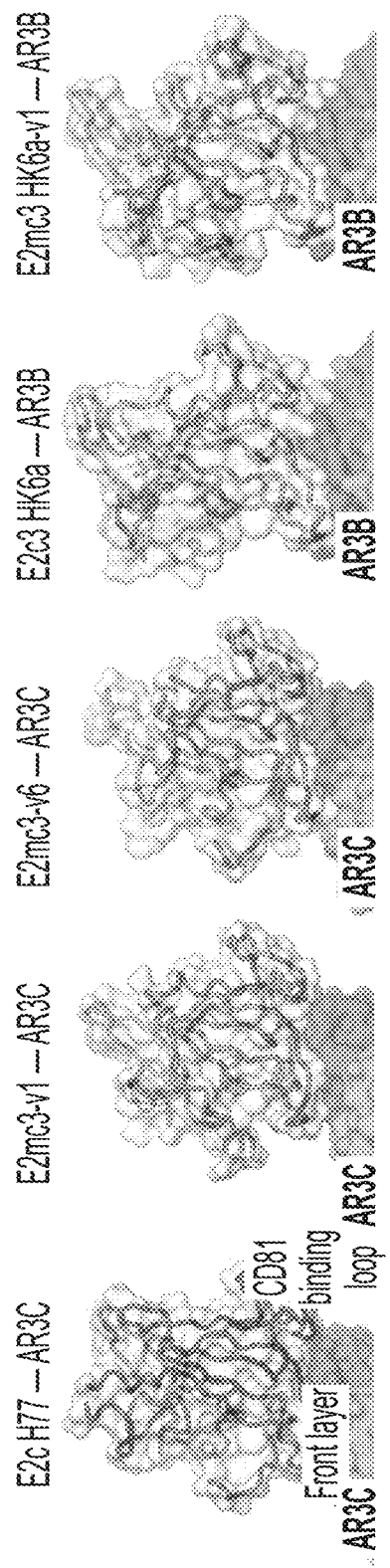
Figure 2B:
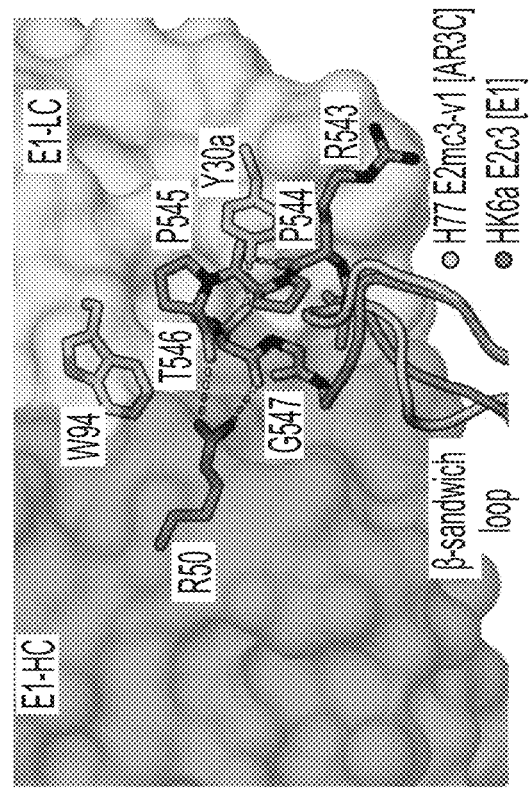
Figure 9A:
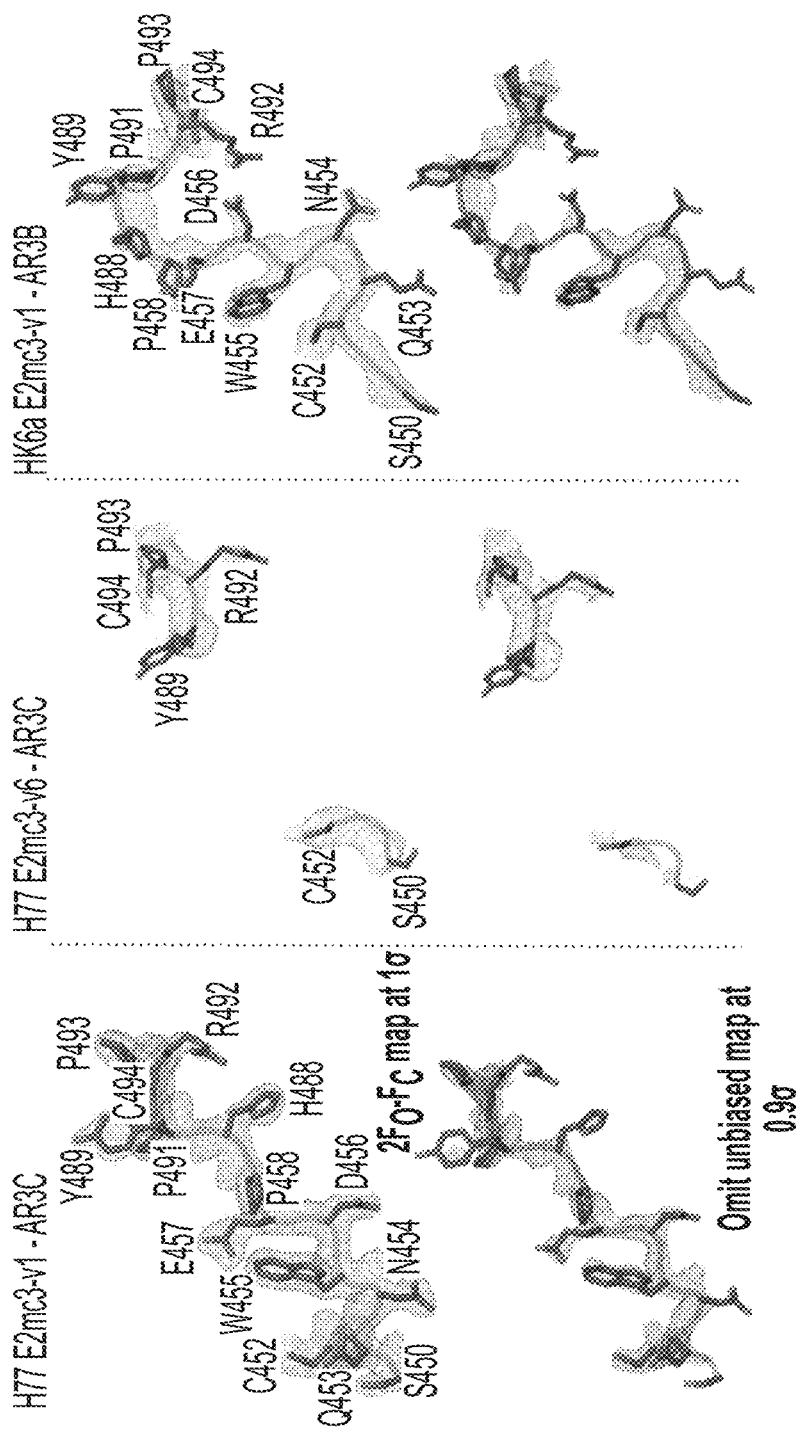
FIGS. 9A-9D show structural analysis of the redesigned tVR2 region. (9A) 2Fo-Fc and unbiased omit electron density maps of the redesigned VR2 region (16 or 0.9σ, respectively). (9B) The intrinsic interactions of the redesigned tVR2 region of H77 E2mc3-v1, H77 E2mc3-v6, and HK6a E2mc3-v1 with the VR3 and post VR3 regions (a.a. 570-597). (9C) Comparison of the H77 E2mc3-v1 and HK6a E2mc3-v1 indicating conformation changes of the redesigned VR2 and the neighboring VR3-back layer region (a.a. 565-608). (9D) In the crystal structure of the truncated 1b09 E2 ectodomain (left), the full length VR2 wraps around VR3 to form the variable face. Superposition of H77 E2mc3-v1 structure on 1b09 E2 indicates only a minor influence of the VR2 redesign on the E2 overall fold (as indicated by aligning C452 and C494).
Figure 9B:
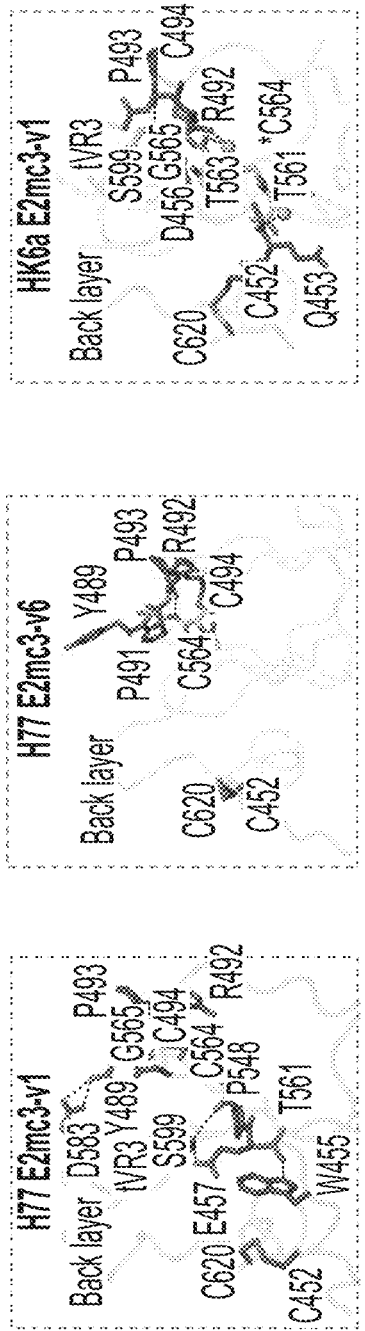
Figure 9C:
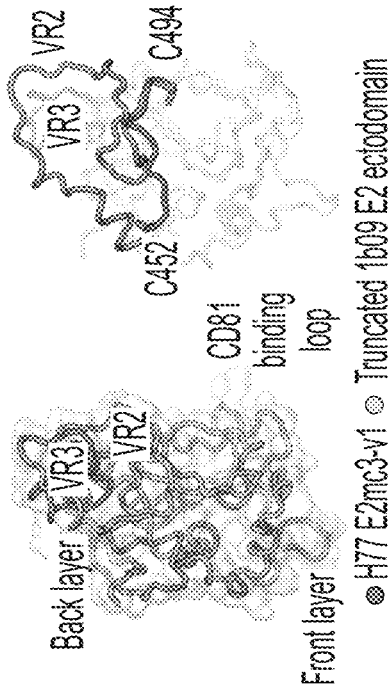
Figure 9D:
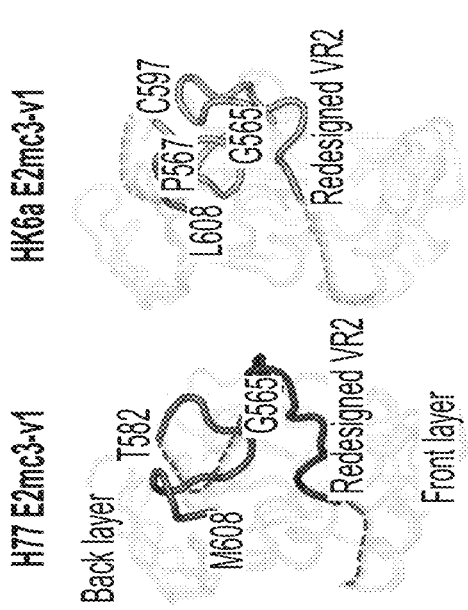

Crystallization of H77 and HK6a E2 cores with Fabs from AR3A/B/C/D bNAbs led to structures of H77 E2mc3-v1 and E2mc3-v6 with AR3C and HK6a E2mc3-v1 with AR3B at 1.90 Å, 2.85 Å, and 2.06 Å, respectively (FIGS. 2A-2D). The overall fold of E2mc3 variants is highly similar to H77 E2c and HK6a E2c3 (PDB: 4MWF and 6BKB) (FIGS. 8A-8B), but with differences in the back layer C-terminus (a.a. 629-640) and a front layer loop (a.a. 430-438) (FIG. 8A) that interacts with HCDR3 of bNAbs AR3A-D. However, similar (hydrophilic) contacts are maintained with HCDR3 (FIG. 8A) further supporting the conformational plasticity of the E2 front layer. The shortened β-sandwich loop can be fully modeled in the H77 E2mc3-v1 complex with bNAb AR3C (FIG. 8B), confirming that its truncation results in loss of key interactions with non-NAb E1 (FIG. 1E and FIG. 2B). The redesigned tVR2 can be fully modeled in bNAb-bound H77 and HK6a E2mc3-v1 structures but is only partially visible in the AR3C-bound H77 E2mc3-v6 structure (FIG. 2C and FIG. 9A). The tVR2 redesign does not introduce any conformational changes to the E2 neutralizing face (FIG. 2D), which is anchored to the back layer and β-sandwich by C452-C620 and C494-0564 and interacts with the truncated VR3 and β-sandwich (FIG. 9B). While H77 and HK6a E2mc3-v1 constructs share the same tVR2 sequence, a significant difference in conformation (FIG. 2C and FIG. 9C) likely results from differences in sequence and structure of adjacent VR3 and β-sandwich loop in genotypes 1 and 6 (FIG. 8B and FIG. 9C). The tVR2 redesign has minimal effect when compared to recent truncated $E2_{ECTO}$ structures from isolates 1a53 and 1b09 of genotype 1 with bNAbs HEPC3/74 (FIG. 6B and FIG. 9D).

Figure 3C:
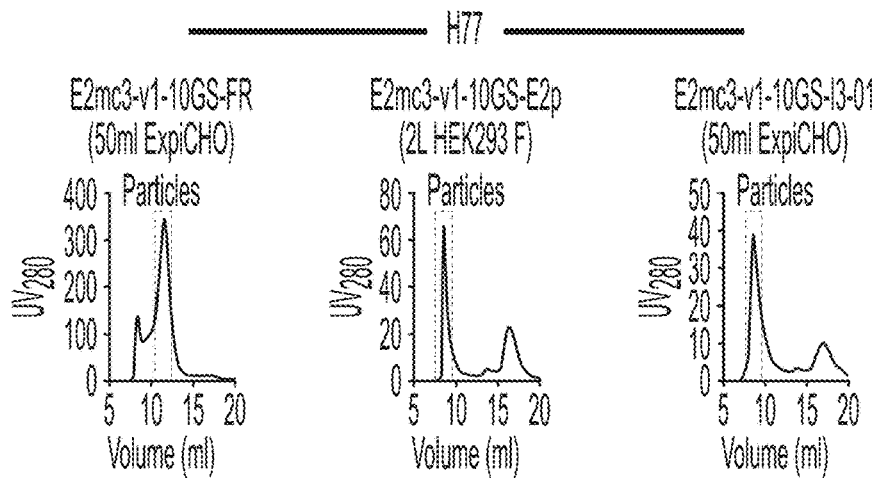
Figure 3D:
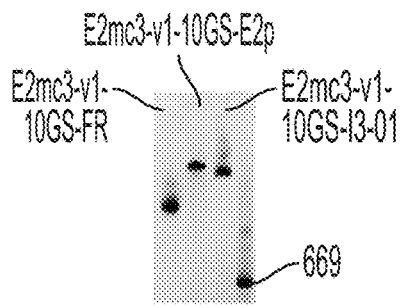
Figure 3E:
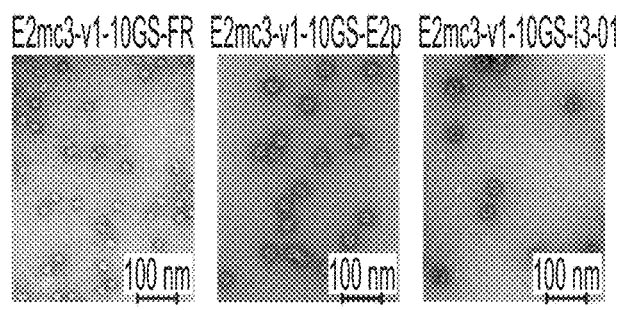
Figures 3F, 3G:
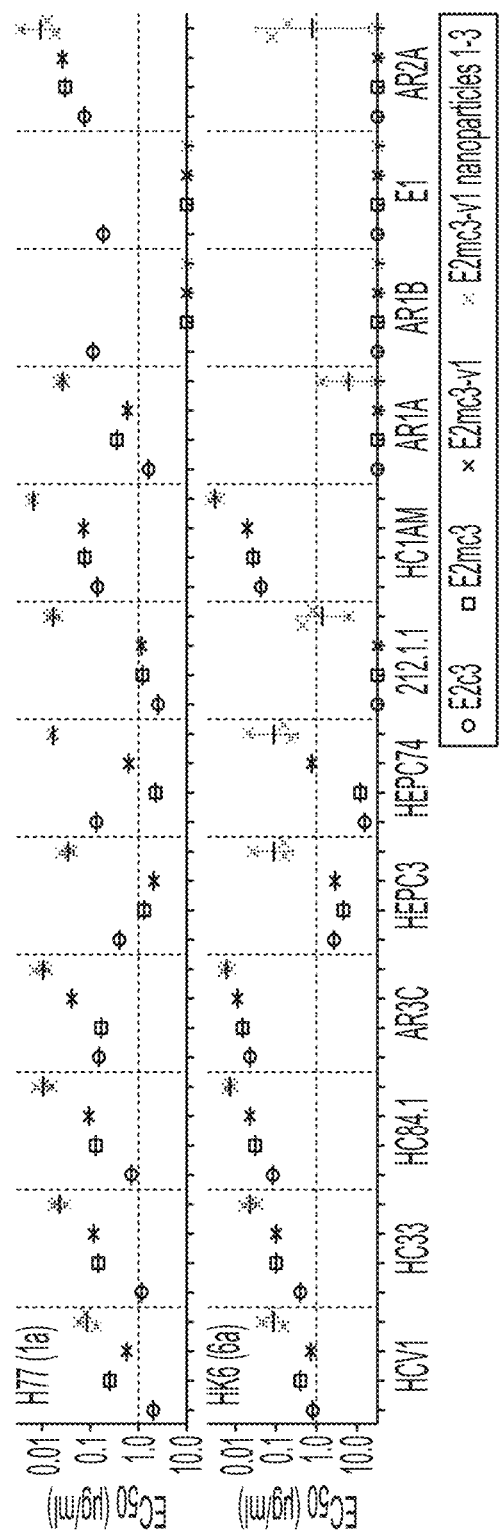
Figures 1, 10D:
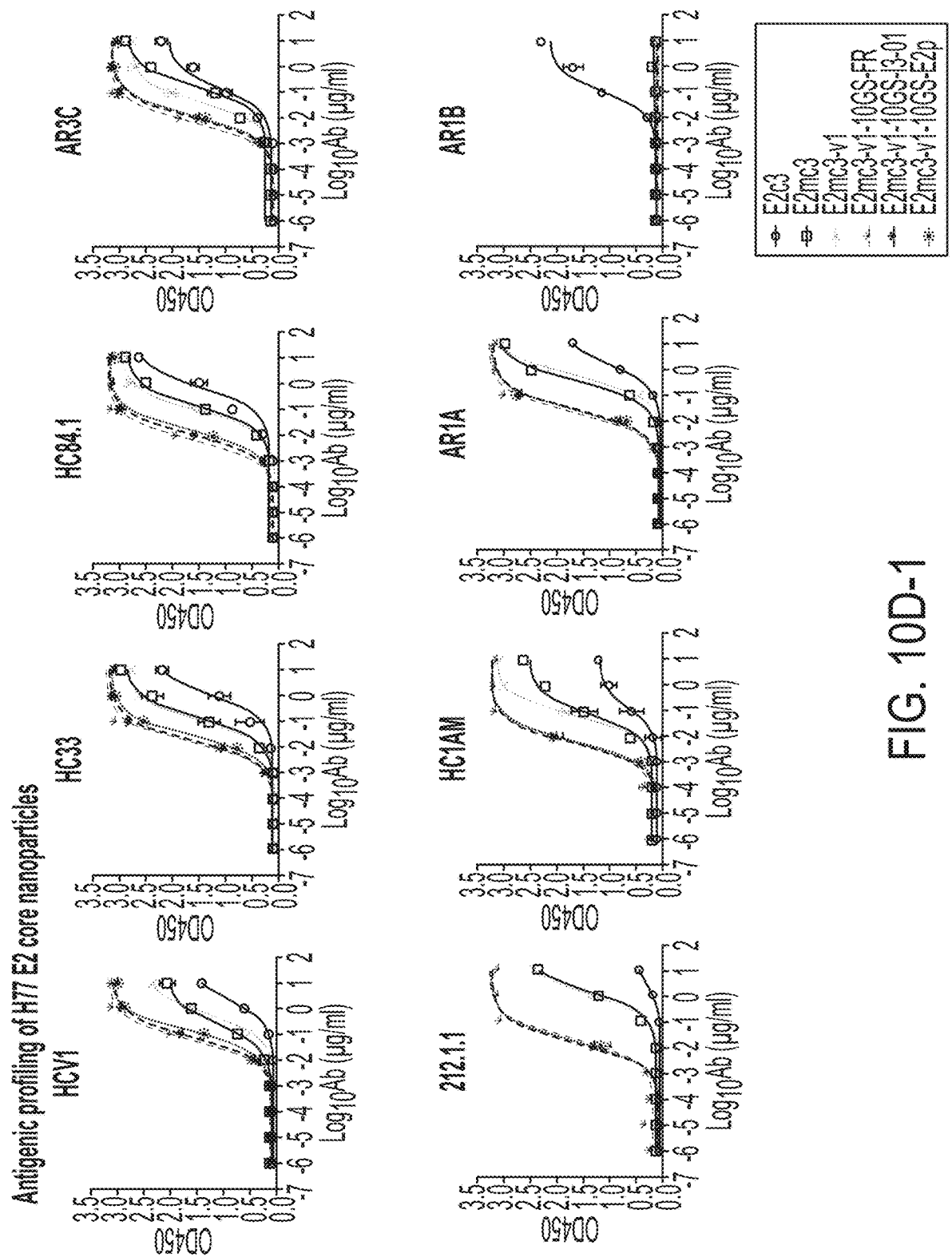
Figures 2, 10D:
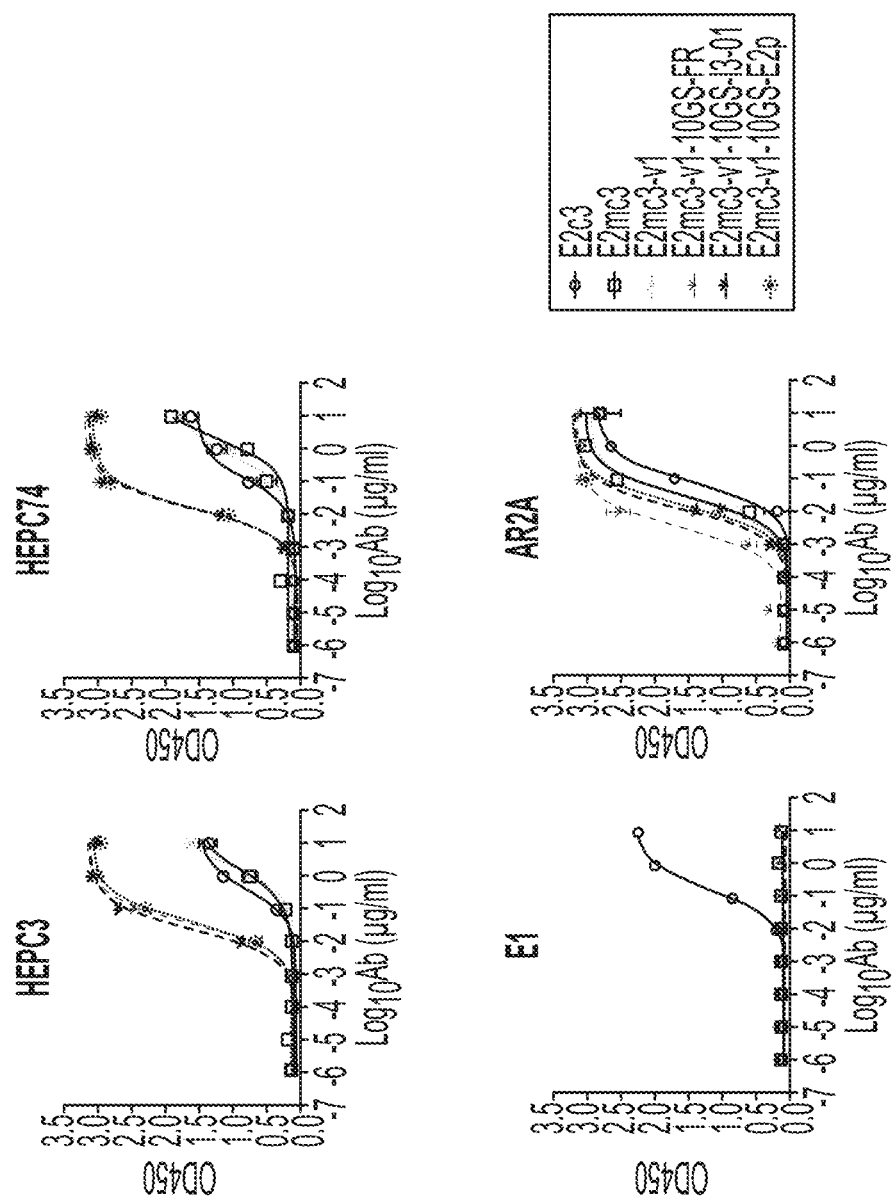
Figures 1, 10F:
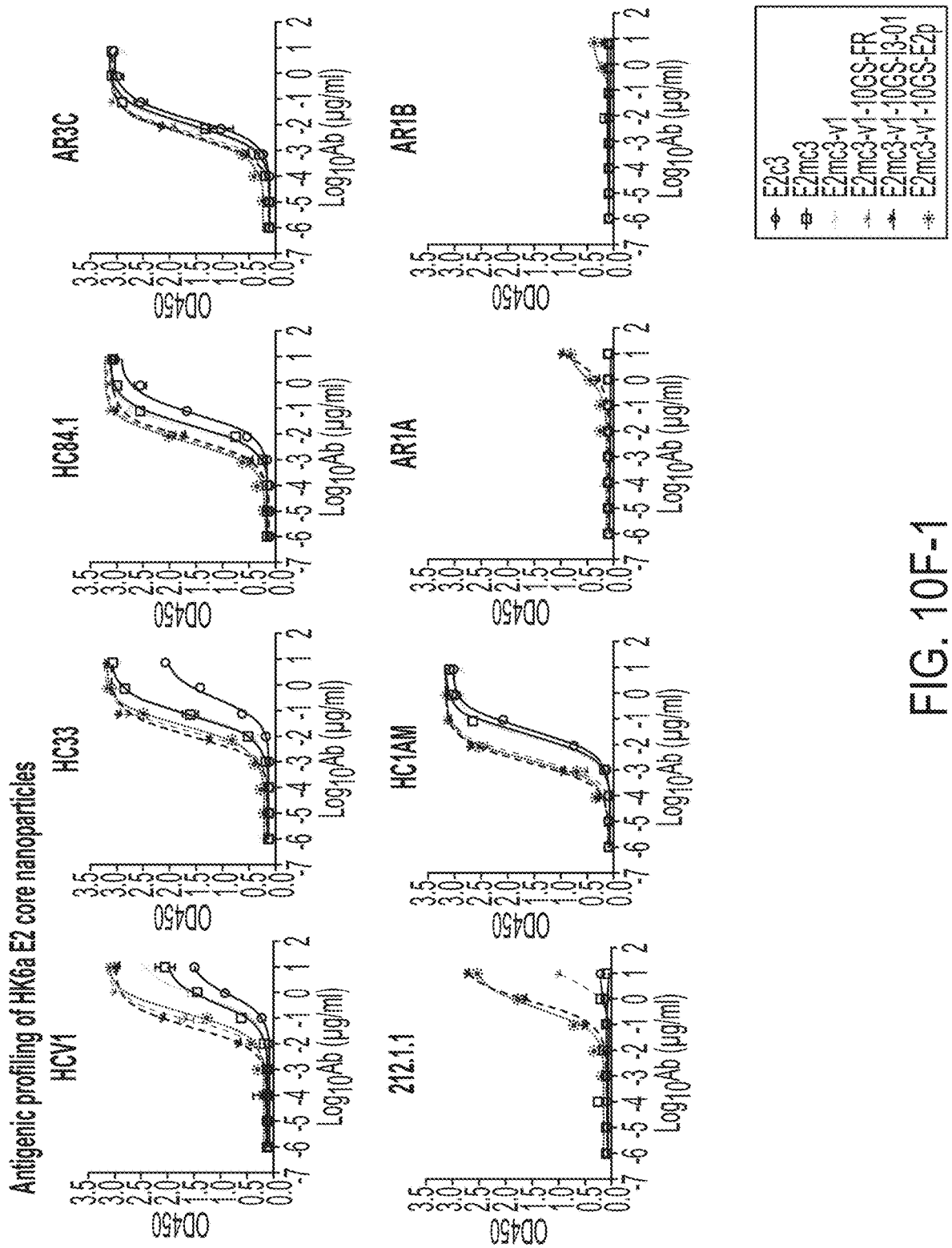
Figures 2, 10F:
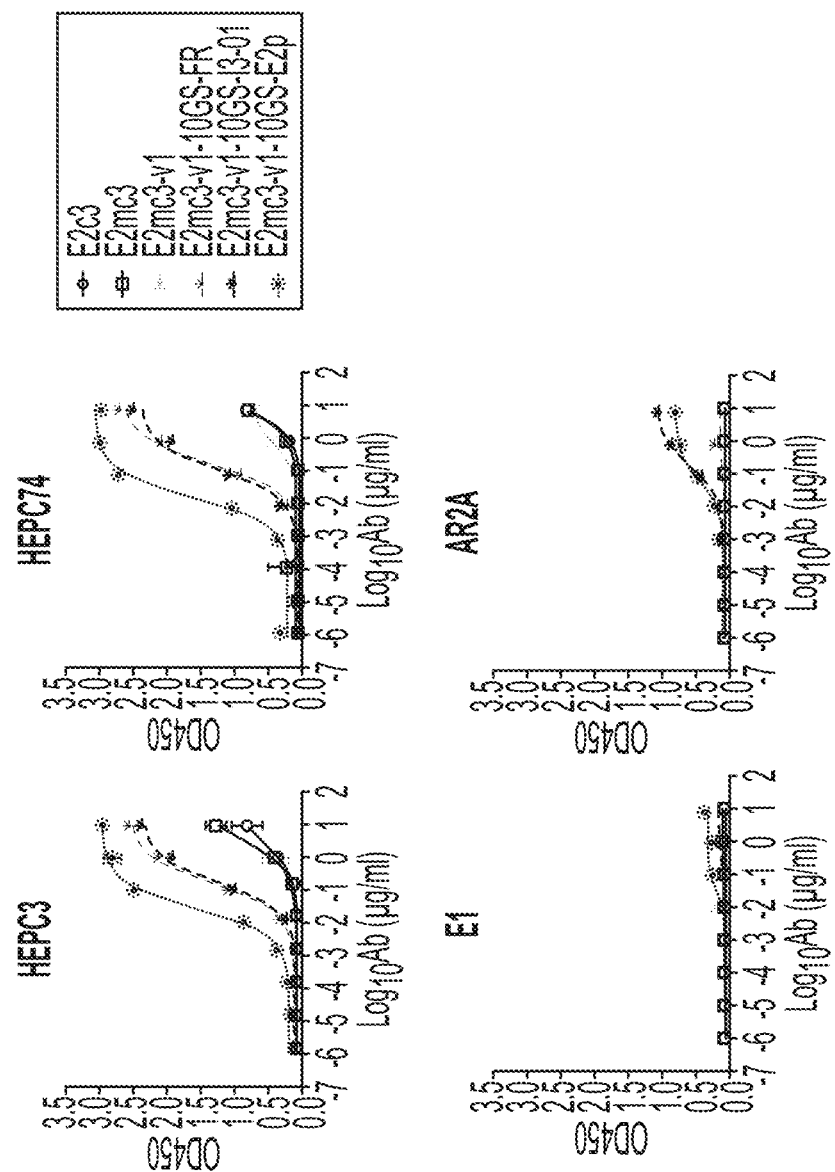
Figures 1, 10H:
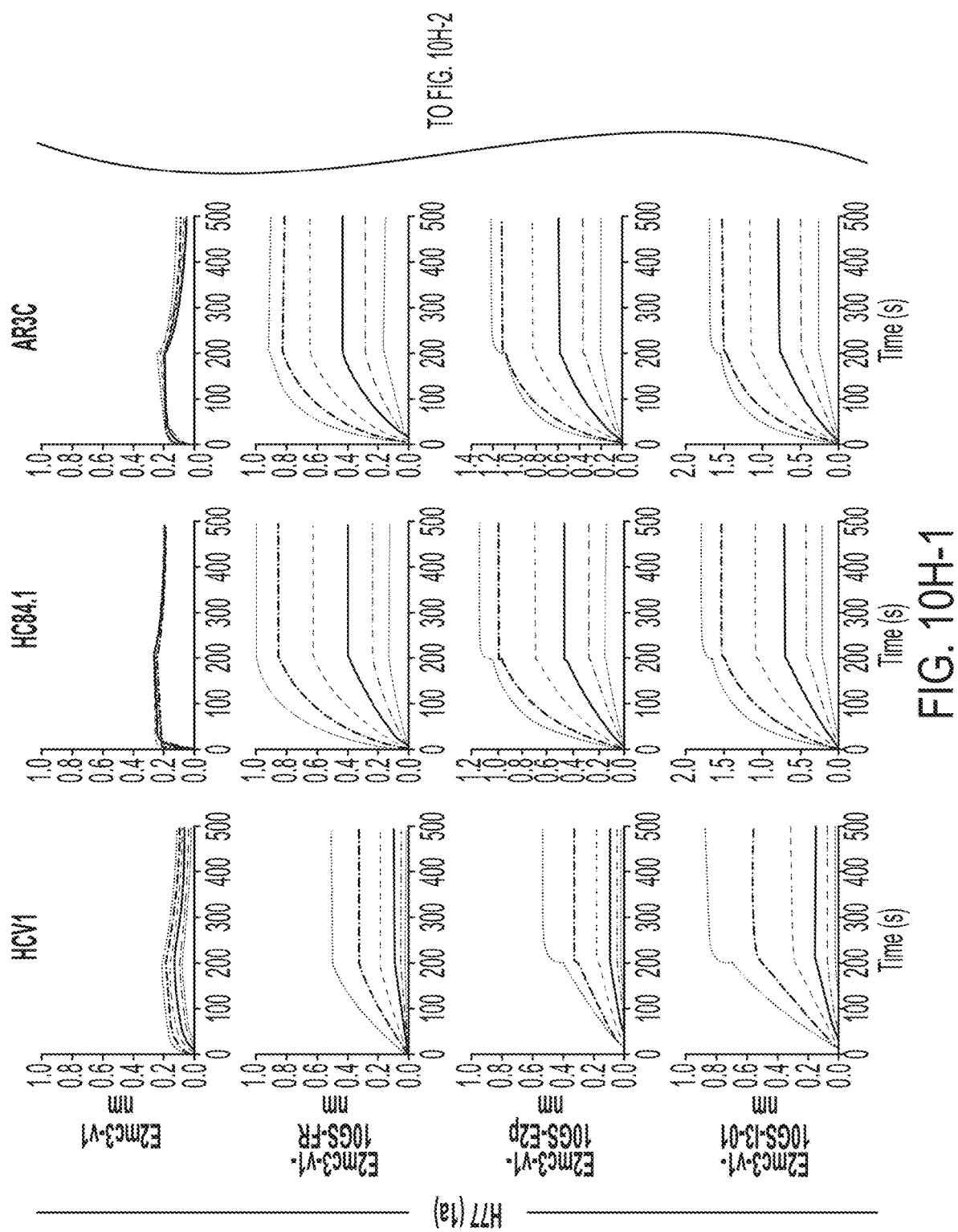
Figures 2, 10H:
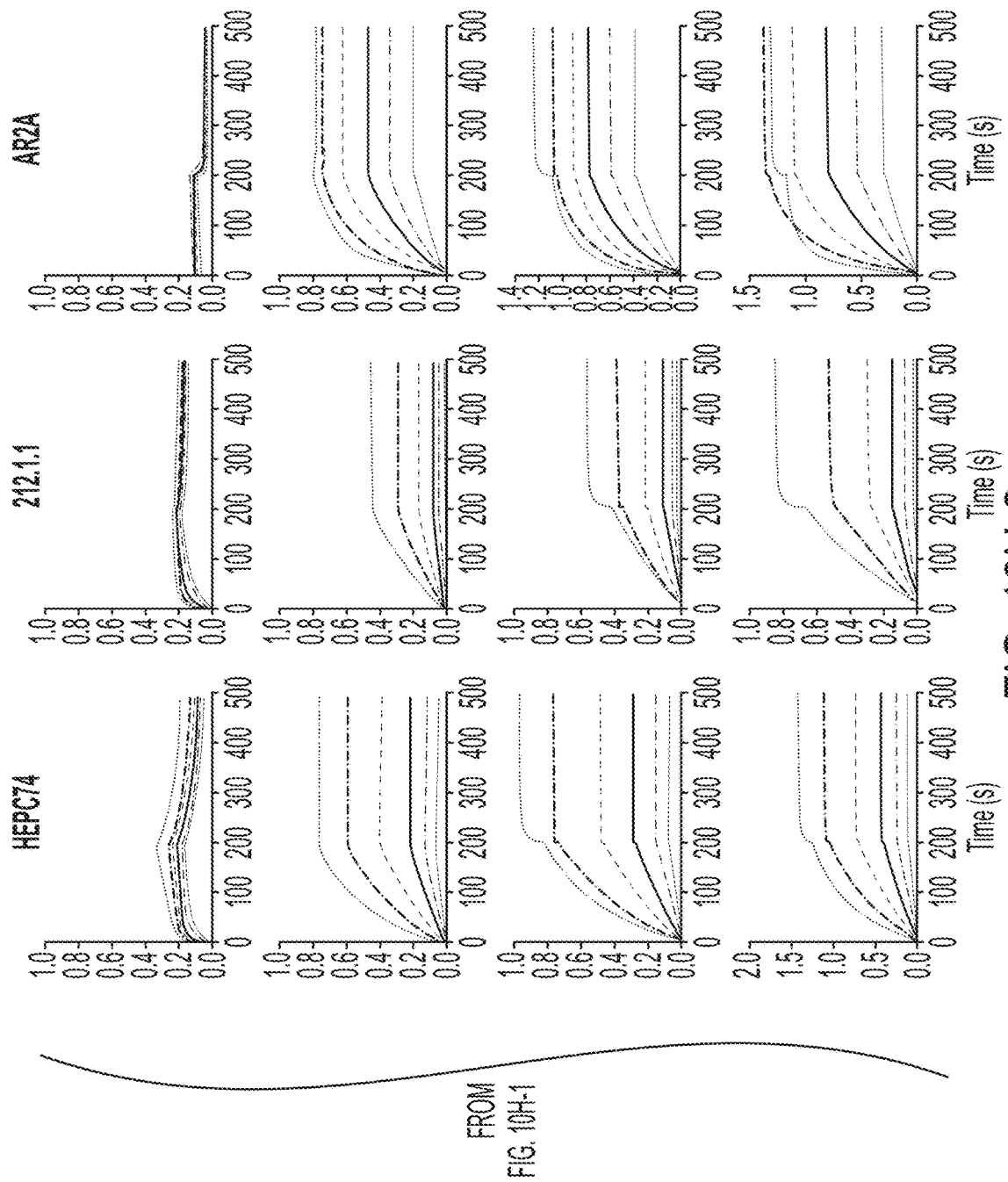
Figures 1, 10I:
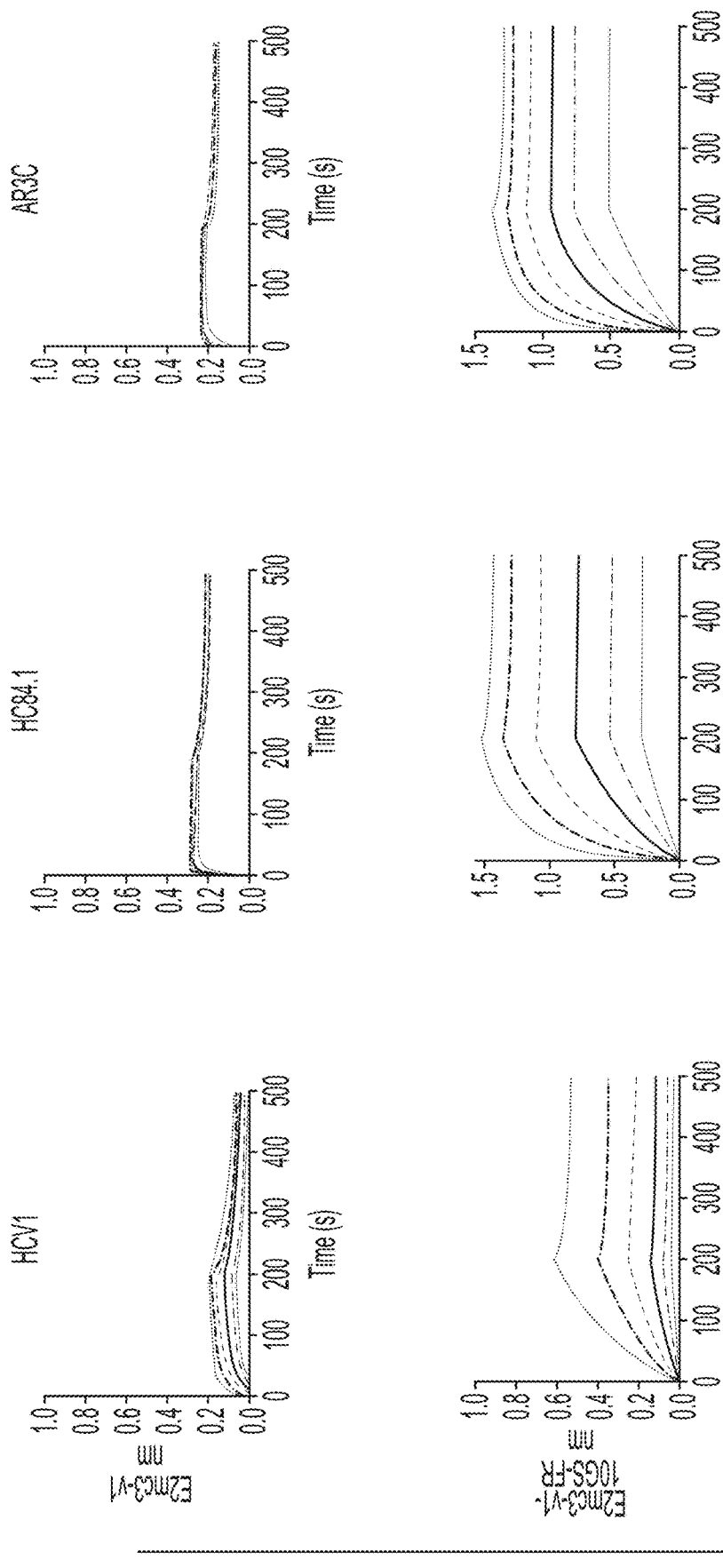
Figures 3, 10I:
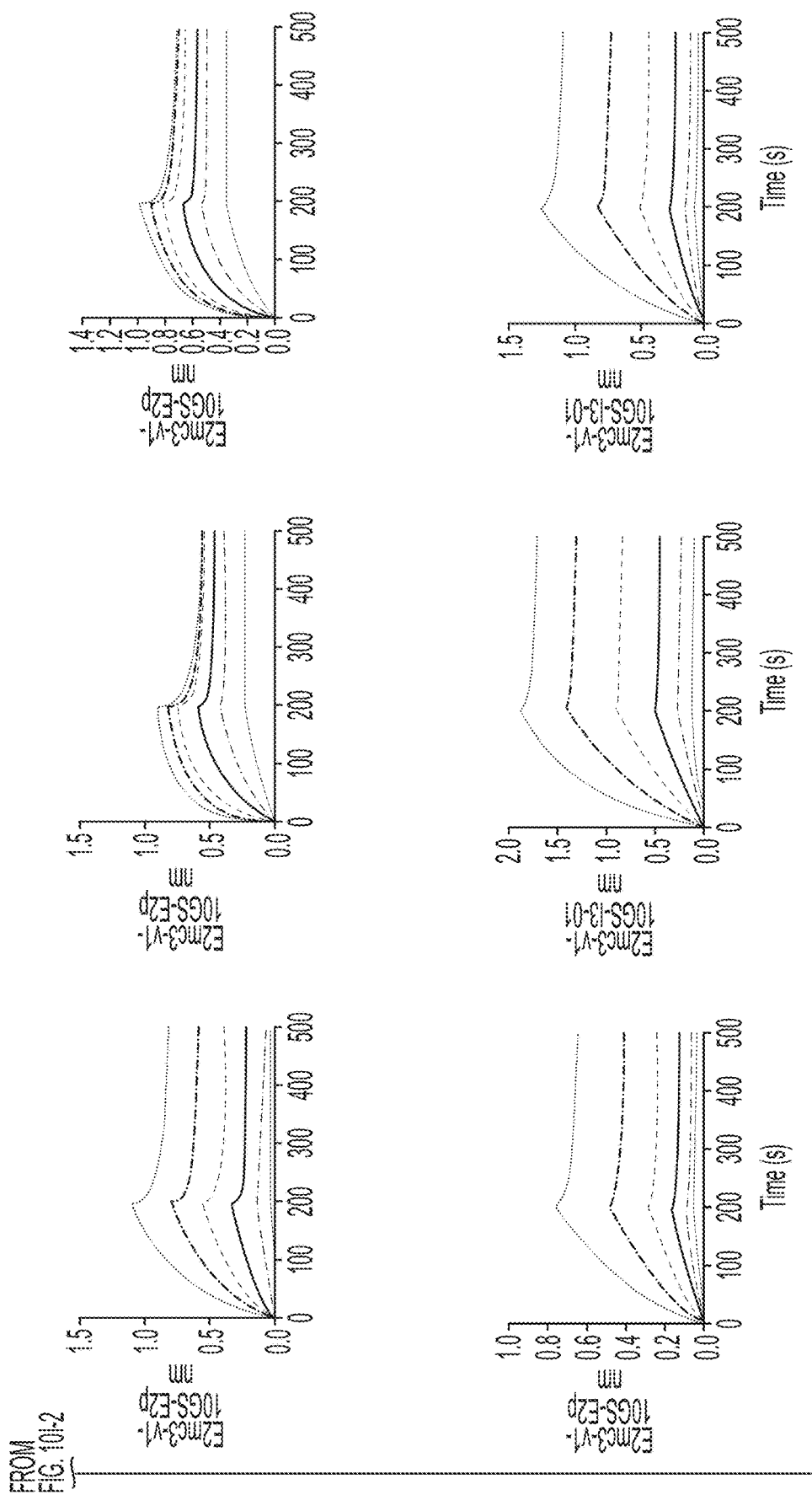
Figures 4, 101:
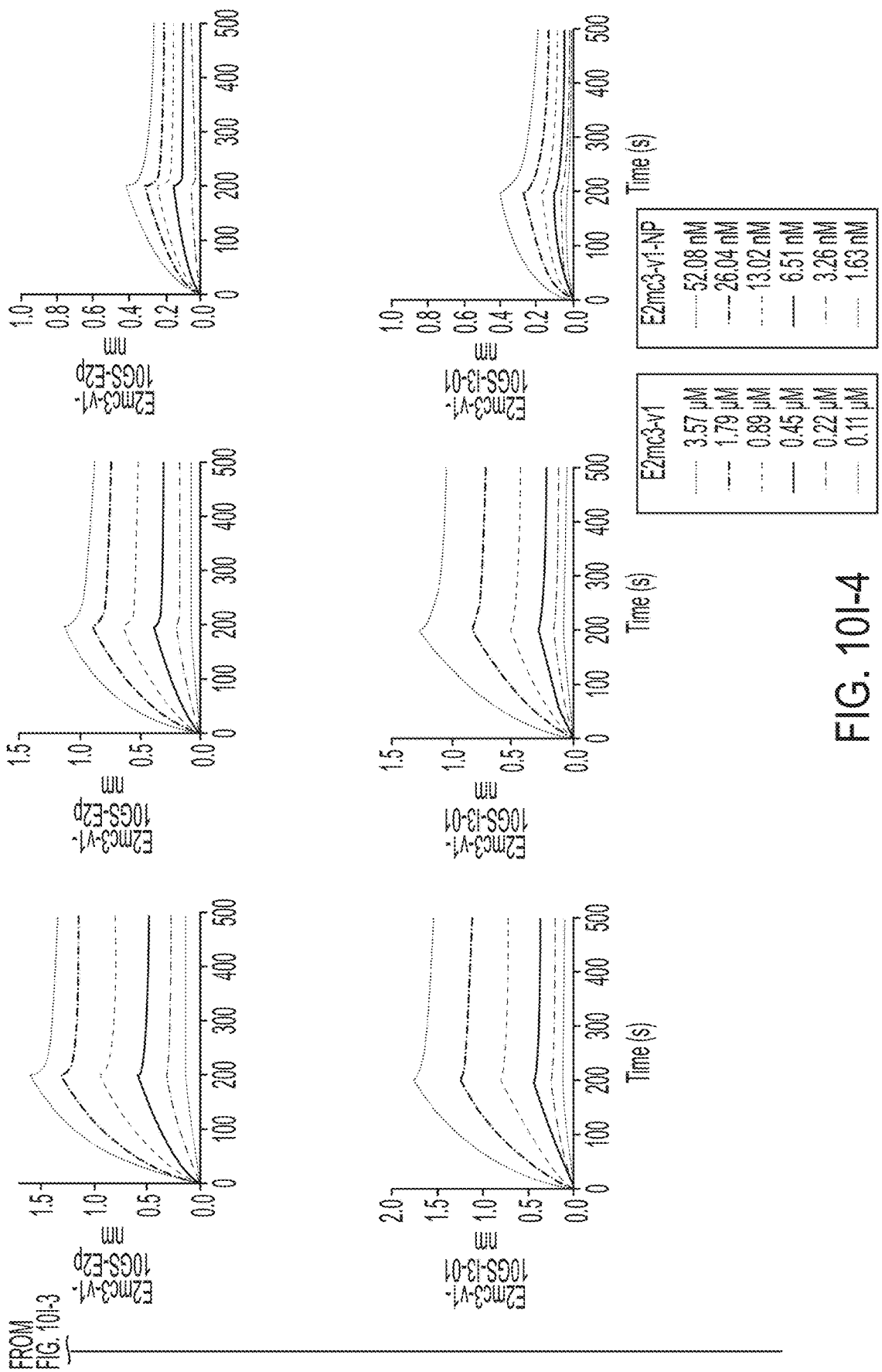

Example 4 Design and Characterization of Nanoparticles Presenting Optimized E2 Cores Recently, improved immunogenicity in mice was reported for a ferritin nanoparticle carrying soluble E2 (sE2, a.a. 384-661) that contains three full-length immunodominant variable loops (Yan et al., J. Infect. Dis. [Epub ahead of print], 2019). Here, we displayed our E2mc3 variants, which only present the conserved bNAb epitopes, on self-assembling nanoparticles as multivalent HCV vaccine candidates (FIG. 3A). We tested three nanoparticle platforms: 24-meric ferritin (FR, as control) and 60-meric E2p and I3-01, ranging in size from 24.5-37.5 nm (FIG. 3B). We genetically fused the C-terminus of E2mc3-v1 to the N-terminus of a nanoparticle subunit via a 10-residue linker, $(G4S)_2$. Six constructs were transiently expressed in ExpiCHO or 293 F cells and purified on the AR3A column followed by SEC (FIG. 3C and FIG. 10A). For H77, the SEC profiles demonstrated substantial yield and purity for all E2 core nanoparticles with different patterns for 24-vs. 60-mers (FIG. 3C). For HK6a, reduced nanoparticle yield and purity was accompanied by increased low-molecular-weight species (FIG. 10A), suggesting that H77 tVR2 may be incompatible with HK6a and hinder particle assembly. However, effective particle assembly was observed in both blue-native PAGE (BN-PAGE) and negative-stain electron microscopy (EM) (FIGS. 3D and 3E; FIGS. 10B and 10C), as well as enhanced bNAb binding to H77 nanoparticles (up to 100-fold change in $EC_{50}$) and no binding to non-NAbs targeting the β-sandwich loop (FIG. 3F and FIGS. 10D-1 to 10G). HK6a E2mc3-v1 nanoparticles exhibited similar but genotype-specific profiles. In BLI, correlation between peak signal and antigen valency was observed irrespective of genotype with 60-mers>24-mer>E2 core monomer (FIG. 3G; FIGS. 10H-1 to 10I-4), consistent with our HCV gp140 nanoparticles (He et al., Sci. Adv. 4, eaau6769, 2018).

Example 5 E2 Core Nanoparticles Elicit Stronger Immune Responses than E2 Cores

Figure 4A:
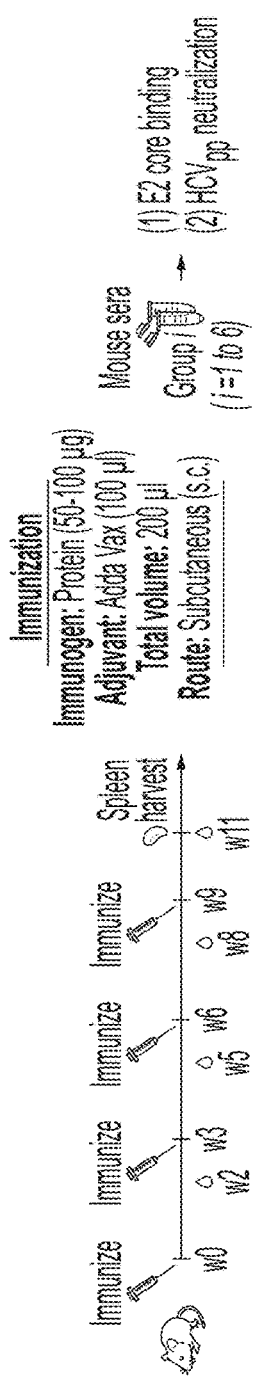
FIGS. 4A-4E show immunogenicity of newly designed E2 cores and nanoparticles in mice. (4A) Schematic representation of the mouse immunization protocol. In study #1, mice were immunized with H77 E2mc3-v1 (group 1), H77 E2mc3-v1-10GS-FR (group 2), and H77 E2mc3-v1-10GS-E2p (group 3). In study #2, mice were immunized with HK6a E2mc3-v1 (group 1), HK6a E2mc3-v1-10GS-E2p (group 2), and HK6a/H77 E2mc3-v1-10GS-E2p mix (group 3). (4B) Longitudinal analysis of E2-specific antibody titers in immunized mouse sera at weeks 2, 5, 8 and 11. Top panel: $EC_{50}$ values calculated from ELISA binding of mouse sera in study #1 to the coating antigen, H77 E2mc3-v1. Bottom panel: $EC_{50}$ values calculated from ELISA binding of mouse sera in study #2 to the coating antigens HK6a E2mc3-v1 (groups 1-3) and H77 E2mc3-v1 (group 3). The P-values were determined by an unpaired t test in Prism and are labeled on the plots, with (*) indicating the level of statistical significance. Detailed serum ELISA data is shown in FIG. 11, A-D. (4C) Mouse serum neutralization in study #1. Top panel: Percent (%) neutralization of mouse sera against autologous H77 at weeks 2, 5, 8 and 11. Bottom panel: Percent (%) neutralization of mouse sera against heterologous HCV1, J6, and SA13 at the last time point, week 11. (4D) Mouse serum neutralization in study #2. Percent (%) neutralization of mouse sera against heterologous H77 at weeks 2, 5, 8 and 11. (4E) Validation of the HCV pseudotyped particle (HCVpp) neutralization assay using five HCV bNAbs and an HIV-1 bNAb (negative control). Percent (%) neutralization of all antibodies was determined at three concentrations, 10.0n/ml, 1.0 µg/ml, and 0.1 µg/ml.
Figure 4B:
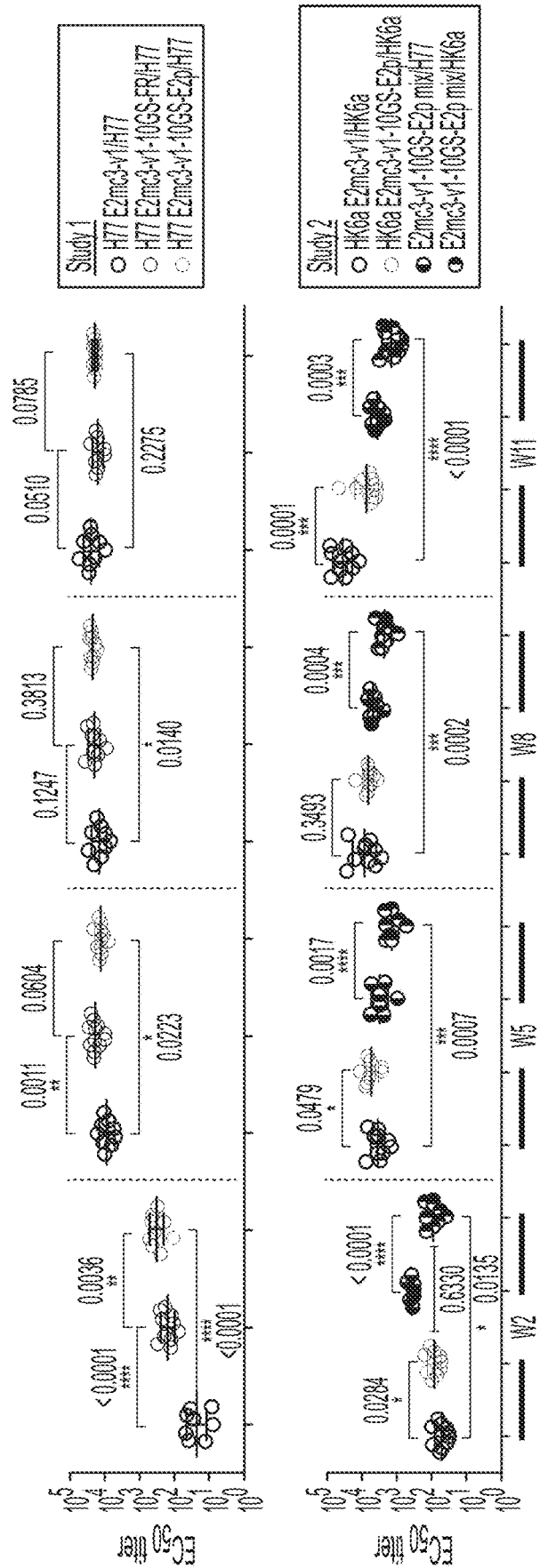
Figure 4C:
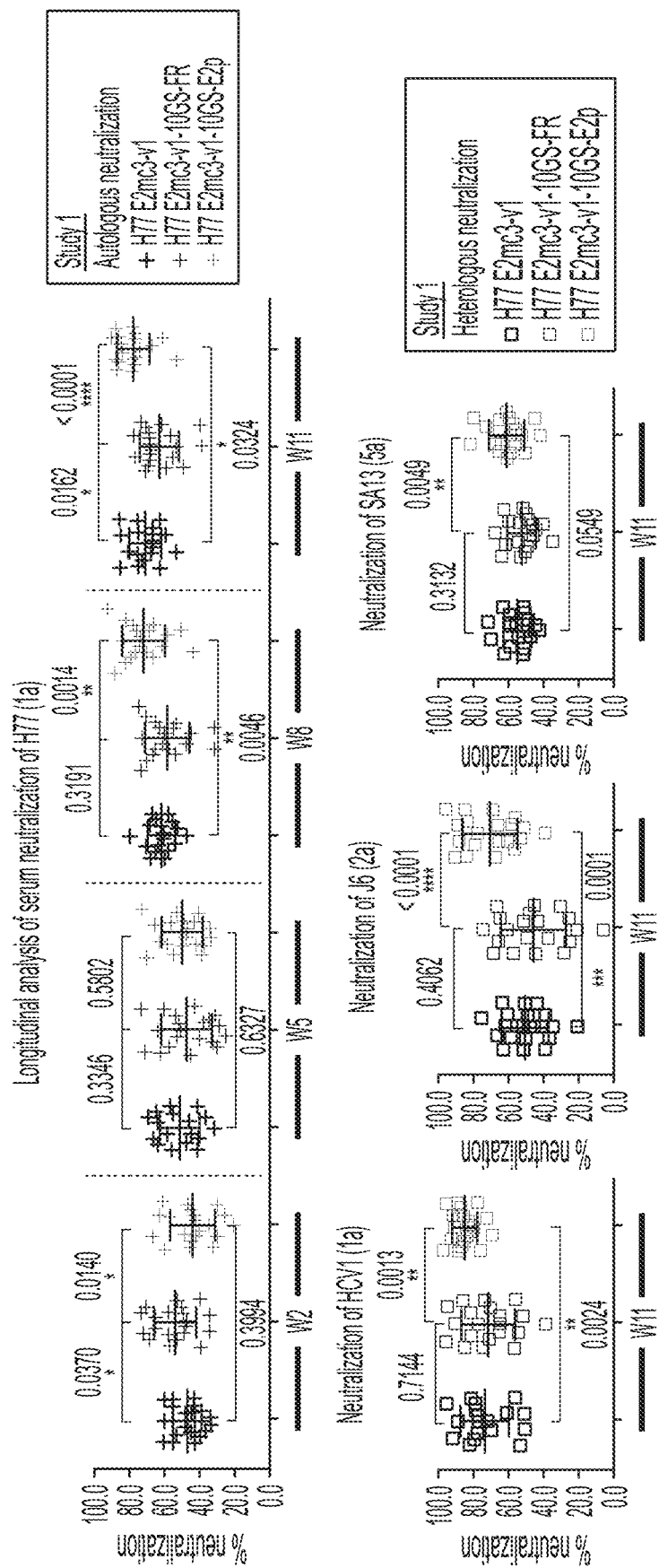
Figure 4D:
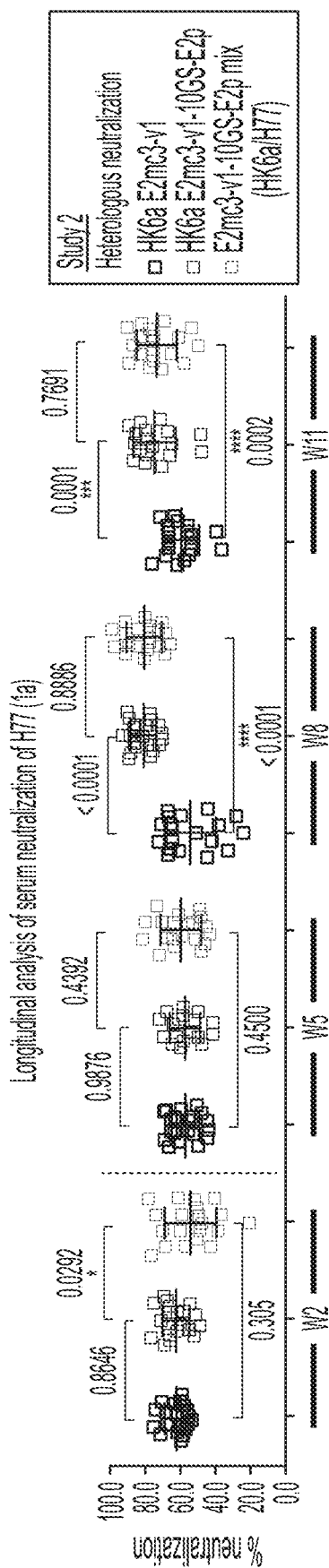
Figure 4E:
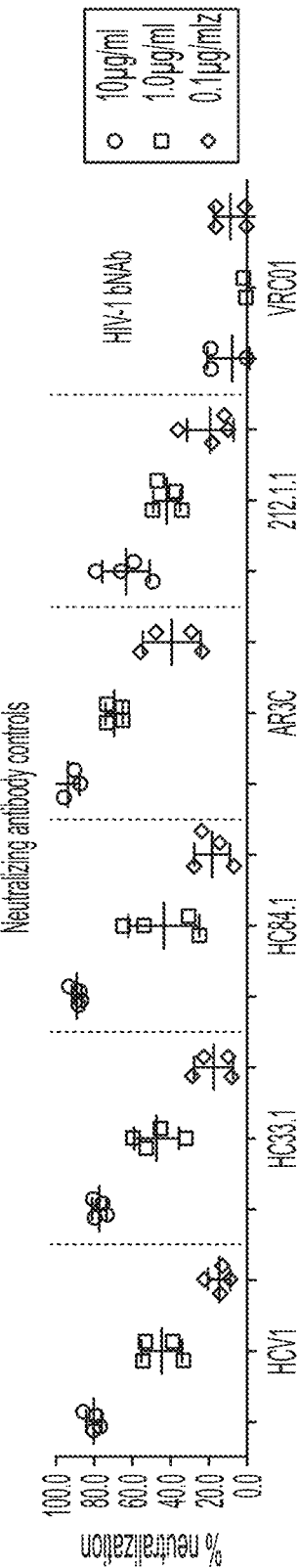
Figure 11A:
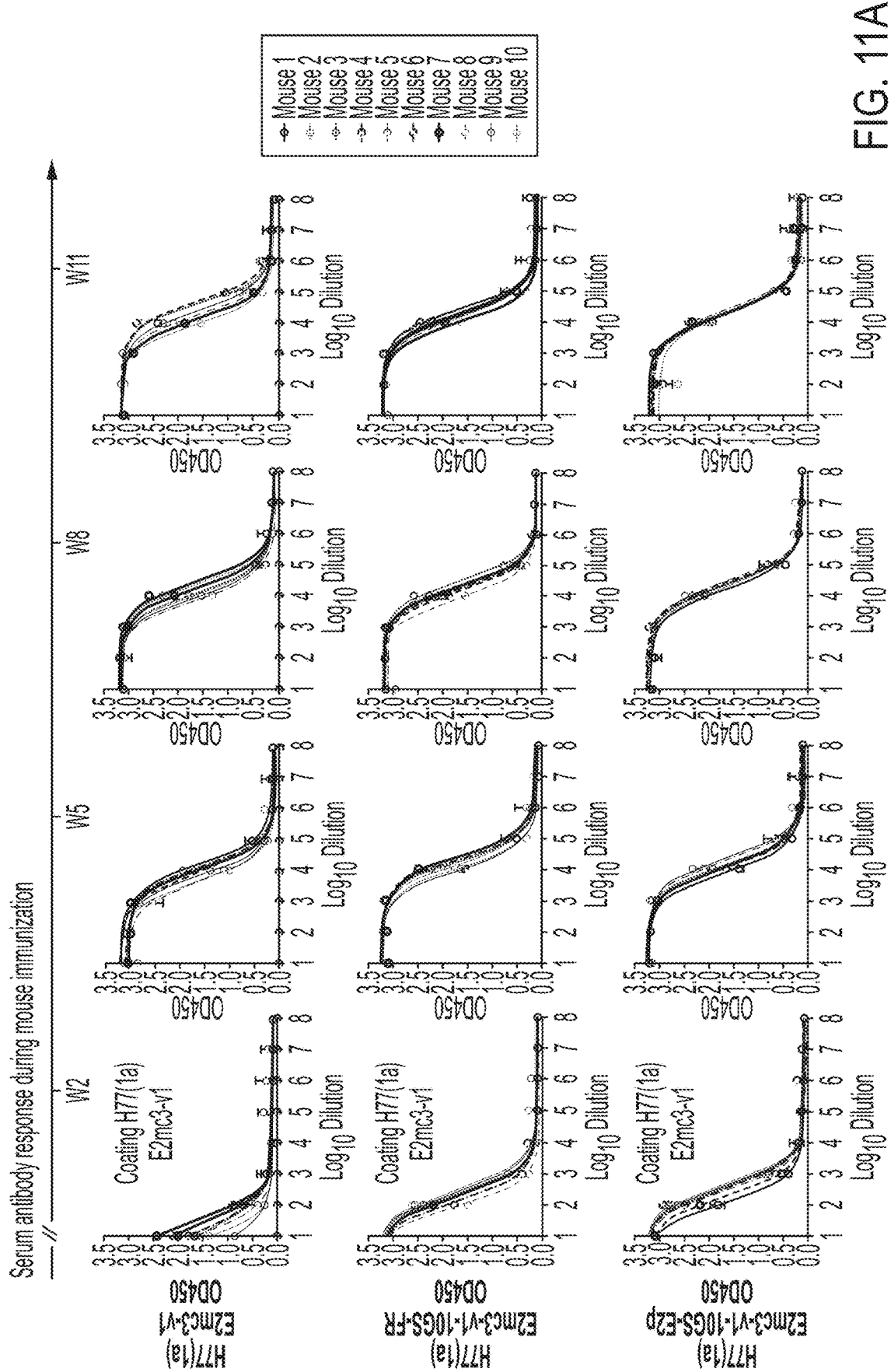
Figures 1, 11C:
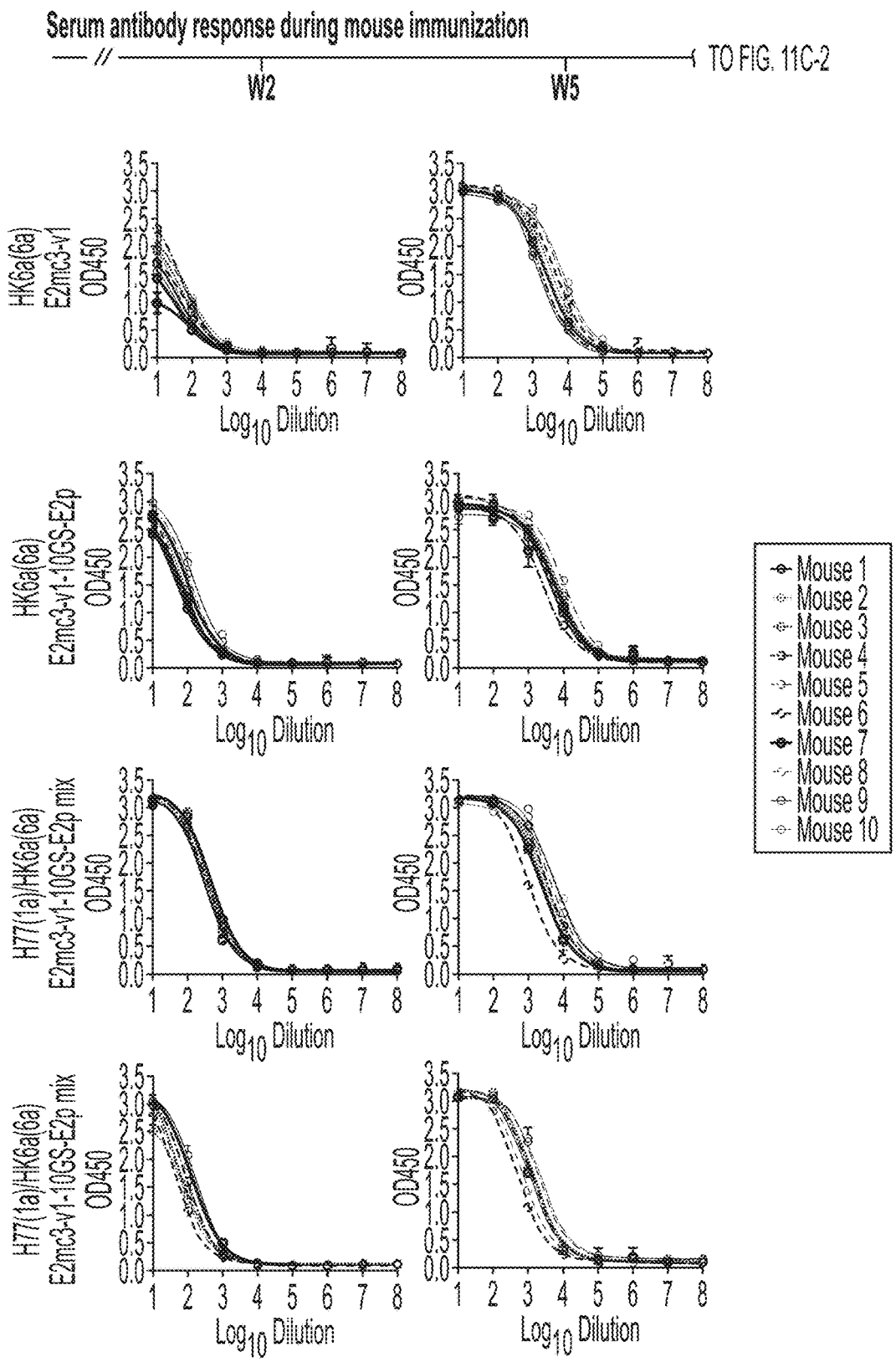
Figures 2, 11C:
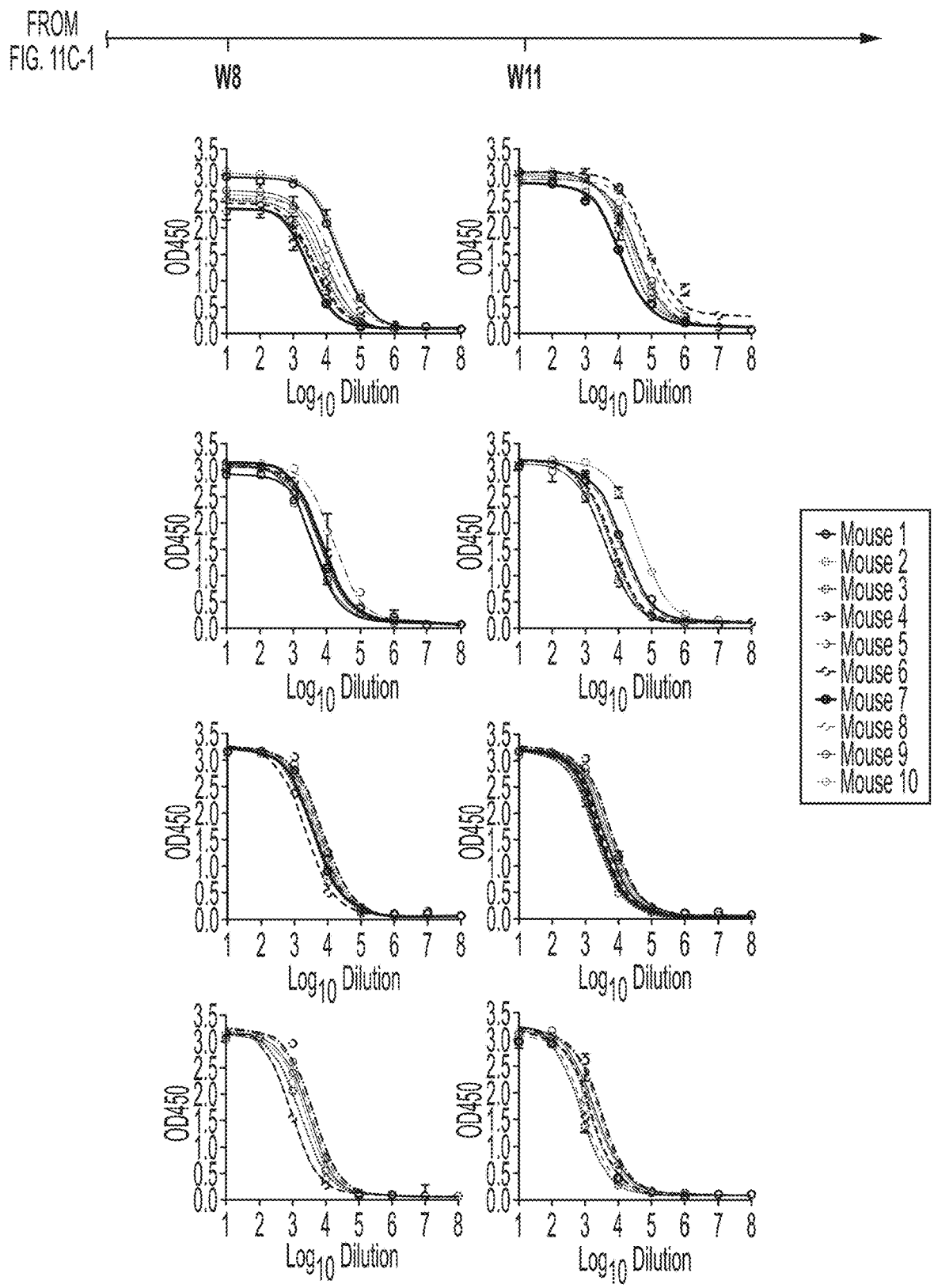

We assessed H77 and HK6a E2 core nanoparticles in wild-type BALB/c mice in studies #1 and #2, respectively, using a short regimen (FIG. 4A). N. 2, I3-01-based constructs were not included due to the difficulties in producing HK6a E2mc3-v1-10GS-I3-01 nanoparticles, as indicated by SEC (FIG. 10A). In study #1, three H77-based vaccines showed a correlation between E2-specific $EC_{50}$ titer and antigen valency at week 2 with significant P-values (FIG. 4B, upper panel; FIGS. 11A and 11B). While E2-specific antibody titers continued to rise, the difference between the three vaccine groups diminished at week 11. In study #2, we compared HK6a E2mc3-v1, its E2p nanoparticle, and HK6a/H77 E2mc3-v1 E2p nanoparticle mix (FIG. 4B, lower panel; FIGS. 11C-1 to 11D). The HK6a E2mc3-v1 E2p group retained its advantage in antibody titer until week 8, whereas its H77 counterpart did until week 11. The E2p mix elicited significantly higher titers to H77 than to HK6a throughout the immunization. Overall, E2 core nanoparticles induced greater antibody titers than E2 cores, although E2 only accounts for 42% (E2p) to 51% (FR) of the protein mass. We then evaluated serum neutralization using HCV pseudoparticles (HCVpp). In study #1, autologous neutralization increased steadily over time with distinct temporal patterns (FIG. 4C, upper panel). At week 2, the FR group showed the highest H77 neutralization, whereas the E2p group was unexpectedly the lowest (FIG. 4B, upper panel). From week 5, the FR grouped show lower neutralizing activity with a significant P-value at week 11, whereas the E2p group became the best performer with statistical significance at weeks 8 and 11. Week 11 sera also neutralized heterologous isolates HCV1 (1a), J6 (2), and SA13 (5a), with significant P-values for HCV1 and J6 (FIG. 4C, lower panel). A similar trend was observed for group #2 (FIG. 4D), and the E2p mix group was equivalent to the HK6a-only E2p group. Five HCV bNAbs and HCV bNAb VRC01 validated the HCVpp assays (FIG. 4E).

Figure 5A:
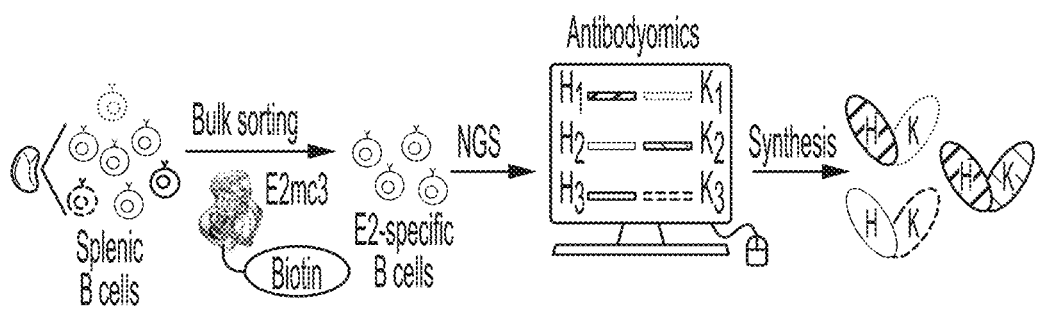
FIGS. 5A-5G show patterns associated with HCV E2-specific B cell response in mouse immunization. (5A) Schematic representation of the strategy used to analyze HCV E2-specific B cell response that combines antigen-specific bulk sorting of splenic B cells with next-generation sequencing (NGS) and antibodyomics analysis. (5B) Statistical analysis of B cell sorting data obtained for group 1 (H77 E2mc3-v1 monomer) and group 3 (H77 E2mc3-v1-10GS-E2p nanoparticle) in study #1. Left: Frequency of E2-specific B cells. Right: Number of E2-specific B cells per million splenic cells. Five mice from group 1 (M1, M3, M5, M6 and M10) and five mice from group 3 (M5, M7, M8, M9, and M10) were randomly selected and analyzed. (5C) Distribution of germline gene usage plotted for group 1 and group 3. Top panel: Germline $V_H$ genes. Bottom panel: Germline $V_K$ genes. Statistical analysis of number of activated $V_H/V_K$ genes (1% of the total population) is shown on the far right. (5D) Distribution of germline divergence or degree of somatic hypermutation (SHM) plotted for groups 1 and 3. For each group, percent (%) mutation is calculated at the nucleotide (nt) level for $V_H$ (left) and $V_K$ (right). Statistical analysis of germline divergence is shown on the far right. (5E) Distribution of CDR3 loop length plotted for groups 1 and 3. For each group, CDR3 length calculated at the amino acid (a.a.) level is shown for heavy (left) and light chains (right). Statistical analysis of root-mean-square fluctuation (RMSF) of CDR3 loop length, which is used as an indicator of how much the CDR3 loop length varies within the E2-specific antibodies from each animal. (5F) Neutralization curves using purified IgG for groups 1 (left) and 3 (right) in study #1. Autologous H77 (1a) and heterologous SA13 (5a) were tested in HCVpp assays with a starting IgG concentration of 100 µg/ml followed by a series of three-fold dilutions. Structural models of the immunogens are placed next to their neutralization curves. (5G) Epitope mapping of polyclonal antibody sera from groups 1 and 3 in study #1. Surface model of a truncated E2 ectodomain ($E2_{ECTO}$) (PDB: 6MEI) is shown in the middle with the front layer (FL) and AS412. Statistical analysis of $EC_{50}$ titers of groups 1 and 3 against the FL probe (left) and the AS412 probe (right). Structural models of the designed nanoparticle probes are placed next to their plots. Epitopes on the nanoparticles are colored according to the truncated $E2_{ECTO}$ model (PDB: 6MEI).
Figure 5B:
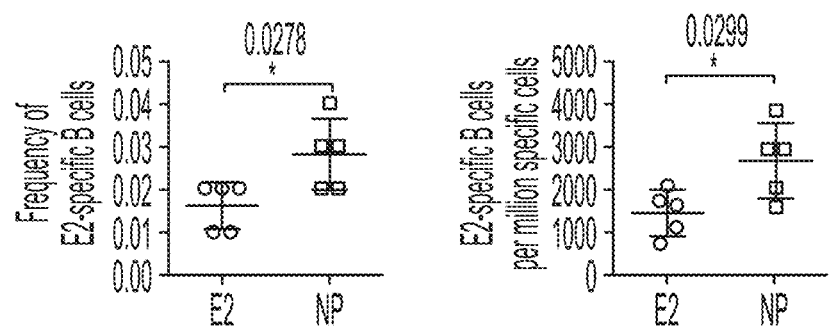
Figure 5C:
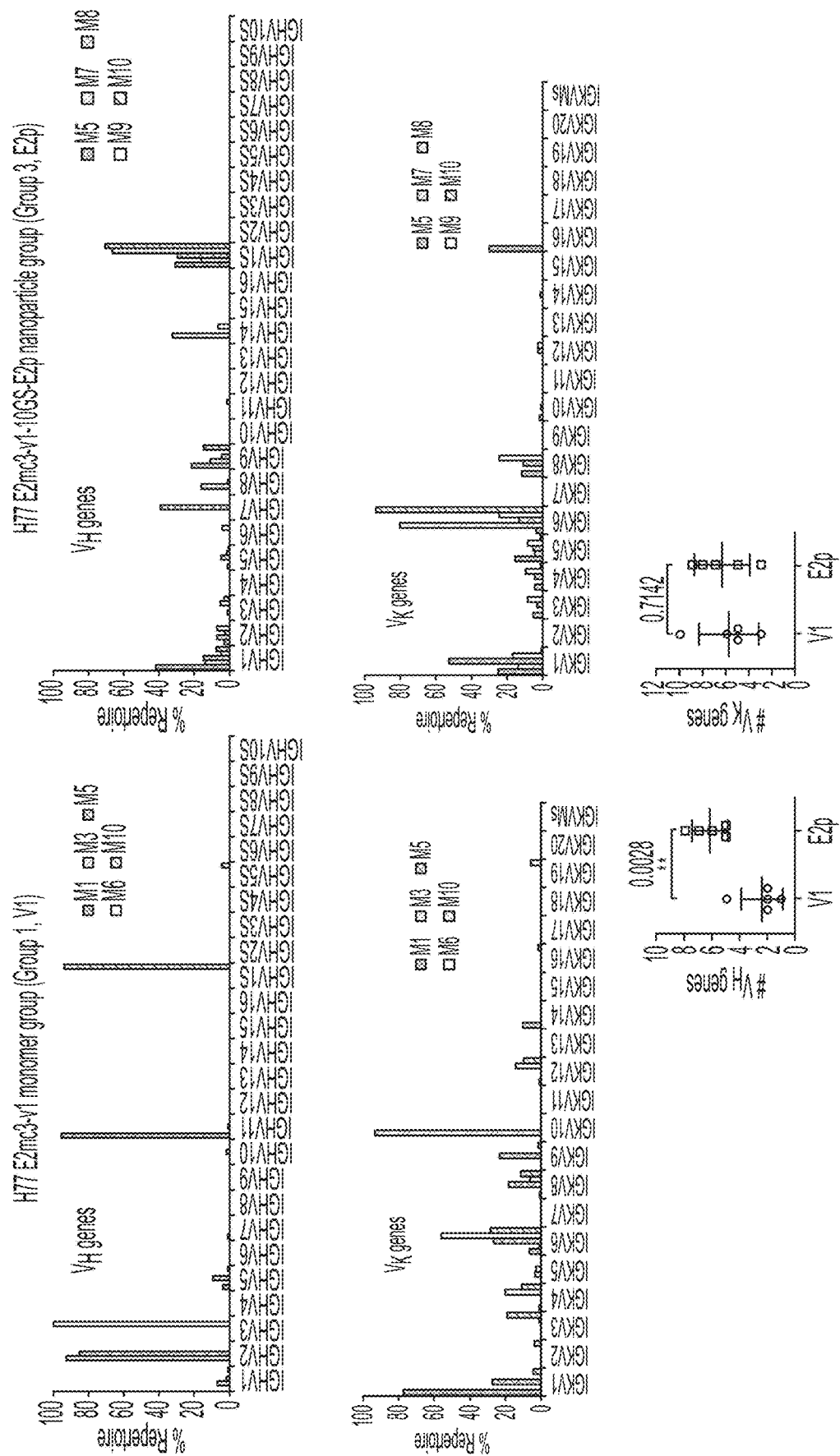
Figure 5D:
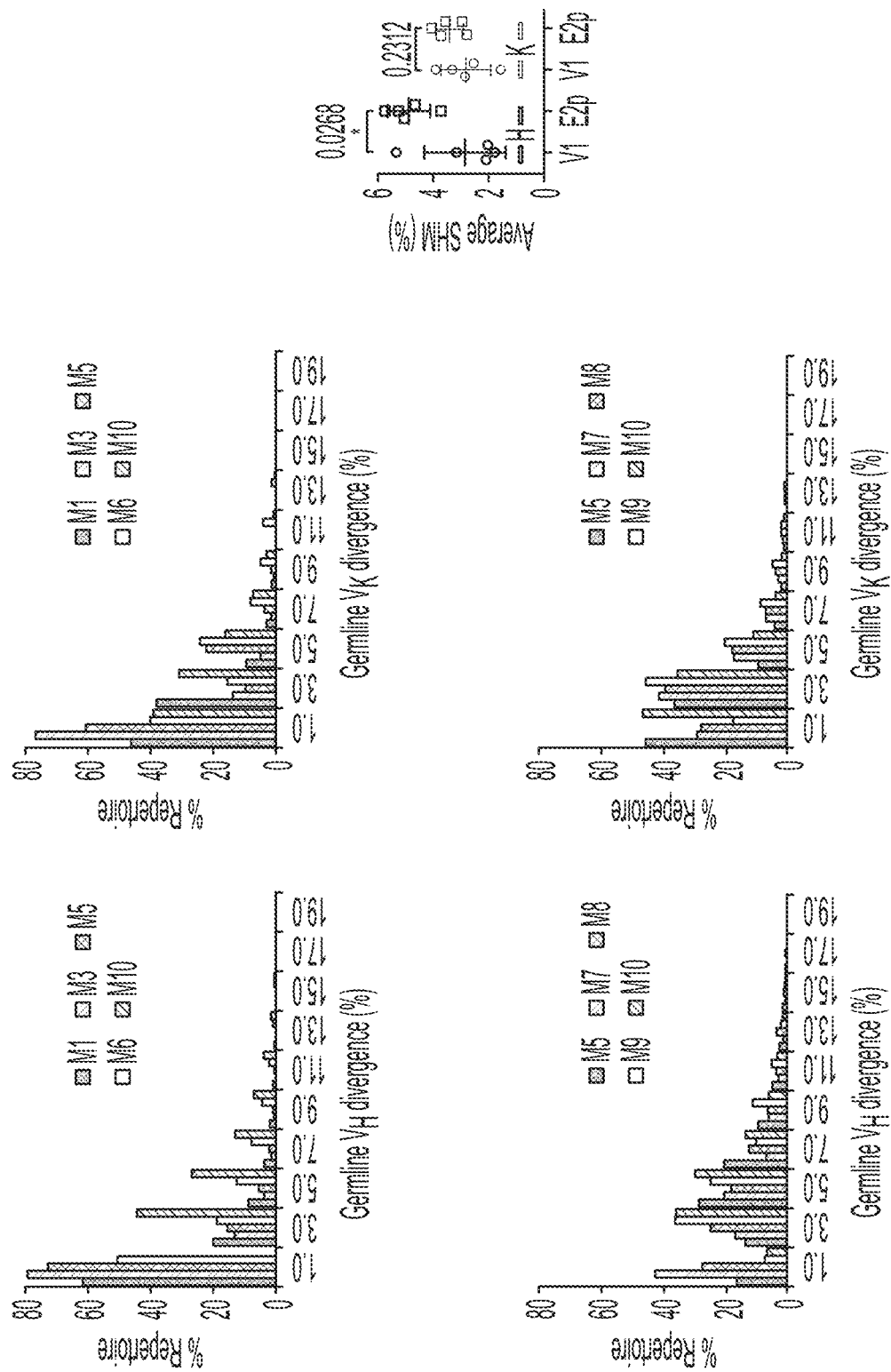
Figure 5E:
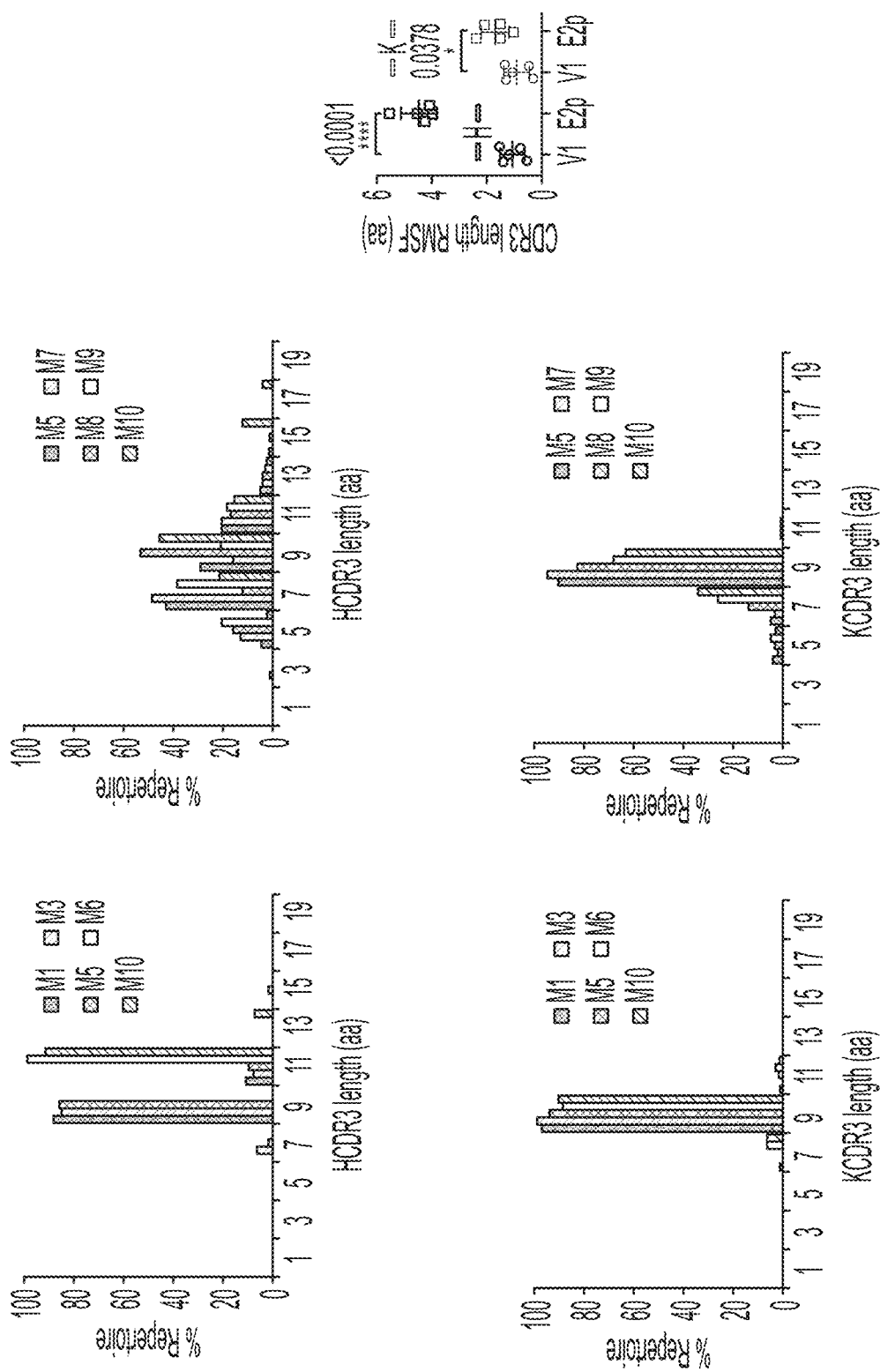
Figures 12A, 12B:
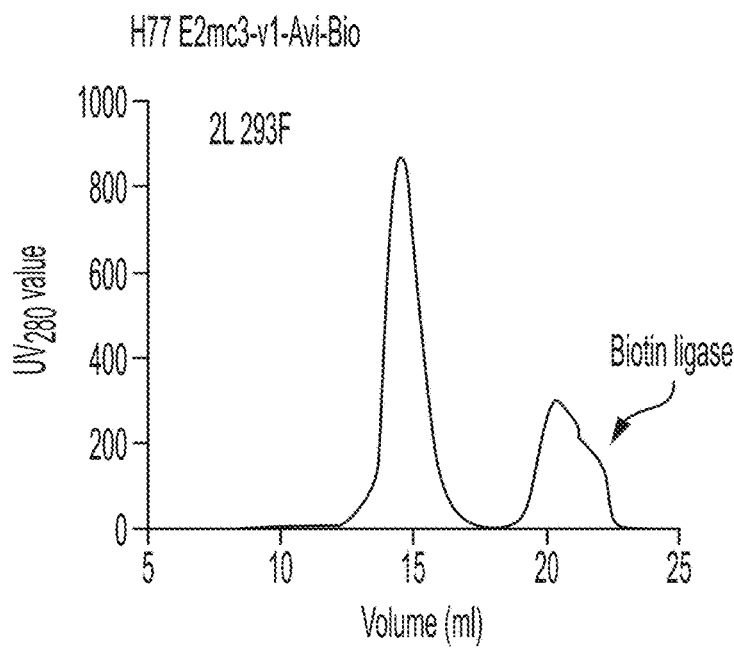

Example 6 Distinctive Patterns of E2 Core and Nanoparticle Induced B Cell Response We combined antigen-specific B cell sorting and antibody NGS to obtain a quantitative readout of vaccine-induced B cell responses and determine B cell patterns associated with different vaccine platforms (FIG. 5A). We used an H77 E2mc3-v1 probe with an C-terminal Avi-tag (FIG. 12A) to sort E2-specific splenic B cells from mice in the H77 E2mc3-v1 and E2p nanoparticle groups by flow cytometry. A greater frequency/number of E2-specific B cells was observed for the E2p group with significant P-values (FIG. 5B and FIG. 12B). Sorted B cells from 10 mice, five per group, were subjected to next-generation sequencing (NGS) analysis and repertoire profiling (FIG. 12C). The E2p group used significantly more (5 to 8) heavy-chain variable ($V_H$) genes than the E2 core group (~1) (FIG. 5C), Antibodies elicited by E2p contained more $V_H$ mutations with a significant P-value of 0.0268 (FIG. 5D), Distinct patterns of HCDR3 length were observed for the two groups with the E2 core group showing two dominant HCDR3 lengths, while the E2p group produced a much broader distribution (FIG. 5E). The E2p group yielded a greater average RMSF—the range in which the loop length varies than the E2 core group (4.5aa vs. 1.1aa) with a P-value of <0.0001.

Example 7 NAbs Induced by E2 Core and E2 Nanoparticle Target Different Epitopes

Figure 5F:
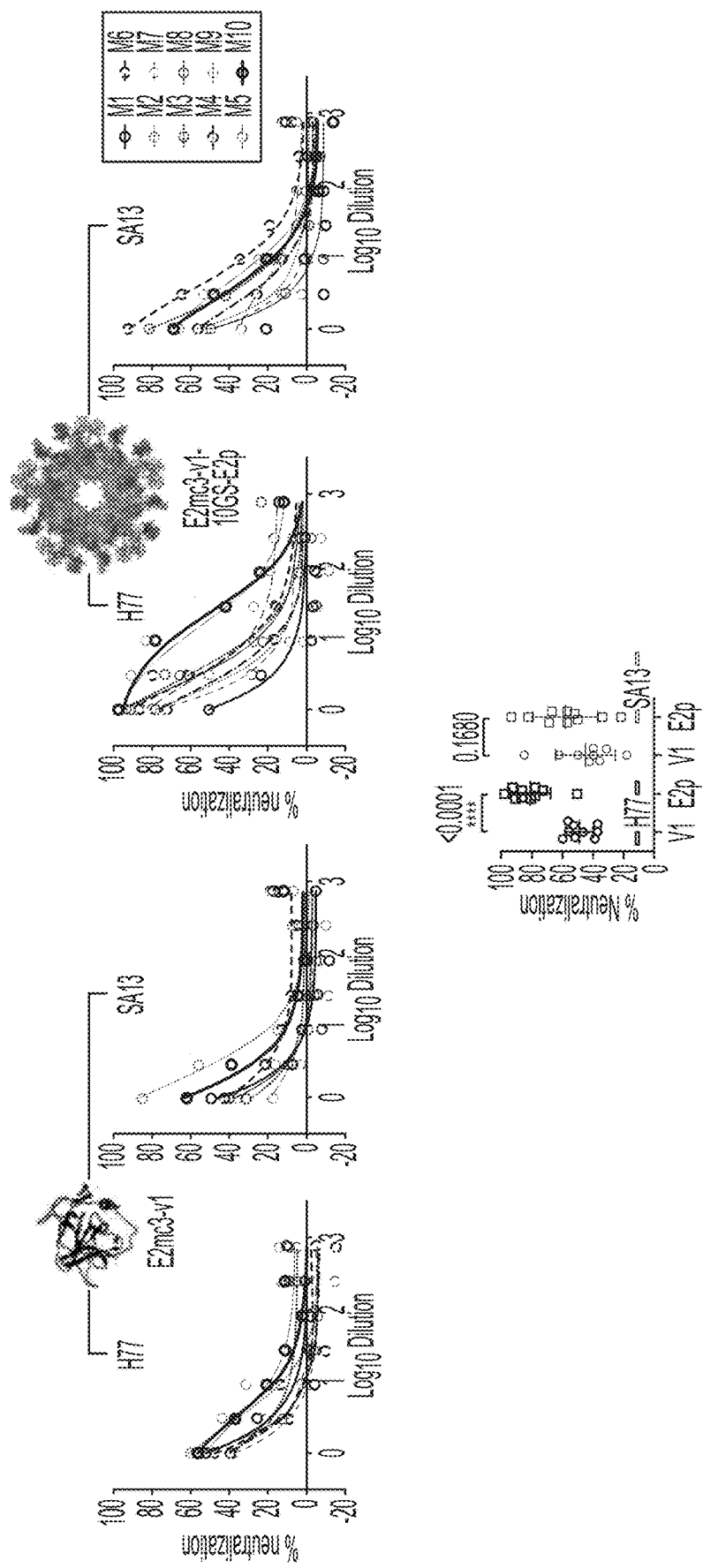
Figure 5G:
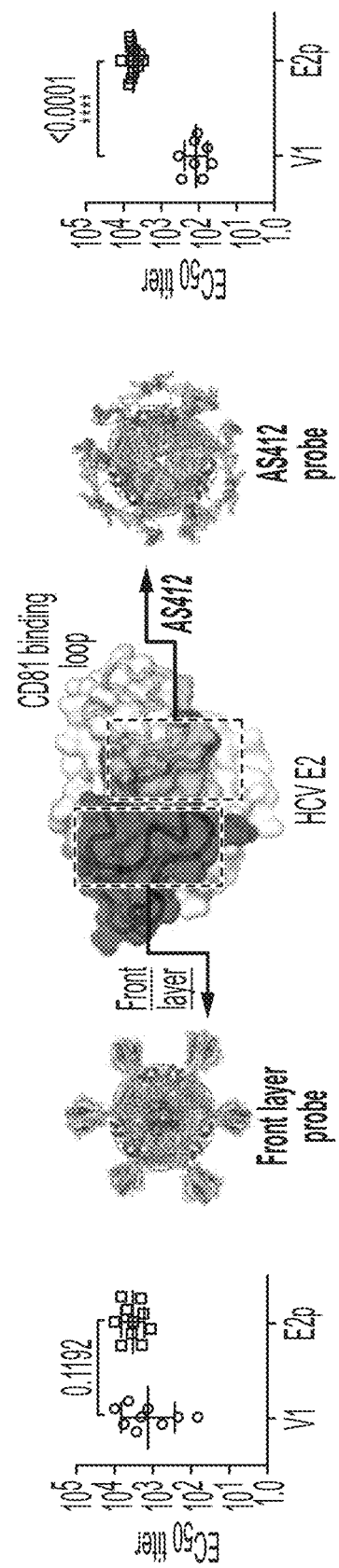
Figure 13C:
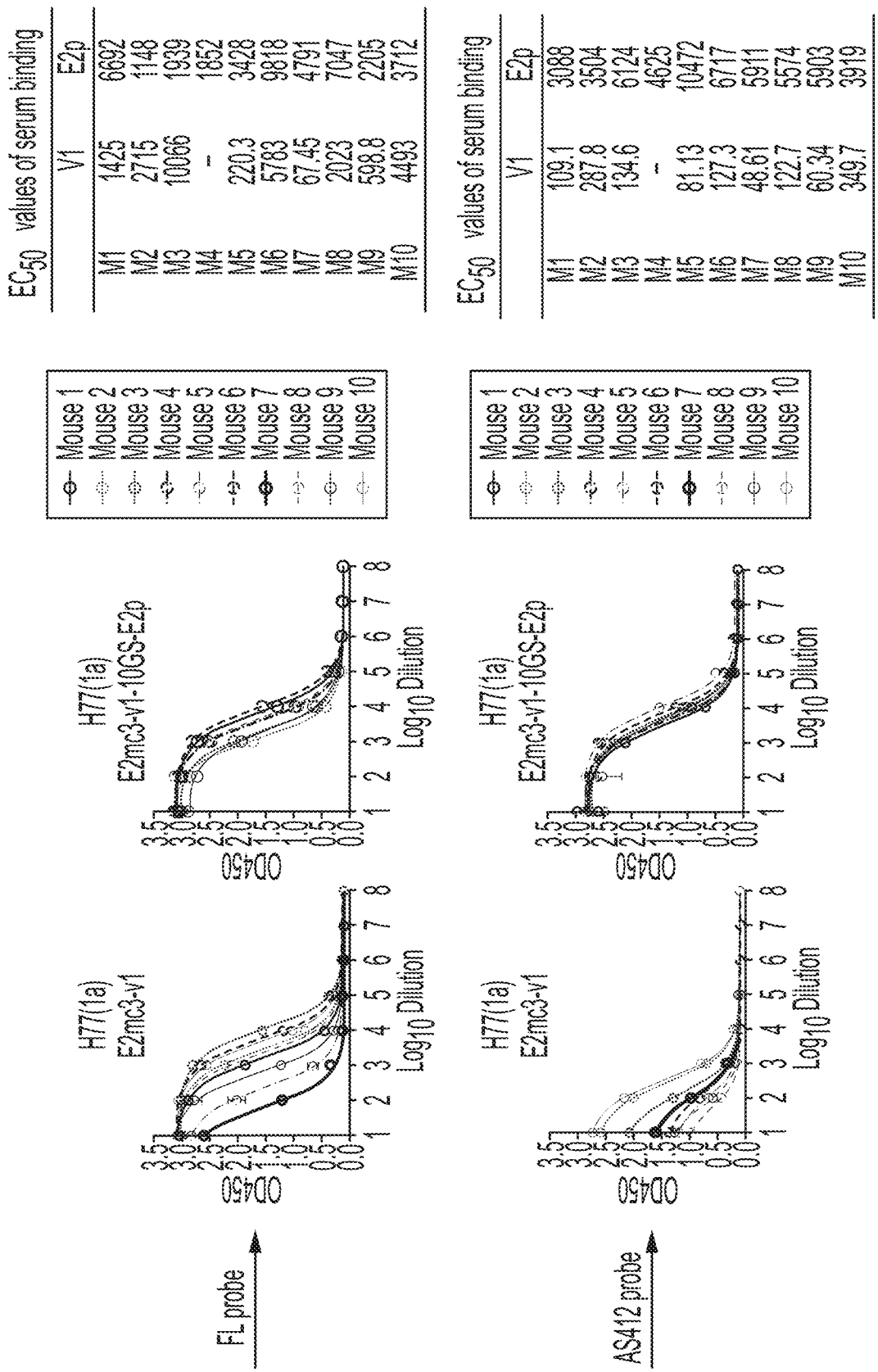

Mouse serum contains nonspecific antiviral activity, which may interfere with HCVpp assays. We purified mouse IgG from study #1 at week 11 for neutralization of H77 and SA13 HCVpps with starting IgG at 100 µg/ml followed by a series of three-fold dilutions (FIG. 5F and FIG. 13A). For H77, while no mice sera in the E2 core group neutralized >60% viruses at the first concentration, mice #9 and #10 in the E2p group showed plateaued curves, suggesting potent NAbs in the IgG, with a similar but less pronounced trend for SA13. Unpaired t tests indicated a significant difference between E2p and E2 core groups for H77 (P<0.0001), but not for SA13 (P=0.1680). The FR group ranked the lowest in serum neutralization but slightly outperformed E2 core in IgG neutralization (FIG. 13A). Nonetheless, ferritin (FR) may not be an optimal platform for HCV nanoparticle vaccine design. Here, two epitope-specific probes were used to examine vaccine-induced antibody responses to two prominent bNAb epitopes: front layer (FL, a.a. 421-459), integral to the E2 neutralizing face (Tazrum et al., Front. Immunol. 9, 1315, 2018), and AS412 (FIG. 5G, middle). A trimeric scaffold was designed to present FL, which was anchored to each subunit via an engineered disulfide bond (FIG. 13B). This trimer FL-scaffold was displayed on FR. In ELISA, the E2p group yielded an average $EC_{50}$ titer of 4281 compared to 3044 for the E2mc3-v1 group (FIG. 5G, left and FIG. 13C). However, unpaired t test reported a non-significant P-value, 0.1192, between the two groups (FIG. 5G, left). Nonetheless, nanoparticle display improved recognition of FL including antigenic site 434 (AS434, a.a. 434-446). We then used a previously designed FR nanoparticle (He et al., Sci. Rep. 5:12501, 2015) (FIG. 13B, bottom) to probe AS412-specific response. In ELISA, the E2p group demonstrated a uniform, robust response to the β-hairpin of AS412 with an average $EC_{50}$ titer of 5584, which is 38-fold greater than the E2 core group with a P-value of <0.0001 (FIG. 5G, right and FIG. 13C, bottom). Thus, particulate display focuses the response on conserved bNAb epitopes. These epitope probes also provide valuable tools for epitope mapping for assessment of HCV vaccine candidates.

Example 8 Some Exemplified Materials and Methods

Structural design of truncated VR2 (tVR2): Based on the structure of bNAb AR3C-bound H77 E2c (PDB ID:

4MWF), the already shortened VR2 loop in E2c, i.e. the segment between C452 and C494, was manually truncated by removing exposed hydrophobic residues and a disulfide bond (C459-C486), resulting in the H77 E2mc3 construct (FIG. 6A). The truncated VR2 (tVR2) was modeled by the LOOPY (Xiang et al., Proc. Natl. Acad. Sci. U.S.A. 99:7432-7437, 2002), a torsion-space loop modeling and prediction program. Computational redesign of tVR2 was then performed using an ensemble-based de novo protein design method (Kong et al., Nat. Commun. 7:12040, 2016) with a focus on the N-terminal region of the peptide sequence PERASGHYPRP (SEQ ID NO:62) between C452 and C494. Briefly, an ensemble of 11-aa ($G_6$HYPRP) (SEQ ID NO:63) or 10-aa (G5HYPRP) (SEQ ID NO:64) loop conformations was generated to connect C452 and C494 using LOOPY. For each loop conformation, a starting sequence for the multi-glycine ($G_n$) region was selected from a pool of 50 random sequences based on the RAPDF potential (Zhu et al., Proteins 65, 463-479, 2006) and subjected to 500 steps of Monte Carlo simulated annealing (MCSA) with the temperature linearly decreasing from 300 to 10K. The lowest-energy sequence for each loop was recorded and all MCSA-derived designs were ranked based on energy at the completion of the process. The top 5 designs from the $G_6$ and $G_5$ ensembles, termed H77 E2mc3-v1-v5 and v6-10, respectively, were selected for experimental validation. HK6a E2mc3 and E2mc3-v1 constructs were designed by directly adopting the H77 sequence designs without further modification.

Expression and purification of E2 antigens: All E2 cores (E2c3, E2mc3, and E2mc3 v1-v10) and E2p-based nanoparticles were transiently expressed in HEK293 F cells (Thermo Fisher) for biochemical, biophysical, and antigenic analyses. Briefly, 293 F cells were thawed and incubated with FreeStyle™ 293 Expression Medium (Life Technologies, CA) in a shaker incubator at 37° C., 135 rpm and 8% $CO_2$. When the cells reached a density of $2.0\times10^6$/ml, expression medium was added to reduce cell density to $1.0\times10^6$/ml for transfection with polyethyleneimine (PEI) (Polysciences, Inc). Next, 900 μg of plasmid in 25 ml of Opti-MEM transfection medium (Life Technologies, CA) was mixed with 5 ml of PEI-MAX (1.0 mg/ml) in 25 ml of Opti-MEM. After 30-min incubation, the DNA-PEI-MAX complex was added to 1 L 293 F cells. Culture supernatants were harvested five days after transfection, clarified by centrifugation at 1800 rpm for 20 min, and filtered using a 0.45 μm filter (Thermo Scientific). E2 proteins were extracted from the supernatants using an AR3A antibody column as previously described (Long et al., *Science* 342, 1090-1094, 2013; and Tzarum et al., *Sci Adv* 5, eaav1882, 2019). Bound proteins were eluted three times, each with 5 ml of 0.2M Glycine (pH=2.2) and neutralized with 0.5 ml of Tris-Base (pH=9.0). The proteins were further purified by size exclusion chromatography (SEC) on a Superdex 75 Increase 10/300 GL column (GE Healthcare) for E2 cores and on a Superose 6 10/300 GL column (GE Healthcare) for E2p nanoparticles. E2mc3-v1-attached ferritin and I3-01 nanoparticles were produced in ExpiCHO cells (Thermo Fisher). Briefly, ExpiCHO cells were thawed and incubated with ExpiCHO™ Expression Medium (Thermo Fisher) in a shaker incubator at 37° C., 135 rpm and 8% $CO_2$. When the cells reached a density of $10\times10^6$ $ml^{-1}$, ExpiCHO™ Expression Medium was added to reduce cell density to $6\times10^6$ $ml^{-1}$ for transfection. The ExpiFectamine™ CHO/plasmid DNA complexes were prepared for 100-ml transfection in ExpiCHO cells following the manufacturer's instructions. For these two nanoparticles, 100 μg of plasmid and 320 μl of ExpiFectamine™ CHO reagent were mixed in 7.7 ml of cold OptiPRO™ medium (Thermo Fisher). After the first feed on day one, ExpiCHO cells were cultured in a shaker incubator at 32° C., 120 rpm and 8% $CO_2$ following the Max Titer protocol with an additional feed on day five (Thermo Fisher). Culture supernatants were harvested 13 to 14 days after transfection, clarified by centrifugation at 4000 rpm for 20 min, and filtered using a 0.45 μm filter (Thermo Fisher). The AR3C antibody column was used to extract E2mc3-attached nanoparticles from the supernatants, which was followed by SEC on a Superose 6 10/300 GL column. For E2 cores and nanoparticles, protein concentration was determined using $UV_{280}$ absorbance with theoretical extinction coefficients.

Blue native polyacrylamide gel electrophoresis (BN-PAGE): HCV E2 core nanoparticles were analyzed by blue native polyacrylamide gel electrophoresis (BN-PAGE) and stained with Coomassie blue. The protein samples were mixed with G250 loading dye and added to a 4-12% Bis-Tris NuPAGE gel (Life Technologies). BN-PAGE gels were run for 2.5 hours at 150 V using the NativePAGE™ running buffer (Life Technologies) according to the manufacturer's instructions.

Enzyme-linked immunosorbent assay (ELISA): Each well of a Costar™ 96-well assay plate (Corning) was first coated with 50 μl PBS containing 0.2 μg of the appropriate antigens. The plates were incubated overnight at 4° C., and then washed five times with wash buffer containing PBS and 0.05% (v/v) Tween 20. Each well was then coated with 150 μl of a blocking buffer consisting of PBS, 20 mg $ml^{-1}$ blotting-grade blocker (Bio-Rad), and 5% (v/v) FBS. The plates were incubated with the blocking buffer for 1 hour at room temperature, and then washed five times with wash buffer. In the mouse sample analysis, serum or plasma was diluted by 50-fold in the blocking buffer and subjected to a 10-fold dilution series. For each sample dilution, a total of 50 μl volume was added to the wells. Each plate was incubated for 1 hour at room temperature, and then washed five times with wash buffer. A 1:2000 dilution of horseradish peroxidase (HRP)-labeled goat anti-mouse IgG antibody (Jackson ImmunoResearch Laboratories) was then made in the wash buffer, with 50 μal of this diluted secondary antibody added to each well. The plates were incubated with the secondary antibody for 1 hour at room temperature, and then washed five times with wash buffer. Finally, the wells were developed with 50 μl of TMB (Life Sciences) for 3-5 min before stopping the reaction with 50 μl of 2 N sulfuric acid. The resulting plate readouts were measured at a wavelength of 450 nm.

Bio-layer interferometry (BLI): The kinetics of E2 cores and nanoparticle binding to HCV-specific antibodies was measured using an Octet Red96 instrument (fortéBio, Pall Life Sciences). All assays were performed with agitation set to 1000 rpm in fortéBio 1× kinetic buffer. The final volume for all the solutions was 200 μl per well. Assays were performed at 30° C. in solid black 96-well plates (Geiger Bio-One). 5 μg $ml^{-1}$ of antibody in 1× kinetic buffer was loaded onto the surface of anti-human Fc Capture Biosensors (AHC) for E2 cores and of anti-human Fc Quantitation Biosensors (AHQ) for nanoparticles for 300 s. A 60 s biosensor baseline step was applied prior to the analysis of the association of the antibody on the biosensor to the antigen in solution for 200 s. A two-fold concentration gradient of antigen, starting at 3.57 μM for E2 cores and 52.08 nM for nanoparticles, depending on the size, was used in a titration series of six. The dissociation of the interaction was followed for 300 s. Correction of baseline drift was performed by subtracting the mean value of shifts recorded for a sensor loaded with antibody but not incubated with antigen and for a sensor without antibody but incubated with antigen. Octet data were processed by FortéBio's data acquisition software v.8.1. Experimental data were fitted with the binding equations describing a 2:1 interaction to achieve optimal fitting. Of note, E2mc3-v1 binding was also measured using AHQ to facilitate the comparison of antibody binding signals with nanoparticles.

Differential scanning calorimetry (DSC): Thermal melting curves of HCV E2 core glycoproteins were obtained with a MicroCal VP-Capillary calorimeter (Malvern). The purified E2 glycoproteins produced from 293S cells were buffer exchanged into 1×PBS and concentrated to 27-50 µM before analysis by the instrument. Melting was probed at a scan rate of $90°$ C.·h$^{-1}$ from $25°$ C. to $110°$ C. Data processing, including buffer correction, normalization, and baseline subtraction, was conducted using the standardized protocol from the Origin 7.0 software.

Protein expression and purification for crystallization: The E2 constructs were expressed and purified as described above. Fabs AR3A and AR3B were expressed and purified as previously described by Giang et al., Proc. Natl. Acad. Sci. U.S.A. 109:6205-6210, 2012). The mAbs were purified on a protein G affinity column followed by size exclusion chromatography using a Superdex-200 column (Pharmacia) in 50 mM NaCl, 20 mM Tris-HCl (pH=7.2) buffer.

Crystallization and structural determination of HK6a E2c3-Fab E1-AR3A-protein G complex. The HK6a E2c3-Fab E1-AR3A complex was formed by overnight incubation of purified E2 and Fabs in a molar ratio of 1:1.2:1.25 (E2:Fab E1:Fab AR3A) at room temperature followed by size exclusion chromatography (Superdex-200) to remove unbound Fabs using 20 mM Tris and 50 mM NaCl (pH=7.2) buffer. Crystallization experiments were performed using our high-throughput CrystalMation™ robotic system (Rigaku) using the vapor diffusion sitting drop method (drop size 0.3 µl) at $20°$ C. and resulted with crystals that diffracted to ~5 Å. To improve crystal resolution, prior to the crystallization experiment, domain III of protein G (PDB entry 1IGC) was added to the HK6a E2c3-Fab E1-AR3A complex in a molar ratio of 1:2 (complex: protein G). These experiments resulted in crystals of HK6a E2c3-Fab E1-AR3A-protein G that diffracted to 3.40 Å. Crystals were obtained using a reservoir solution of 0.2M magnesium chloride, 10% (w/v) PEG 3000, 15% ethylene glycol, 0.1M Na-cacodylate, pH=6.5. Prior to data collection, crystals were flash cooled in liquid nitrogen. Diffraction data sets were collected at Stanford Synchrotron Radiation Lightsource (SSRL). Data were integrated and scaled using HKL2000 and structure was solved by molecular replacement method using Phaser with the HK6a E2c3-AR3A (PDB entry 6BKB) as a search model. Structure refinement was carried out in Phenix and model building with COOT.

Crystallization and structural determination of E2mc3-Fab complexes: Crystallization experiments were performed for H77 E2mc3, H77 E2mc3v-1, H77 E2mc3v-6, HK6a E2mc3, and HK6a E2mc3v-1 in complex with AR3A, AR3B, AR3C, and AR3D Fabs. The E2-Fab complexes were formed by overnight incubation of purified E2 and Fabs in a molar ratio of 1:1.25 (E2:Fab) at room temperature followed by size exclusion chromatography (Superdex-200) to remove unbound Fabs using 20 mM Tris and 50 mM NaCl (pH=7.2) buffer. Crystallization screening using our high-throughput CrystalMation™ robotic system (Rigaku) using the vapor diffusion sitting drop method (drop size 0.3 µl) at $20°$ C. resulted in crystals of H77 E2mc3-v1-AR3C, H77 E2mc3-v6-AR3C, and HK6a E2mc3-v1-AR3B that diffracted to 1.90 Å, 2.85 Å, and 2.06 Å, respectively. Crystals of the H77 E2mc3-v1-AR3C complex were obtained using a reservoir solution of 20% (w/v) PEG 3500, 0.2M di-ammonium hydrogen phosphate; H77 E2mc3-v6-AR3C complex from 20% (w/v) PEG 3500, 0.2M Na-thiocyanate, pH=6.9; and HK6a E2mc3-v1-AR3B complex from 20% (w/v) PEG 8000, 0.1M HEPES pH=7.5. Prior to data collection, H77 E2mc3-v6-AR3C and HK6a E2mc3-v1-AR3B crystals were cryoprotected with 10-15% ethylene glycol and flash cooled in liquid nitrogen. Diffraction data sets were collected at the Advanced Photon Source (APS). Data were integrated and scaled using HKL2000. Structures were solved by molecular replacement method using Phaser with the H77 E2c-AR3C or HK6a E2c3-AR3B (PDB entry 4MWF or 6BKC) as a search model. Structure refinement was carried out in Phenix and model building with COOT.

Negative stain electron microscopy (EM): The EM experiments were conducted at the Scripps Core Microscopy Facility. Briefly, nanoparticle samples were prepared at the concentration of 0.01 mg/ml. Carbon-coated copper grids (400 mesh) were glow-discharged and 8 µL of each sample was adsorbed for 2 minutes. Excess sample was wicked away and grids were negatively stained with 2% uranyl formate for 2 minutes. Excess stain was wicked away and the grids were allowed to dry. Samples were analyzed at 80 kV with a Talos L120C transmission electron microscope (Thermo Fisher) and images were acquired with a CETA 16M CMOS camera.

Mouse immunization and sample collection: The Institutional Animal Care and Use Committee (IACUC) guidelines were followed with animal subjects tested in the immunization study. Eight-week-old BALB/c mice were purchased from The Jackson Laboratory. The mice were housed in ventilated cages in environmentally controlled rooms at TSRI, in compliance with an approved IACUC protocol and AAALAC guidelines. At week 0, each mouse was immunized with 200 µl of antigen/adjuvant mix containing 50 µg of antigen and 100 µl AddaVax adjuvant (Invivogen) per manufacturer's instruction via the intramuscular (i.m.) route. At weeks 3, 6 and 9, the animals were boosted with 50 µg of antigen formulated in AddaVax adjuvant. At week 11, the animals were terminally bled through the retro orbital membrane using heparinized capillary tubes. Samples were diluted with an equal volume of PBS and then overlaid on 4.5 ml of Ficoll/Histopaque in a 15 ml SepMate tube (StemCell) and spun at 1200 RPM for 10 min at $20°$ C. to separate plasma and cells. The plasma was heat inactivated at $56°$ C. for 30 min, spun at 1200 RPM for 10 min, and sterile filtered. The cells were washed once in PBS and then resuspended in 1 ml of ACK Red Blood Cell lysis buffer (Lonza). After two rounds of washing with PBS, PBMCs were resuspended in 2 ml of Bambanker Freezing Media (Lymphotec Inc.). Spleens were also harvested and grounded against a 40-µm cell strainer (BD Falcon) to release the splenocytes into a cell suspension. The cells were centrifuged, washed in PBS, treated with 10 ml of RBC lysis buffer per manufacturer's specifications, and resuspended in Bambanker Freezing Media for cell freezing. While serum and plasma were used in HCVpp neutralization assays, 80% of the serum from individual mice in study #1 (9, 10, and 10 in groups 1, 2, and 3, respectively) was purified using a 0.2-ml protein G spin kit (Thermo Scientific) following the manufacturer's instructions. Purified IgGs were used to assess the polyclonal serum NAb response in HCVpp assays.

HCV neutralization assay: HCV pseudotyped particle (HCVpp) assays were utilized to assess the neutralizing activity of vaccine-induced antibody response in mouse sera, as well as synthesized antibodies from the next-generation sequencing (NGS) analysis of bulk-sorted mouse splenic B cells. Briefly, HCVpps were generated by co-transfection of 293T cells with pNL4-3.lucR-E-plasmid and the corresponding expression plasmids encoding the E1E2 genes at a 4:1 ratio by polyethylenimine as previously described by Bazzill et al., *Nano Lett.* 18:7832-7838, 2018. In vitro neutralization was carried on Huh7.5 cells using a single dilution of 1:50 for mouse sera and three concentrations (10 µg/ml, 1.0 µg/ml, and 0.1 µg/ml) for antibodies. Full neutralization curves were determined for IgGs purified from mice in study #1 against autologous H77 (1a) and heterologous SA13 (5a), with a starting IgG concentration of 100 µg/ml and a series of three-fold dilutions.

Bulk sorting of HCV E2-specific mouse B cells: Spleens were harvested from immunized mice 15 days after the last immunization and cell suspension was prepared. Cells were stained as follows: dead cells were excluded by staining with Fixable Aqua Dead Cell Stain kit (Thermo Fisher L34957). Receptors FcγIII (CD16) and FcγII (CD32) were blocked by adding 20 µl of 2.4G2 mAb (BD Pharmigen N553142). Cells were then incubated with 10 µg/ml of biotinylated HCV E2mc3 protein. Briefly, E2mc3 was generated by biotinylation of the individual Avi-tagged HCV E2mc3 using biotin ligase BirA according to the manufacturer's instructions (Avidity LLC). Biotin excess was removed by SEC on a Superdex 200 column (GE Healthcare). In the SEC profile, the Avi-tagged E2mc3 peak is centered at 14.5 ml, while a broader peak of biotin ligase can be found at 18-23 ml. Cells and biotinylated proteins were incubated for 5 min at 4° C., followed by the addition of 2.5 µl of anti-mouse IgG fluorescently labeled with FITC (Jackson ImmunoResearch 115-095-071) and incubated for 15 min at 4° C. Finally, 5 µl of premium-grade allophycocyanin (APC)-labeled streptavidin were added to the cells and incubated for 15 min at 4° C. In each step, cells were washed with DPBS and the sorting buffer was 0.5 ml FACS buffer. FITC$^+$ APC$^+$ E2mc3 specific B cells were sorted using BD FACSAria II into Eppendorf tube with 500 µl of FACS buffer.

Next-generation sequencing (NGS) and bioinformatics analysis of mouse B cells: A 5'-rapid amplification of cDNA ends (RACE) protocol has been reported for unbiased sequencing of mouse B cell repertoires. See He et al., *Sci. Adv.* 4, eaau6769, 2018; and Morris et al., *mBio* 8, e00036-00017, 2017. Here, this protocol was applied to bulk-sorted, E2-specific mouse splenic B cells. Briefly, 5'-RACE cDNA was obtained from bulk-sorted splenic B cells of each mouse with SMART-Seq v4 Ultra Low Input RNA Kit for Sequencing (TaKaRa). The immunoglobulin PCRs were set up with Platinum Taq High-Fidelity DNA Polymerase (Life Technologies) in a total volume of 50 µl, with 5 µl of cDNA as template, 1 µl of 5'-RACE primer, and 1 µl of 10 µM reverse primer. The 5'-RACE primer contained a PGM/S5 P1 adaptor, while the reverse primer contained a PGM/S5 A adaptor. We adapted the mouse 3'-$C_\gamma$1-3/3'-$C_\mu$ inner primers and 3'-mCK outer primer as reverse primers for 5'-RACE PCR processing of heavy and light (K) chains. A total of 25 cycles of PCR was performed and the expected PCR products (500-600 bp) were gel purified (Qiagen). NGS was performed on the Ion S5 GeneStudio system. Briefly, heavy and light (K) chain libraries from the same mouse were quantitated using Qubit® 2.0 Fluorometer with Qubit® dsDNA HS Assay Kit, and then mixed using a ratio of 3:1 before being pooled with antibody libraries of other mice at an equal ratio for sequencing. Template preparation and (Ion 530) chip loading were performed on Ion Chef using the Ion 520/530 Ext Kit, followed by sequencing on the Ion S5 system with default settings. The mouse Antibodyomics pipeline was used to process the raw data and to determine distributions for germline gene usage, somatic hypermutation (SHM), germline divergence, and H/KCDR3 loop length.

List of some sequences disclosed herein.

E2 (H77 genotype 1a) (SEQ ID NO: 1), HCV polyprotein residues 384-746
ETHVTGGSAGHTTAGLVGLLTPGAKQNIQLINTNGSWHINSTALNCNDSL

TTGWLAGLFYRHKFNSSGCPERLASCRRLTDFAQGWGPISYANGSGLDER

PYCWHYPPRPCGIVPAKSVCGPVYCFTPSPVVVGTTDRSGAPTYSWGAND

TDVFVLNNTRPPLGNWFGCTWMNSTGFTKVCGAPPCVIGGVGNNTLLCPT

DCFRKHPEATYSRCGSGPWITPRCMVDYPYRLWHYPCTINYTIFKVRMYV

GGVEHRLEAACNWTRGERCDLEDRDRSELSPLLLSTTQWQVLPCSFTTLP

ALSTGLIHLHQNIVDVQYLYGVGSSIASWAIKWEYVVLLFLLLADARVCS

CLWMMLLISQAEA

E2ΔTM (H77 isolate) (SEQ ID NO: 2), HCV polyprotein residues 384-717
ETHVTGGSAGHTTAGLVGLLTPGAKQNIQLINTNGSWHINSTALNCNDSL

TTGWLAGLFYRHKFNSSGCPERLASCRRLTDFAQGWGPISYANGSGLDER

PYCWHYPPRPCGIVPAKSVCGPVYCFTPSPVVVGTTDRSGAPTYSWGAND

TDVFVLNNTRPPLGNWFGCTWMNSTGFTKVCGAPPCVIGGVGNNTLLCPT

DCFRKHPEATYSRCGSGPWITPRCMVDYPYRLWHYPCTINYTIFKVRMYV

GGVEHRLEAACNWTRGERCDLEDRDRSELSPLLLSTTQWQVLPCSFTTLP

ALSTGLIHLHQNIVDVQYLYGVGSSIASWAIKWE

E2c (H77 isolate) (SEQ ID NO: 3), engineered core sequence
QLINTNGSWHINSTALNCNESLNTGWLAGLFYQHKFDSSG<u>CPERLASCGS</u>

<u>SGC</u>WHY<u>PPRP</u>CGIVPAKSVCGPVYCFTPSPVVVGTTDRSGAPTYSWGAND

TDVFVLNNTRPPLGNWFGCTWMNSTGFTKVCGAPPCVIGGVGDNTLLCPT

DCFRKHPEATYSRCGSGPWITPRCMVDYPYRLWHYPCTINYTIFKVRMYV

GGVEHRLEAACN (the VR2 disordered region underlined)

E2c3 (H77 isolate) (SEQ ID NO: 4), engineered core sequence
QLINTNGSWHINSTALNCNESLNTGWLAGLFYQHKFDSSG<u>CPERLASCGS</u>

<u>SGC</u>WHY<u>PPRP</u>CGIVPAKSVCGPVYCFTPSPVVVGTTDRSGAPTYSWGAND

TDVFVLNNTRPPLGNWFGCTWMNSTGFTKVCGAPPGGPTDGGSGPWITPR

CMVDYPYRLWHYPCTINYTIFKVRMYVGGVEHRLEAACN (the VR2 disordered region underlined)

E2mc3 (SEQ ID NO: 26), redesigned E2 core
QLINTNGSWHINSTALNCNESLNTGWLAGLFYQHKFDSSG<u>CPERASGHYP</u>

<u>RPC</u>GIVPAKSVCGPVYCFTPSPVVVGTTDRSGAPTYSWGANDTDVFVLNN

TGNWFGCTWMNSTGFTKVCGAPPGGPTDGGSGPWITPRCMVDYPYRLWHY

PCTINYTIFKVRMYVGGVEHRLEAACN (tVR2 sequence underlined)

E2mc3 variants 1-10 (SEQ ID NOs: 27-36): the PERASG (SEQ ID NO: 52) motif is replaced respectively with the 6 aa or 5 aa sequences shown in SEQ ID NOs: 11-20.

E2mc3 (HK6a genotype 6a), redesigned E2 core (SEQ ID NO: 37)
QLINTNGSWHINRTALNCNDSLQTGFITSLFYAKNVDSSG<u>CPERASGHYP RPC</u>DVVSARTVCGPVYCFTPSPVVVGTTDKLGIPTYNWGENETDVFMLES LGGWFGCTWMNSTGFTKTCGAPPGGPTDGGSGPWITPRCLVDYPYRLWHY PCTVNFTLHKVRMFVGGIEHRFDAACN (tVR2 sequence underlined)

E2mc3 (HK6a genotype 6a) variant 1 (SEQ ID NO: 38):
QLINTNGSWHINRTALNCNDSLQTGFITSLFYAKNVDSSGC<u>QNWDEPHYP RPC</u>DVVSARTVCGPVYCFTPSPVVVGTTDKLGIPTYNWGENETDVFMLES LGGWFGCTWMNSTGFTKTCGAPPGGPTDGGSGPWITPRCLVDYPYRLWHY PCTVNFTLHKVRMFVGGIEHRFDAACN (changed residues in tVR2 underlined)

tVR2 sequences of E2mc3 variants 1-10:
CQNWDEPHYPRPC (SEQ ID NO: 65), CKVNIDPHYPRPC (SEQ ID NO: 66), CEKVEELHYPRPC (SEQ ID NO: 67), CPDENMKHYPRPC (SEQ ID NO: 68), CKREEKMHYPRPC (SEQ ID NO: 69), CPKTEVHYPRPC (SEQ ID NO: 70), CKRVDIHYPRPC (SEQ ID NO: 71), CPSDMVHYPRPC (SEQ ID NO: 72), CPNEEEHYPRPC (SEQ ID NO: 73), and CKKEIRHYPRPC (SEQ ID NO: 74).

The invention thus has been disclosed broadly and illustrated in reference to representative embodiments described above. It is understood that various modifications can be made to the present invention without departing from the spirit and scope thereof.

It is further noted that all publications, sequence accession numbers, patents and patent applications cited herein are hereby expressly incorporated by reference in their entirety and for all purposes as if each is individually so denoted. Definitions that are contained in text incorporated by reference are excluded to the extent that they contradict definitions in this disclosure.

What is claimed is:

1. A modified HCV E2 ectodomain polypeptide, comprising an engineered E2 ectodomain sequence that contains a truncation in the VR2 disordered region, wherein the truncated VR2 disordered region contains less than 20 amino acid residues.

2. The modified HCV E2 ectodomain polypeptide of claim 1, wherein the VR2 disordered region corresponds to amino acid residues 452-494 of the full length polyprotein of HCV H77 isolate.

3. The modified HCV E2 ectodomain polypeptide of claim 2, wherein truncation of the VR2 disordered region comprises replacing residues 41-61 of SEQ ID NO:4, CPERLASCGSSGCWHYPPRPC (SEQ ID NO:6), with CPERASGHYPRPC (SEQ ID NO:10).

4. The modified HCV E2 ectodomain polypeptide of claim 2, wherein truncation of the VR2 disordered region comprises replacing residues 41-61 of SEQ ID NO:4, CPERLASCGSSGCWHYPPRPC (SEQ ID NO:6), with a sequence set forth in CXXXXXXHYPRPC (SEQ ID NO:8) or CXXXXXHYPRPC (SEQ ID NO:9), wherein X is any amino acid residue.

5. The modified HCV E2 ectodomain polypeptide of claim 4, wherein XXXXXX in SEQ ID NO:8 is QNWDEP (SEQ ID NO:11), KVNIDP (SEQ ID NO:12), EKVEEL (SEQ ID NO:13), PDENMK (SEQ ID NO:14), or KREEKM (SEQ ID NO:15).

6. The modified HCV E2 ectodomain polypeptide of claim 4, wherein XXXXX in SEQ ID NO:9 is PKTEV (SEQ ID NO:16), KRVDI (SEQ ID NO:17), PSDMV (SEQ ID NO:18), PNEEE (SEQ ID NO:19), or KKEIR (SEQ ID NO:20).

7. The modified HCV E2 ectodomain polypeptide of claim 1, further comprising a deletion in the β-sandwich loop connecting βsheets 6 and 7 of the β-sandwich domain.

8. The modified HCV E2 ectodomain polypeptide of claim 7, wherein deletion of the β-sandwich loop sequence (SEQ ID NO:21) comprises deletion of one or more residues that form the tip of the β-sandwich loop.

9. The modified HCV E2 ectodomain polypeptide of claim 8, wherein residues that form the tip of the β-sandwich loop are residues 543-546 from HCV genotype 1a H77 isolate polyprotein sequence.

10. The modified HCV E2 ectodomain polypeptide of claim 8, wherein residues 543-546 from HCV genotype 1a H77 isolate polyprotein sequence, RPPL (SEQ ID NO:22), are deleted.

11. The modified HCV E2 ectodomain polypeptide of claim 7, comprising an amino acid sequence as set forth in any one of SEQ ID NOs:26-38, a conservatively modified variant or a substantially identical sequence thereof.

12. A polynucleotide encoding the modified HCV E2 ectodomain polypeptide of claim 1.

13. A pharmaceutical composition, comprising the modified HCV E2 ectodomain polypeptide of claim 1, and a pharmaceutically acceptable carrier.

14. An immunogenic composition, comprising a modified HCV E2 ectodomain polypeptide of claim 1 that is displayed on the surface of a self-assembling nanoparticle.

15. The immunogenic composition of claim 14, wherein the C-terminus of the modified HCV E2 ectodomain polypeptide is fused to the N-terminus of a subunit of the self-assembling nanoparticle via a linker sequence.

16. The immunogenic composition of claim 15, wherein the linker sequence comprises (GGGGS)2 (SEQ ID NO:42).

17. The immunogenic composition of claim 14, wherein the modified HCV E2 ectodomain polypeptide comprises an amino acid sequence as set forth in any one of SEQ ID NOs:26 38.

18. The immunogenic composition of claim 14, wherein the subunit of the self-assembling nanoparticle comprises the polypeptide as shown in SEQ ID NO:39 (E2p), SEQ ID NO: 40 (I3-01), or SEQ ID NO: 41 (ferritin).

19. A polynucleotide, encoding a fusion protein comprising a modified HCV E2 ectodomain polypeptide of claim 1 and a self-assembling nanoparticle subunit, wherein the modified HCV E2 ectodomain polypeptide is fused at its C-terminus to the N-terminus of the self-assembling nanoparticle subunit.

20. A pharmaceutical composition, comprising the immunogenic composition of claim 14, and a pharmaceutically acceptable carrier.

21. A method of treating HCV infection in a subject, comprising administering to the subject a pharmaceutical composition comprising a therapeutically effective amount of the immunogenic composition of claim 14, thereby treating HCV infection in the subject.

\* \* \* \* \*

SEQUENCE LISTING

<160> NUMBER OF SEQ ID NOS: 76

<210> SEQ ID NO 1
<211> LENGTH: 363
<212> TYPE: PRT
<213> ORGANISM: Hepatitis C virus

<400> SEQUENCE: 1

Glu Thr His Val Thr Gly Gly Ser Ala Gly His Thr Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Asp
        35                  40                  45

Ser Leu Thr Thr Gly Trp Leu Ala Gly Leu Phe Tyr Arg His Lys Phe
    50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
        115                 120                 125

Ser Pro Val Val Gly Thr Thr Asp Arg Ser Gly Ala Pro Thr Tyr
    130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
        195                 200                 205

-continued

```
Ala Thr Tyr Ser Arg Cys Gly Ser Gly Pro Trp Ile Thr Pro Arg Cys
    210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
                260                 265                 270

Asp Arg Asp Arg Ser Glu Leu Ser Pro Leu Leu Leu Ser Thr Thr Gln
                275                 280                 285

Trp Gln Val Leu Pro Cys Ser Phe Thr Thr Leu Pro Ala Leu Ser Thr
290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335

Val Leu Leu Phe Leu Leu Leu Ala Asp Ala Arg Val Cys Ser Cys Leu
                340                 345                 350

Trp Met Met Leu Leu Ile Ser Gln Ala Glu Ala
                355                 360
```

<210> SEQ ID NO 2
<211> LENGTH: 334
<212> TYPE: PRT
<213> ORGANISM: Hepatitis C virus

<400> SEQUENCE: 2

```
Glu Thr His Val Thr Gly Gly Ser Ala Gly His Thr Ala Gly Leu
1               5                   10                  15

Val Gly Leu Leu Thr Pro Gly Ala Lys Gln Asn Ile Gln Leu Ile Asn
                20                  25                  30

Thr Asn Gly Ser Trp His Ile Asn Ser Thr Ala Leu Asn Cys Asn Asp
            35                  40                  45

Ser Leu Thr Thr Gly Trp Leu Ala Gly Leu Phe Tyr Arg His Lys Phe
    50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
        115                 120                 125

Ser Pro Val Val Val Gly Thr Thr Asp Arg Ser Gly Ala Pro Thr Tyr
    130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
    210                 215                 220
```

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
            245                 250                 255

Leu Glu Ala Ala Cys Asn Trp Thr Arg Gly Glu Arg Cys Asp Leu Glu
        260                 265                 270

Asp Arg Asp Arg Ser Glu Leu Ser Pro Leu Leu Leu Ser Thr Thr Gln
    275                 280                 285

Trp Gln Val Leu Pro Cys Ser Phe Thr Thr Leu Pro Ala Leu Ser Thr
290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu
                325                 330

<210> SEQ ID NO 3
<211> LENGTH: 212
<212> TYPE: PRT
<213> ORGANISM: Artificial sequence
<220> FEATURE:
<223> OTHER INFORMATION: Synthetic sequence

<400> SEQUENCE: 3

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
            20                  25                  30

Gln His Lys Phe Asp Ser Ser Gly Cys Pro Glu Arg Leu Ala Ser Cys
        35                  40                  45

Gly Ser Ser Gly Cys Trp His Tyr Pro Pro Arg Pro Cys Gly Ile Val
    50                  55                  60

Pro Ala Lys Ser Val Cys Gly Pro Val Tyr Cys Phe Thr Pro Ser Pro
65                  70                  75                  80

Val Val Val Gly Thr Thr Asp Arg Ser Gly Ala Pro Thr Tyr Ser Trp
                85                  90                  95

Gly Ala Asn Asp Thr Asp Val Phe Val Leu Asn Asn Thr Arg Pro Pro
            100                 105                 110

Leu Gly Asn Trp Phe Gly Cys Thr Trp Met Asn Ser Thr Gly Phe Thr
        115                 120                 125

Lys Val Cys Gly Ala Pro Pro Cys Val Ile Gly Gly Val Gly Asp Asn
    130                 135                 140

Thr Leu Leu Cys Pro Thr Asp Cys Phe Arg Lys His Pro Glu Ala Thr
145                 150                 155                 160

Tyr Ser Arg Cys Gly Ser Gly Pro Trp Ile Thr Pro Arg Cys Met Val
                165                 170                 175

Asp Tyr Pro Tyr Arg Leu Trp His Tyr Pro Cys Thr Ile Asn Tyr Thr
            180                 185                 190

Ile Phe Lys Val Arg Met Tyr Val Gly Gly Val Glu His Arg Leu Glu
        195                 200                 205

Ala Ala Cys Asn
    210

<210> SEQ ID NO 4
<211> LENGTH: 189
<212> TYPE: PRT
<213> ORGANISM: Artificial sequence

```
<220> FEATURE:
<223> OTHER INFORMATION: Synthetic sequence

<400> SEQUENCE: 4

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
            20                  25                  30

Gln His Lys Phe Asp Ser Ser Gly Cys Pro Glu Arg Leu Ala Ser Cys
        35                  40                  45

Gly Ser Ser Gly Cys Trp His Tyr Pro Pro Arg Pro Cys Gly Ile Val
    50                  55                  60

Pro Ala Lys Ser Val Cys Gly Pro Val Tyr Cys Phe Thr Pro Ser Pro
65              70                  75                  80

Val Val Val Gly Thr Thr Asp Arg Ser Gly Ala Pro Thr Tyr Ser Trp
                85                  90                  95

Gly Ala Asn Asp Thr Asp Val Phe Val Leu Asn Asn Thr Arg Pro Pro
            100                 105                 110

Leu Gly Asn Trp Phe Gly Cys Thr Trp Met Asn Ser Thr Gly Phe Thr
        115                 120                 125

Lys Val Cys Gly Ala Pro Pro Gly Gly Pro Thr Asp Gly Gly Ser Gly
    130                 135                 140

Pro Trp Ile Thr Pro Arg Cys Met Val Asp Tyr Pro Tyr Arg Leu Trp
145                 150                 155                 160

His Tyr Pro Cys Thr Ile Asn Tyr Thr Ile Phe Lys Val Arg Met Tyr
                165                 170                 175

Val Gly Gly Val Glu His Arg Leu Glu Ala Ala Cys Asn
                180                 185

<210> SEQ ID NO 5
<211> LENGTH: 43
<212> TYPE: PRT
<213> ORGANISM: Hepatitis C virus

<400> SEQUENCE: 5

Cys Pro Glu Arg Leu Ala Ser Cys Arg Arg Leu Thr Asp Phe Ala Gln
1               5                   10                  15

Gly Trp Gly Pro Ile Ser Tyr Ala Asn Gly Ser Gly Leu Asp Glu Arg
            20                  25                  30

Pro Tyr Cys Trp His Tyr Pro Pro Arg Pro Cys
        35                  40

<210> SEQ ID NO 6
<211> LENGTH: 21
<212> TYPE: PRT
<213> ORGANISM: Artificial sequence
<220> FEATURE:
<223> OTHER INFORMATION: Synthetic sequence

<400> SEQUENCE: 6

Cys Pro Glu Arg Leu Ala Ser Cys Gly Ser Ser Gly Cys Trp His Tyr
1               5                   10                  15

Pro Pro Arg Pro Cys
            20

<210> SEQ ID NO 7
<211> LENGTH: 18
<212> TYPE: PRT
<213> ORGANISM: Artificial sequence
```

```
<220> FEATURE:
<223> OTHER INFORMATION: Synthetic sequence
<220> FEATURE:
<221> NAME/KEY: MISC_FEATURE
<222> LOCATION: (2)..(11)
<223> OTHER INFORMATION: X is any amino acid residue
<220> FEATURE:
<221> NAME/KEY: MISC_FEATURE
<222> LOCATION: (5)..(11)
<223> OTHER INFORMATION: the residue can be either present or absent
<220> FEATURE:
<221> NAME/KEY: MISC_FEATURE
<222> LOCATION: (5)..(11)

<400> SEQUENCE: 7

Cys Xaa Xaa Xaa Xaa Xaa Xaa Xaa Xaa Xaa Xaa Asn His Tyr Pro Arg
1               5                   10                  15

Pro Cys

<210> SEQ ID NO 8
<211> LENGTH: 13
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (2)..(7)
<223> OTHER INFORMATION: X is any amino acid residue

<400> SEQUENCE: 8

Cys Xaa Xaa Xaa Xaa Xaa Xaa His Tyr Pro Arg Pro Cys
1               5                   10

<210> SEQ ID NO 9
<211> LENGTH: 12
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (2)..(6)
<223> OTHER INFORMATION: X is any amino acid residue

<400> SEQUENCE: 9

Cys Xaa Xaa Xaa Xaa Xaa His Tyr Pro Arg Pro Cys
1               5                   10

<210> SEQ ID NO 10
<211> LENGTH: 13
<212> TYPE: PRT
<213> ORGANISM: Artificial sequence
<220> FEATURE:
<223> OTHER INFORMATION: Synthetic sequence

<400> SEQUENCE: 10

Cys Pro Glu Arg Ala Ser Gly His Tyr Pro Arg Pro Cys
1               5                   10

<210> SEQ ID NO 11
<211> LENGTH: 6
<212> TYPE: PRT
<213> ORGANISM: Artificial sequence
<220> FEATURE:
<223> OTHER INFORMATION: Synthetic sequence
```

```
<400> SEQUENCE: 11

Gln Asn Trp Asp Glu Pro
1               5

<210> SEQ ID NO 12
<211> LENGTH: 6
<212> TYPE: PRT
<213> ORGANISM: Artificial sequence
<220> FEATURE:
<223> OTHER INFORMATION: Synthetic sequence

<400> SEQUENCE: 12

Lys Val Asn Ile Asp Pro
1               5

<210> SEQ ID NO 13
<211> LENGTH: 6
<212> TYPE: PRT
<213> ORGANISM: Artificial sequence
<220> FEATURE:
<223> OTHER INFORMATION: Synthetic sequence

<400> SEQUENCE: 13

Glu Lys Val Glu Glu Leu
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic sequence

<400> SEQUENCE: 14

Pro Asp Glu Asn Met Lys
1               5

<210> SEQ ID NO 15
<211> LENGTH: 6
<212> TYPE: PRT
<213> ORGANISM: Artificial sequence
<220> FEATURE:
<223> OTHER INFORMATION: Synthetic sequence

<400> SEQUENCE: 15

Lys Arg Glu Glu Lys Met
1               5

<210> SEQ ID NO 16
<211> LENGTH: 5
<212> TYPE: PRT
<213> ORGANISM: Artificial sequence
<220> FEATURE:
<223> OTHER INFORMATION: Synthetic sequence

<400> SEQUENCE: 16

Pro Lys Thr Glu Val
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic sequence
```

<400> SEQUENCE: 17

Lys Arg Val Asp Ile
1               5

<210> SEQ ID NO 18
<211> LENGTH: 5
<212> TYPE: PRT
<213> ORGANISM: Artificial sequence
<220> FEATURE:
<223> OTHER INFORMATION: Synthetic sequence

<400> SEQUENCE: 18

Pro Ser Asp Met Val
1               5

<210> SEQ ID NO 19
<211> LENGTH: 5
<212> TYPE: PRT
<213> ORGANISM: Artificial sequence
<220> FEATURE:
<223> OTHER INFORMATION: Synthetic sequence

<400> SEQUENCE: 19

Pro Asn Glu Glu Glu
1               5

<210> SEQ ID NO 20
<211> LENGTH: 5
<212> TYPE: PRT
<213> ORGANISM: Artificial sequence
<220> FEATURE:
<223> OTHER INFORMATION: Synthetic sequence

<400> SEQUENCE: 20

Lys Lys Glu Ile Arg
1               5

<210> SEQ ID NO 21
<211> LENGTH: 11
<212> TYPE: PRT
<213> ORGANISM: Hepatitis C virus

<400> SEQUENCE: 21

Asn Asn Thr Arg Pro Pro Leu Gly Asn Trp Phe
1               5                   10

<210> SEQ ID NO 22
<211> LENGTH: 4
<212> TYPE: PRT
<213> ORGANISM: Hepatitis C virus

<400> SEQUENCE: 22

Arg Pro Pro Leu
1

<210> SEQ ID NO 23
<211> LENGTH: 6
<212> TYPE: PRT
<213> ORGANISM: Hepatitis C virus

<400> SEQUENCE: 23

Thr Arg Pro Pro Leu Gly
1               5

<210> SEQ ID NO 24
<211> LENGTH: 5
<212> TYPE: PRT
<213> ORGANISM: Hepatitis C virus

<400> SEQUENCE: 24

Thr Arg Pro Pro Leu
1               5

<210> SEQ ID NO 25
<211> LENGTH: 5
<212> TYPE: PRT
<213> ORGANISM: Hepatitis C virus

<400> SEQUENCE: 25

Arg Pro Pro Leu Gly
1               5

<210> SEQ ID NO 26
<211> LENGTH: 177
<212> TYPE: PRT
<213> ORGANISM: Artificial sequence
<220> FEATURE:
<223> OTHER INFORMATION: Synthetic sequence

<400> SEQUENCE: 26

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
            20                  25                  30

Gln His Lys Phe Asp Ser Ser Gly Cys Pro Glu Arg Ala Ser Gly His
        35                  40                  45

Tyr Pro Arg Pro Cys Gly Ile Val Pro Ala Lys Ser Val Cys Gly Pro
    50                  55                  60

Val Tyr Cys Phe Thr Pro Ser Pro Val Val Gly Thr Thr Asp Arg
65                  70                  75                  80

Ser Gly Ala Pro Thr Tyr Ser Trp Gly Ala Asn Asp Thr Asp Val Phe
                85                  90                  95

Val Leu Asn Asn Thr Gly Asn Trp Phe Gly Cys Thr Trp Met Asn Ser
            100                 105                 110

Thr Gly Phe Thr Lys Val Cys Gly Ala Pro Pro Gly Gly Pro Thr Asp
        115                 120                 125

Gly Gly Ser Gly Pro Trp Ile Thr Pro Arg Cys Met Val Asp Tyr Pro
    130                 135                 140

Tyr Arg Leu Trp His Tyr Pro Cys Thr Ile Asn Tyr Thr Ile Phe Lys
145                 150                 155                 160

Val Arg Met Tyr Val Gly Gly Val Glu His Arg Leu Glu Ala Ala Cys
                165                 170                 175

Asn

<210> SEQ ID NO 27
<211> LENGTH: 177
<212> TYPE: PRT
<213> ORGANISM: Artificial sequence
<220> FEATURE:
<223> OTHER INFORMATION: Synthetic sequence

<400> SEQUENCE: 27

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
            20                  25                  30

Gln His Lys Phe Asp Ser Ser Gly Cys Gln Asn Trp Asp Glu Pro His
        35                  40                  45

Tyr Pro Arg Pro Cys Gly Ile Val Pro Ala Lys Ser Val Cys Gly Pro
    50                  55                  60

Val Tyr Cys Phe Thr Pro Ser Pro Val Val Gly Thr Thr Asp Arg
65                  70                  75                  80

Ser Gly Ala Pro Thr Tyr Ser Trp Gly Ala Asn Asp Thr Asp Val Phe
                85                  90                  95

Val Leu Asn Asn Thr Gly Asn Trp Phe Gly Cys Thr Trp Met Asn Ser
            100                 105                 110

Thr Gly Phe Thr Lys Val Cys Gly Ala Pro Pro Gly Gly Pro Thr Asp
        115                 120                 125

Gly Gly Ser Gly Pro Trp Ile Thr Pro Arg Cys Met Val Asp Tyr Pro
    130                 135                 140

Tyr Arg Leu Trp His Tyr Pro Cys Thr Ile Asn Tyr Thr Ile Phe Lys
145                 150                 155                 160

Val Arg Met Tyr Val Gly Gly Val Glu His Arg Leu Glu Ala Ala Cys
                165                 170                 175

Asn

<210> SEQ ID NO 28
<211> LENGTH: 177
<212> TYPE: PRT
<213> ORGANISM: Artificial sequence
<220> FEATURE:
<223> OTHER INFORMATION: Synthetic sequence

<400> SEQUENCE: 28

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
            20                  25                  30

Gln His Lys Phe Asp Ser Ser Gly Cys Lys Val Asn Ile Asp Pro His
        35                  40                  45

Tyr Pro Arg Pro Cys Gly Ile Val Pro Ala Lys Ser Val Cys Gly Pro
    50                  55                  60

Val Tyr Cys Phe Thr Pro Ser Pro Val Val Val Gly Thr Thr Asp Arg
65                  70                  75                  80

Ser Gly Ala Pro Thr Tyr Ser Trp Gly Ala Asn Asp Thr Asp Val Phe
                85                  90                  95

Val Leu Asn Asn Thr Gly Asn Trp Phe Gly Cys Thr Trp Met Asn Ser
            100                 105                 110

Thr Gly Phe Thr Lys Val Cys Gly Ala Pro Pro Gly Gly Pro Thr Asp
        115                 120                 125

Gly Gly Ser Gly Pro Trp Ile Thr Pro Arg Cys Met Val Asp Tyr Pro
    130                 135                 140

Tyr Arg Leu Trp His Tyr Pro Cys Thr Ile Asn Tyr Thr Ile Phe Lys
145                 150                 155                 160

-continued

```
Val Arg Met Tyr Val Gly Gly Val Glu His Arg Leu Glu Ala Ala Cys
            165                 170                 175
Asn
```

<210> SEQ ID NO 29
<211> LENGTH: 177
<212> TYPE: PRT
<213> ORGANISM: Artificial sequence
<220> FEATURE:
<223> OTHER INFORMATION: Synthetic sequence

<400> SEQUENCE: 29

```
Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
                20                  25                  30

Gln His Lys Phe Asp Ser Ser Gly Cys Glu Lys Val Glu Glu Leu His
            35                  40                  45

Tyr Pro Arg Pro Cys Gly Ile Val Pro Ala Lys Ser Val Cys Gly Pro
        50                  55                  60

Val Tyr Cys Phe Thr Pro Ser Pro Val Val Gly Thr Thr Asp Arg
65                  70                  75                  80

Ser Gly Ala Pro Thr Tyr Ser Trp Gly Ala Asn Asp Thr Asp Val Phe
                85                  90                  95

Val Leu Asn Asn Thr Gly Asn Trp Phe Gly Cys Thr Trp Met Asn Ser
                100                 105                 110

Thr Gly Phe Thr Lys Val Cys Gly Ala Pro Pro Gly Gly Pro Thr Asp
            115                 120                 125

Gly Gly Ser Gly Pro Trp Ile Thr Pro Arg Cys Met Val Asp Tyr Pro
        130                 135                 140

Tyr Arg Leu Trp His Tyr Pro Cys Thr Ile Asn Tyr Thr Ile Phe Lys
145                 150                 155                 160

Val Arg Met Tyr Val Gly Gly Val Glu His Arg Leu Glu Ala Ala Cys
                165                 170                 175
Asn
```

<210> SEQ ID NO 30
<211> LENGTH: 177
<212> TYPE: PRT
<213> ORGANISM: Artificial sequence
<220> FEATURE:
<223> OTHER INFORMATION: Synthetic sequence

<400> SEQUENCE: 30

```
Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
                20                  25                  30

Gln His Lys Phe Asp Ser Ser Gly Cys Pro Asp Glu Asn Met Lys His
            35                  40                  45

Tyr Pro Arg Pro Cys Gly Ile Val Pro Ala Lys Ser Val Cys Gly Pro
        50                  55                  60

Val Tyr Cys Phe Thr Pro Ser Pro Val Val Gly Thr Thr Asp Arg
65                  70                  75                  80

Ser Gly Ala Pro Thr Tyr Ser Trp Gly Ala Asn Asp Thr Asp Val Phe
                85                  90                  95
```

Val Leu Asn Asn Thr Gly Asn Trp Phe Gly Cys Thr Trp Met Asn Ser
                100                 105                 110

Thr Gly Phe Thr Lys Val Cys Gly Ala Pro Pro Gly Gly Pro Thr Asp
            115                 120                 125

Gly Gly Ser Gly Pro Trp Ile Thr Pro Arg Cys Met Val Asp Tyr Pro
        130                 135                 140

Tyr Arg Leu Trp His Tyr Pro Cys Thr Ile Asn Tyr Thr Ile Phe Lys
145                 150                 155                 160

Val Arg Met Tyr Val Gly Gly Val Glu His Arg Leu Glu Ala Ala Cys
                165                 170                 175

Asn

<210> SEQ ID NO 31
<211> LENGTH: 177
<212> TYPE: PRT
<213> ORGANISM: Artificial sequence
<220> FEATURE:
<223> OTHER INFORMATION: Synthetic sequence

<400> SEQUENCE: 31

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
                20                  25                  30

Gln His Lys Phe Asp Ser Ser Gly Cys Lys Arg Glu Glu Lys Met His
            35                  40                  45

Tyr Pro Arg Pro Cys Gly Ile Val Pro Ala Lys Ser Val Cys Gly Pro
        50                  55                  60

Val Tyr Cys Phe Thr Pro Ser Pro Val Val Val Gly Thr Thr Asp Arg
65                  70                  75                  80

Ser Gly Ala Pro Thr Tyr Ser Trp Gly Ala Asn Asp Thr Asp Val Phe
                85                  90                  95

Val Leu Asn Asn Thr Gly Asn Trp Phe Gly Cys Thr Trp Met Asn Ser
                100                 105                 110

Thr Gly Phe Thr Lys Val Cys Gly Ala Pro Pro Gly Gly Pro Thr Asp
            115                 120                 125

Gly Gly Ser Gly Pro Trp Ile Thr Pro Arg Cys Met Val Asp Tyr Pro
        130                 135                 140

Tyr Arg Leu Trp His Tyr Pro Cys Thr Ile Asn Tyr Thr Ile Phe Lys
145                 150                 155                 160

Val Arg Met Tyr Val Gly Gly Val Glu His Arg Leu Glu Ala Ala Cys
                165                 170                 175

Asn

<210> SEQ ID NO 32
<211> LENGTH: 176
<212> TYPE: PRT
<213> ORGANISM: Artificial sequence
<220> FEATURE:
<223> OTHER INFORMATION: Synthetic sequence

<400> SEQUENCE: 32

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
                20                  25                  30

```
Gln His Lys Phe Asp Ser Ser Gly Cys Pro Lys Thr Glu Val His Tyr
            35                  40                  45

Pro Arg Pro Cys Gly Ile Val Pro Ala Lys Ser Val Cys Gly Pro Val
    50                  55                  60

Tyr Cys Phe Thr Pro Ser Pro Val Val Val Gly Thr Thr Asp Arg Ser
65                  70                  75                  80

Gly Ala Pro Thr Tyr Ser Trp Gly Ala Asn Asp Thr Asp Val Phe Val
                85                  90                  95

Leu Asn Asn Thr Gly Asn Trp Phe Gly Cys Thr Trp Met Asn Ser Thr
                100                 105                 110

Gly Phe Thr Lys Val Cys Gly Ala Pro Pro Gly Gly Pro Thr Asp Gly
            115                 120                 125

Gly Ser Gly Pro Trp Ile Thr Pro Arg Cys Met Val Asp Tyr Pro Tyr
    130                 135                 140

Arg Leu Trp His Tyr Pro Cys Thr Ile Asn Tyr Thr Ile Phe Lys Val
145                 150                 155                 160

Arg Met Tyr Val Gly Gly Val Glu His Arg Leu Glu Ala Ala Cys Asn
                165                 170                 175
```

<210> SEQ ID NO 33
<211> LENGTH: 176
<212> TYPE: PRT
<213> ORGANISM: Artificial sequence
<220> FEATURE:
<223> OTHER INFORMATION: Synthetic sequence

<400> SEQUENCE: 33

```
Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
                20                  25                  30

Gln His Lys Phe Asp Ser Ser Gly Cys Lys Arg Val Asp Ile His Tyr
            35                  40                  45

Pro Arg Pro Cys Gly Ile Val Pro Ala Lys Ser Val Cys Gly Pro Val
    50                  55                  60

Tyr Cys Phe Thr Pro Ser Pro Val Val Val Gly Thr Thr Asp Arg Ser
65                  70                  75                  80

Gly Ala Pro Thr Tyr Ser Trp Gly Ala Asn Asp Thr Asp Val Phe Val
                85                  90                  95

Leu Asn Asn Thr Gly Asn Trp Phe Gly Cys Thr Trp Met Asn Ser Thr
                100                 105                 110

Gly Phe Thr Lys Val Cys Gly Ala Pro Pro Gly Gly Pro Thr Asp Gly
            115                 120                 125

Gly Ser Gly Pro Trp Ile Thr Pro Arg Cys Met Val Asp Tyr Pro Tyr
    130                 135                 140

Arg Leu Trp His Tyr Pro Cys Thr Ile Asn Tyr Thr Ile Phe Lys Val
145                 150                 155                 160

Arg Met Tyr Val Gly Gly Val Glu His Arg Leu Glu Ala Ala Cys Asn
                165                 170                 175
```

<210> SEQ ID NO 34
<211> LENGTH: 176
<212> TYPE: PRT
<213> ORGANISM: Artificial sequence
<220> FEATURE:
<223> OTHER INFORMATION: Synthetic sequence

<400> SEQUENCE: 34

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
                20                  25                  30

Gln His Lys Phe Asp Ser Ser Gly Cys Pro Ser Asp Met Val His Tyr
            35                  40                  45

Pro Arg Pro Cys Gly Ile Val Pro Ala Lys Ser Val Cys Gly Pro Val
        50                  55                  60

Tyr Cys Phe Thr Pro Ser Pro Val Val Val Gly Thr Thr Asp Arg Ser
65                  70                  75                  80

Gly Ala Pro Thr Tyr Ser Trp Gly Ala Asn Asp Thr Asp Val Phe Val
                85                  90                  95

Leu Asn Asn Thr Gly Asn Trp Phe Gly Cys Thr Trp Met Asn Ser Thr
            100                 105                 110

Gly Phe Thr Lys Val Cys Gly Ala Pro Pro Gly Gly Pro Thr Asp Gly
        115                 120                 125

Gly Ser Gly Pro Trp Ile Thr Pro Arg Cys Met Val Asp Tyr Pro Tyr
    130                 135                 140

Arg Leu Trp His Tyr Pro Cys Thr Ile Asn Tyr Thr Ile Phe Lys Val
145                 150                 155                 160

Arg Met Tyr Val Gly Gly Val Glu His Arg Leu Glu Ala Ala Cys Asn
                165                 170                 175

<210> SEQ ID NO 35
<211> LENGTH: 176
<212> TYPE: PRT
<213> ORGANISM: Artificial sequence
<220> FEATURE:
<223> OTHER INFORMATION: Synthetic sequence

<400> SEQUENCE: 35

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
                20                  25                  30

Gln His Lys Phe Asp Ser Ser Gly Cys Pro Asn Glu Glu His Tyr
            35                  40                  45

Pro Arg Pro Cys Gly Ile Val Pro Ala Lys Ser Val Cys Gly Pro Val
        50                  55                  60

Tyr Cys Phe Thr Pro Ser Pro Val Val Val Gly Thr Thr Asp Arg Ser
65                  70                  75                  80

Gly Ala Pro Thr Tyr Ser Trp Gly Ala Asn Asp Thr Asp Val Phe Val
                85                  90                  95

Leu Asn Asn Thr Gly Asn Trp Phe Gly Cys Thr Trp Met Asn Ser Thr
            100                 105                 110

Gly Phe Thr Lys Val Cys Gly Ala Pro Pro Gly Gly Pro Thr Asp Gly
        115                 120                 125

Gly Ser Gly Pro Trp Ile Thr Pro Arg Cys Met Val Asp Tyr Pro Tyr
    130                 135                 140

Arg Leu Trp His Tyr Pro Cys Thr Ile Asn Tyr Thr Ile Phe Lys Val
145                 150                 155                 160

Arg Met Tyr Val Gly Gly Val Glu His Arg Leu Glu Ala Ala Cys Asn
                165                 170                 175

```
<210> SEQ ID NO 36
<211> LENGTH: 176
<212> TYPE: PRT
<213> ORGANISM: Artificial sequence
<220> FEATURE:
<223> OTHER INFORMATION: Synthetic sequence

<400> SEQUENCE: 36

Gln Leu Ile Asn Thr Asn Gly Ser Trp His Ile Asn Ser Thr Ala Leu
1               5                   10                  15

Asn Cys Asn Glu Ser Leu Asn Thr Gly Trp Leu Ala Gly Leu Phe Tyr
            20                  25                  30

Gln His Lys Phe Asp Ser Ser Gly Cys Lys Lys Glu Ile Arg His Tyr
        35                  40                  45

Pro Arg Pro Cys Gly Ile Val Pro Ala Lys Ser Val Cys Gly Pro Val
    50                  55                  60

Tyr Cys Phe Thr Pro Ser Pro Val Val Val Gly Thr Thr Asp Arg Ser
65                  70                  75                  80

Gly Ala Pro Thr Tyr Ser Trp Gly Ala Asn Asp Thr Asp Val Phe Val
                85                  90                  95

Leu Asn Asn Thr Gly Asn Trp Phe Gly Cys Thr Trp Met Asn Ser Thr
            100                 105                 110

Gly Phe Thr Lys Val Cys Gly Ala Pro Pro Gly Gly Pro Thr Asp Gly
        115                 120                 125

Gly Ser Gly Pro Trp Ile Thr Pro Arg Cys Met Val Asp Tyr Pro Tyr
    130                 135                 140

Arg Leu Trp His Tyr Pro Cys Thr Ile Asn Tyr Thr Ile Phe Lys Val
145                 150                 155                 160

Arg Met Tyr Val Gly Gly Val Glu His Arg Leu Glu Ala Ala Cys Asn
                165                 170                 175

<210> SEQ ID NO 37
<211> LENGTH: 177
<212> TYPE: PRT
<213> ORGANISM: Artificial sequence
<220> FEATURE:
<223> OTHER INFORMATION: Synthetic sequence

<400> SEQUENCE: 37

Gln Leu Ile Asn Thr Asn Gly Ser Trp His Ile Asn Arg Thr Ala Leu
1               5                   10                  15

Asn Cys Asn Asp Ser Leu Gln Thr Gly Phe Ile Thr Ser Leu Phe Tyr
            20                  25                  30

Ala Lys Asn Val Asp Ser Ser Gly Cys Pro Glu Arg Ala Ser Gly His
        35                  40                  45

Tyr Pro Arg Pro Cys Asp Val Val Ser Ala Arg Thr Val Cys Gly Pro
    50                  55                  60

Val Tyr Cys Phe Thr Pro Ser Pro Val Val Gly Thr Thr Asp Lys
65                  70                  75                  80

Leu Gly Ile Pro Thr Tyr Asn Trp Gly Glu Asn Glu Thr Asp Val Phe
                85                  90                  95

Met Leu Glu Ser Leu Gly Gly Trp Phe Gly Cys Thr Trp Met Asn Ser
            100                 105                 110

Thr Gly Phe Thr Lys Thr Cys Gly Ala Pro Pro Gly Gly Pro Thr Asp
        115                 120                 125

Gly Gly Ser Gly Pro Trp Ile Thr Pro Arg Cys Leu Val Asp Tyr Pro
    130                 135                 140
```

```
Tyr Arg Leu Trp His Tyr Pro Cys Thr Val Asn Phe Thr Leu His Lys
145                 150                 155                 160

Val Arg Met Phe Val Gly Gly Ile Glu His Arg Phe Asp Ala Ala Cys
                165                 170                 175

Asn

<210> SEQ ID NO 38
<211> LENGTH: 177
<212> TYPE: PRT
<213> ORGANISM: Artificial sequence
<220> FEATURE:
<223> OTHER INFORMATION: Synthetic sequence

<400> SEQUENCE: 38

Gln Leu Ile Asn Thr Asn Gly Ser Trp His Ile Asn Arg Thr Ala Leu
1               5                   10                  15

Asn Cys Asn Asp Ser Leu Gln Thr Gly Phe Ile Thr Ser Leu Phe Tyr
                20                  25                  30

Ala Lys Asn Val Asp Ser Ser Gly Cys Gln Asn Trp Asp Glu Pro His
            35                  40                  45

Tyr Pro Arg Pro Cys Asp Val Val Ser Ala Arg Thr Val Cys Gly Pro
50                  55                  60

Val Tyr Cys Phe Thr Pro Ser Pro Val Val Gly Thr Thr Asp Lys
65                  70                  75                  80

Leu Gly Ile Pro Thr Tyr Asn Trp Gly Glu Asn Glu Thr Asp Val Phe
                85                  90                  95

Met Leu Glu Ser Leu Gly Gly Trp Phe Gly Cys Thr Trp Met Asn Ser
                100                 105                 110

Thr Gly Phe Thr Lys Thr Cys Gly Ala Pro Pro Gly Gly Pro Thr Asp
            115                 120                 125

Gly Gly Ser Gly Pro Trp Ile Thr Pro Arg Cys Leu Val Asp Tyr Pro
130                 135                 140

Tyr Arg Leu Trp His Tyr Pro Cys Thr Val Asn Phe Thr Leu His Lys
145                 150                 155                 160

Val Arg Met Phe Val Gly Gly Ile Glu His Arg Phe Asp Ala Ala Cys
                165                 170                 175

Asn

<210> SEQ ID NO 39
<211> LENGTH: 242
<212> TYPE: PRT
<213> ORGANISM: Artificial sequence
<220> FEATURE:
<223> OTHER INFORMATION: Synthetic sequence

<400> SEQUENCE: 39

Ala Ala Ala Lys Pro Ala Thr Thr Glu Gly Glu Phe Pro Glu Thr Arg
1               5                   10                  15

Glu Lys Met Ser Gly Ile Arg Arg Ala Ile Ala Lys Ala Met Val His
                20                  25                  30

Ser Lys His Thr Ala Pro His Val Thr Leu Met Asp Glu Ala Asp Val
            35                  40                  45

Thr Lys Leu Val Ala His Arg Lys Lys Phe Lys Ala Ile Ala Ala Glu
        50                  55                  60

Lys Gly Ile Lys Leu Thr Phe Leu Pro Tyr Val Val Lys Ala Leu Val
65                  70                  75                  80
```

-continued

```
Ser Ala Leu Arg Glu Tyr Pro Val Leu Asn Thr Ala Ile Asp Asp Glu
                 85                  90                  95

Thr Glu Glu Ile Ile Gln Lys His Tyr Tyr Asn Ile Gly Ile Ala Ala
            100                 105                 110

Asp Thr Asp Arg Gly Leu Leu Val Pro Val Ile Lys His Ala Asp Arg
        115                 120                 125

Lys Pro Ile Phe Ala Leu Ala Gln Glu Ile Asn Glu Leu Ala Glu Lys
    130                 135                 140

Ala Arg Asp Gly Lys Leu Thr Pro Gly Glu Met Lys Gly Ala Ser Cys
145                 150                 155                 160

Thr Ile Thr Asn Ile Gly Ser Ala Gly Gly Gln Trp Phe Thr Pro Val
                165                 170                 175

Ile Asn His Pro Glu Val Ala Ile Leu Gly Ile Gly Arg Ile Ala Glu
            180                 185                 190

Lys Pro Ile Val Arg Asp Gly Glu Ile Val Ala Ala Pro Met Leu Ala
        195                 200                 205

Leu Ser Leu Ser Phe Asp His Arg Met Ile Asp Gly Ala Thr Ala Gln
    210                 215                 220

Lys Ala Leu Asn His Ile Lys Arg Leu Leu Ser Asp Pro Glu Leu Leu
225                 230                 235                 240

Leu Met
```

<210> SEQ ID NO 40
<211> LENGTH: 205
<212> TYPE: PRT
<213> ORGANISM: Artificial sequence
<220> FEATURE:
<223> OTHER INFORMATION: Synthetic sequence

<400> SEQUENCE: 40

```
Met Lys Met Glu Glu Leu Phe Lys Lys His Lys Ile Val Ala Val Leu
1               5                  10                  15

Arg Ala Asn Ser Val Glu Glu Ala Lys Lys Lys Ala Leu Ala Val Phe
            20                  25                  30

Leu Gly Gly Val His Leu Ile Glu Ile Thr Phe Thr Val Pro Asp Ala
        35                  40                  45

Asp Thr Val Ile Lys Glu Leu Ser Phe Leu Lys Glu Met Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175
```

```
Val Gly Ser Ala Leu Val Lys Gly Thr Pro Val Glu Val Ala Glu Lys
            180                 185                 190

Ala Lys Ala Phe Val Glu Lys Ile Arg Gly Cys Thr Glu
        195                 200                 205

<210> SEQ ID NO 41
<211> LENGTH: 167
<212> TYPE: PRT
<213> ORGANISM: Artificial sequence
<220> FEATURE:
<223> OTHER INFORMATION: Synthetic sequence

<400> SEQUENCE: 41

Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Ser Trp Cys Tyr
            20                  25                  30

Thr His Ser Leu Asp Gly Ala Gly Leu Phe Leu Phe Asp His Ala Ala
        35                  40                  45

Glu Glu Tyr Glu His Ala Lys Lys Leu Ile Ile Phe Leu Asn Glu Asn
    50                  55                  60

Asn Val Pro Val Gln Leu Thr Ser Ile Ser Ala Pro Glu His Lys Phe
65                  70                  75                  80

Glu Gly Leu Thr Gln Ile Phe Gln Lys Ala Tyr Glu His Glu Gln His
                85                  90                  95

Ile Ser Glu Ser Ile Asn Asn Ile Val Asp His Ala Ile Lys Ser Lys
            100                 105                 110

Asp His Ala Thr Phe Asn Phe Leu Gln Trp Tyr Val Ala Glu Gln His
        115                 120                 125

Glu Glu Glu Val Leu Phe Lys Asp Ile Leu Asp Lys Ile Glu Leu Ile
    130                 135                 140

Gly Asn Glu Asn His Gly Leu Tyr Leu Ala Asp Gln Tyr Val Lys Gly
145                 150                 155                 160

Ile Ala Lys Ser Arg Lys Ser
                165

<210> SEQ ID NO 42
<211> LENGTH: 10
<212> TYPE: PRT
<213> ORGANISM: Artificial sequence
<220> FEATURE:
<223> OTHER INFORMATION: Synthetic sequence

<400> SEQUENCE: 42

Gly Gly Gly Gly Ser Gly Gly Gly Gly Ser
1               5                   10

<210> SEQ ID NO 43
<211> LENGTH: 6
<212> TYPE: PRT
<213> ORGANISM: Artificial sequence
<220> FEATURE:
<223> OTHER INFORMATION: Synthetic sequence

<400> SEQUENCE: 43

Gly Gly Pro Thr Asp Gly
1               5
```

```
<210> SEQ ID NO 44
<211> LENGTH: 6
<212> TYPE: PRT
<213> ORGANISM: Artificial sequence
<220> FEATURE:
<223> OTHER INFORMATION: Synthetic sequence

<400> SEQUENCE: 44

Arg Ala Tyr Thr Leu Ser
1               5

<210> SEQ ID NO 45
<211> LENGTH: 17
<212> TYPE: PRT
<213> ORGANISM: Artificial sequence
<220> FEATURE:
<223> OTHER INFORMATION: Synthetic sequence

<400> SEQUENCE: 45

Arg Ile Met Pro Thr Val Gly Ile Thr Asn Tyr Ala Gln Lys Phe Gln
1               5                   10                  15

Gly

<210> SEQ ID NO 46
<211> LENGTH: 12
<212> TYPE: PRT
<213> ORGANISM: Artificial sequence
<220> FEATURE:
<223> OTHER INFORMATION: Synthetic sequence

<400> SEQUENCE: 46

Gly Pro Tyr Val Gly Leu Gly Glu Gly Phe Ser Glu
1               5                   10

<210> SEQ ID NO 47
<211> LENGTH: 16
<212> TYPE: PRT
<213> ORGANISM: Artificial sequence
<220> FEATURE:
<223> OTHER INFORMATION: Synthetic sequence

<400> SEQUENCE: 47

Arg Ser Thr Gln Ser Leu Val Tyr Ser Asp Gly Asn Thr Tyr Leu Asn
1               5                   10                  15

<210> SEQ ID NO 48
<211> LENGTH: 7
<212> TYPE: PRT
<213> ORGANISM: Artificial sequence
<220> FEATURE:
<223> OTHER INFORMATION: Synthetic sequence

<400> SEQUENCE: 48

Lys Val Ser Asn Arg Asp Ser
1               5

<210> SEQ ID NO 49
<211> LENGTH: 9
<212> TYPE: PRT
<213> ORGANISM: Artificial sequence
<220> FEATURE:
<223> OTHER INFORMATION: Synthetic sequence

<400> SEQUENCE: 49

Met Gln Gly Ala His Trp Pro Pro Thr
1               5
```

<210> SEQ ID NO 50
<211> LENGTH: 13
<212> TYPE: PRT
<213> ORGANISM: Artificial sequence
<220> FEATURE:
<223> OTHER INFORMATION: Synthetic sequence

<400> SEQUENCE: 50

Cys Gly Gly Gly Gly Gly Gly His Tyr Pro Arg Pro Cys
1               5                   10

<210> SEQ ID NO 51
<211> LENGTH: 13
<212> TYPE: PRT
<213> ORGANISM: Artificial sequence
<220> FEATURE:
<223> OTHER INFORMATION: Synthetic sequence

<400> SEQUENCE: 51

Cys Gly Gly Gly Gly Gly Gly His Tyr Pro Arg Pro Cys
1               5                   10

<210> SEQ ID NO 52
<211> LENGTH: 6
<212> TYPE: PRT
<213> ORGANISM: Hepatitis C virus

<400> SEQUENCE: 52

Pro Glu Arg Ala Ser Gly
1               5

<210> SEQ ID NO 53
<211> LENGTH: 56
<212> TYPE: PRT
<213> ORGANISM: Hepatitis C virus

<400> SEQUENCE: 53

Gly Leu Phe Tyr Gln His Lys Phe Asn Ser Ser Gly Cys Pro Glu Arg
1               5                   10                  15

Leu Ala Ser Cys Arg Arg Leu Thr Asp Phe Ala Gln Gly Trp Gly Pro
            20                  25                  30

Ile Ser Tyr Ala Asn Gly Ser Gly Leu Asp Glu Arg Pro Tyr Cys Trp
        35                  40                  45

His Tyr Pro Pro Arg Pro Cys Gly
    50                  55

<210> SEQ ID NO 54
<211> LENGTH: 34
<212> TYPE: PRT
<213> ORGANISM: Artificial sequence
<220> FEATURE:
<223> OTHER INFORMATION: Synthetic sequence

<400> SEQUENCE: 54

Gly Leu Phe Tyr Gln His Lys Phe Asp Ser Ser Gly Cys Pro Glu Arg
1               5                   10                  15

Leu Ala Ser Cys Gly Ser Ser Gly Cys Trp His Tyr Pro Pro Arg Pro
            20                  25                  30

Cys Gly

<210> SEQ ID NO 55
<211> LENGTH: 34
<212> TYPE: PRT
<213> ORGANISM: Artificial sequence
<220> FEATURE:
<223> OTHER INFORMATION: Synthetic sequence

<400> SEQUENCE: 55

Ser Leu Phe Tyr Ala Lys Asn Val Asp Ser Ser Gly Cys Pro Glu Arg
1               5                   10                  15

Met Ala Ala Cys Gly Ser Ser Gly Cys Trp His Tyr Ala Pro Arg Pro
            20                  25                  30

Cys Asp

<210> SEQ ID NO 56
<211> LENGTH: 31
<212> TYPE: PRT
<213> ORGANISM: Artificial sequence
<220> FEATURE:
<223> OTHER INFORMATION: Synthetic sequence

<400> SEQUENCE: 56

His Ile Asn Ser Thr Ala Leu Asn Cys Asn Glu Ser Leu Asn Thr Gly
1               5                   10                  15

Trp Leu Ala Gly Leu Phe Tyr Gln His Lys Phe Asp Ser Ser Gly
            20                  25                  30

<210> SEQ ID NO 57
<211> LENGTH: 64
<212> TYPE: PRT
<213> ORGANISM: Artificial sequence
<220> FEATURE:
<223> OTHER INFORMATION: Synthetic sequence

<400> SEQUENCE: 57

His Cys Asn Ser Thr Ala Leu Asn Cys Asn Glu Ser Leu Asn Thr Gly
1               5                   10                  15

Trp Leu Ala Gly Leu Phe Tyr Gln His Lys Phe Asp Ser Ser Gly Arg
            20                  25                  30

Met Lys Gln Leu Glu Asp Lys Val Glu Thr Asn Leu Ser Lys Val Tyr
        35                  40                  45

His Asn Glu Asn Cys Val Ala Arg Leu Lys Lys Leu Val Gly Glu Arg
    50                  55                  60

<210> SEQ ID NO 58
<211> LENGTH: 33
<212> TYPE: PRT
<213> ORGANISM: Artificial sequence
<220> FEATURE:
<223> OTHER INFORMATION: Synthetic sequence

<400> SEQUENCE: 58

Arg Met Lys Gln Leu Glu Asp Lys Val Glu Glu Asn Leu Ser Lys Val
1               5                   10                  15

Tyr His Asn Glu Asn Glu Val Ala Arg Leu Lys Lys Leu Val Gly Glu
            20                  25                  30

Arg

<210> SEQ ID NO 59
<211> LENGTH: 12
<212> TYPE: PRT
<213> ORGANISM: Artificial sequence
<220> FEATURE:
<223> OTHER INFORMATION: Synthetic sequence

```
<400> SEQUENCE: 59

Gln Leu Ile Asn Thr Asn Gly Ser Trp His Ile Asn
1               5                   10

<210> SEQ ID NO 60
<211> LENGTH: 75
<212> TYPE: PRT
<213> ORGANISM: Artificial sequence
<220> FEATURE:
<223> OTHER INFORMATION: Synthetic sequence

<400> SEQUENCE: 60

Arg Leu Val Asn Cys Asn Gly Ser Trp Leu Ile Gly Leu Asp Arg Pro
1               5                   10                  15

Pro Tyr Pro Gly Ala Lys Gly Glu Asp Ile Tyr Asn Asn Val Ser Arg
            20                  25                  30

Lys Ala Trp Asp Glu Trp Gln Lys His Gln Thr Met Leu Ile Asn Glu
        35                  40                  45

Arg Arg Leu Asn Met Met Asn Ala Glu Asp Arg Lys Phe Leu Gln Gln
    50                  55                  60

Glu Met Asp Lys Phe Leu Ser Gly Glu Asp Tyr
65                  70                  75

<210> SEQ ID NO 61
<211> LENGTH: 81
<212> TYPE: PRT
<213> ORGANISM: Artificial sequence
<220> FEATURE:
<223> OTHER INFORMATION: Synthetic sequence

<400> SEQUENCE: 61

Gly His Met Ser Arg Thr Val Met Cys Arg Lys Tyr His Glu Glu Leu
1               5                   10                  15

Pro Gly Leu Asp Arg Pro Pro Tyr Pro Gly Ala Lys Gly Glu Asp Ile
            20                  25                  30

Tyr Asn Asn Val Ser Arg Lys Ala Trp Asp Glu Trp Gln Lys His Gln
        35                  40                  45

Thr Met Leu Ile Asn Glu Arg Arg Leu Asn Met Met Asn Ala Glu Asp
    50                  55                  60

Arg Lys Phe Leu Gln Gln Glu Met Asp Lys Phe Leu Ser Gly Glu Asp
65                  70                  75                  80

Tyr

<210> SEQ ID NO 62
<211> LENGTH: 11
<212> TYPE: PRT
<213> ORGANISM: Artificial sequence
<220> FEATURE:
<223> OTHER INFORMATION: Synthetic sequence

<400> SEQUENCE: 62

Pro Glu Arg Ala Ser Gly His Tyr Pro Arg Pro
1               5                   10

<210> SEQ ID NO 63
<211> LENGTH: 11
<212> TYPE: PRT
<213> ORGANISM: Artificial sequence
<220> FEATURE:
<223> OTHER INFORMATION: Synthetic sequence
```

```
<400> SEQUENCE: 63

Gly Gly Gly Gly Gly His Tyr Pro Arg Pro
1               5                   10

<210> SEQ ID NO 64
<211> LENGTH: 10
<212> TYPE: PRT
<213> ORGANISM: Artificial sequence
<220> FEATURE:
<223> OTHER INFORMATION: Synthetic sequence

<400> SEQUENCE: 64

Gly Gly Gly Gly Gly His Tyr Pro Arg Pro
1               5                   10

<210> SEQ ID NO 65
<211> LENGTH: 13
<212> TYPE: PRT
<213> ORGANISM: Artificial sequence
<220> FEATURE:
<223> OTHER INFORMATION: Synthetic sequence

<400> SEQUENCE: 65

Cys Gln Asn Trp Asp Glu Pro His Tyr Pro Arg Pro Cys
1               5                   10

<210> SEQ ID NO 66
<211> LENGTH: 13
<212> TYPE: PRT
<213> ORGANISM: Artificial sequence
<220> FEATURE:
<223> OTHER INFORMATION: Synthetic sequence

<400> SEQUENCE: 66

Cys Lys Val Asn Ile Asp Pro His Tyr Pro Arg Pro Cys
1               5                   10

<210> SEQ ID NO 67
<211> LENGTH: 13
<212> TYPE: PRT
<213> ORGANISM: Artificial sequence
<220> FEATURE:
<223> OTHER INFORMATION: Synthetic sequence

<400> SEQUENCE: 67

Cys Glu Lys Val Glu Glu Leu His Tyr Pro Arg Pro Cys
1               5                   10

<210> SEQ ID NO 68
<211> LENGTH: 13
<212> TYPE: PRT
<213> ORGANISM: Artificial sequence
<220> FEATURE:
<223> OTHER INFORMATION: Synthetic sequence

<400> SEQUENCE: 68

Cys Pro Asp Glu Asn Met Lys His Tyr Pro Arg Pro Cys
1               5                   10

<210> SEQ ID NO 69
<211> LENGTH: 13
<212> TYPE: PRT
<213> ORGANISM: Artificial sequence
<220> FEATURE:
<223> OTHER INFORMATION: Synthetic sequence
```

```
<400> SEQUENCE: 69

Cys Lys Arg Glu Glu Lys Met His Tyr Pro Arg Pro Cys
1               5                   10

<210> SEQ ID NO 70
<211> LENGTH: 12
<212> TYPE: PRT
<213> ORGANISM: Artificial sequence
<220> FEATURE:
<223> OTHER INFORMATION: Synthetic sequence

<400> SEQUENCE: 70

Cys Pro Lys Thr Glu Val His Tyr Pro Arg Pro Cys
1               5                   10

<210> SEQ ID NO 71
<211> LENGTH: 12
<212> TYPE: PRT
<213> ORGANISM: Artificial sequence
<220> FEATURE:
<223> OTHER INFORMATION: Synthetic sequence

<400> SEQUENCE: 71

Cys Lys Arg Val Asp Ile His Tyr Pro Arg Pro Cys
1               5                   10

<210> SEQ ID NO 72
<211> LENGTH: 12
<212> TYPE: PRT
<213> ORGANISM: Artificial sequence
<220> FEATURE:
<223> OTHER INFORMATION: Synthetic sequence

<400> SEQUENCE: 72

Cys Pro Ser Asp Met Val His Tyr Pro Arg Pro Cys
1               5                   10

<210> SEQ ID NO 73
<211> LENGTH: 12
<212> TYPE: PRT
<213> ORGANISM: Artificial sequence
<220> FEATURE:
<223> OTHER INFORMATION: Synthetic sequence

<400> SEQUENCE: 73

Cys Pro Asn Glu Glu His Tyr Pro Arg Pro Cys
1               5                   10

<210> SEQ ID NO 74
<211> LENGTH: 12
<212> TYPE: PRT
<213> ORGANISM: Artificial sequence
<220> FEATURE:
<223> OTHER INFORMATION: Synthetic sequence

<400> SEQUENCE: 74

Cys Lys Lys Glu Ile Arg His Tyr Pro Arg Pro Cys
1               5                   10

<210> SEQ ID NO 75
<211> LENGTH: 6
<212> TYPE: PRT
<213> ORGANISM: Artificial sequence
<220> FEATURE:
<223> OTHER INFORMATION: Synthetic sequence
```

```
<220> FEATURE:
<221> NAME/KEY: 1MISC_FEATURE
<222> LOCATION: (1)..(6)
<223> OTHER INFORMATION: X is any amino acid residue
<220> FEATURE:
<221> NAME/KEY: MISC_FEATURE
<222> LOCATION: (1)..(6)
<223> OTHER INFORMATION: X is any amino acid residue

<400> SEQUENCE: 75

Xaa Xaa Xaa Xaa Xaa Xaa
1               5

<210> SEQ ID NO 76
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(5)
<223> OTHER INFORMATION: X is any amino acid residue

<400> SEQUENCE: 76

Xaa Xaa Xaa Xaa Xaa
1               5
```